US012760329B2

(12) United States Patent
Stepanova et al.

(10) Patent No.: US 12,760,329 B2
(45) Date of Patent: Oct. 13, 2026

(54) CrRNA:tracrRNA-BASED BINARY LOGIC GATE DESIGN AS A TOOL FOR SYNTHETIC BIOLOGY

(71) Applicant: North Carolina State University, Raleigh, NC (US)

(72) Inventors: Anna Stepanova, Cary, NC (US); Jose Alonso, Cary, NC (US); Chengsong Zhao, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1092 days.

(21) Appl. No.: 17/783,786

(22) PCT Filed: Dec. 11, 2020

(86) PCT No.: PCT/US2020/064446
§ 371 (c)(1),
(2) Date: Jun. 9, 2022

(87) PCT Pub. No.: WO2021/119393
PCT Pub. Date: Jun. 17, 2021

(65) Prior Publication Data

US 2023/0051466 A1 Feb. 16, 2023

Related U.S. Application Data

(60) Provisional application No. 62/947,277, filed on Dec. 12, 2019.

(51) Int. Cl.
*C12N 15/90* (2006.01)
*C12N 9/22* (2006.01)
*C12N 15/113* (2010.01)
*C12N 15/63* (2006.01)

(52) U.S. Cl.
CPC ............ *C12N 15/907* (2013.01); *C12N 9/22* (2013.01); *C12N 15/113* (2013.01); *C12N 15/63* (2013.01); *C12N 15/905* (2013.01); *C12N 2310/20* (2017.05)

(58) Field of Classification Search
None
See application file for complete search history.

(56) References Cited

U.S. PATENT DOCUMENTS

2019/0233806 A1 8/2019 Garreau De Loubresse et al.

FOREIGN PATENT DOCUMENTS

WO 2013176772 A1 11/2013
WO 2013188638 A2 12/2013

OTHER PUBLICATIONS

Gander et al., "Digital logic circuits in yeast with CRISPR-dCas9 NOR gates" 8 Nature Communications 15459, 1-11 (Year: 2017).*
Agudelo, Daniel, et al., "Versatile and robust genome editing with *Streptococcus thermophilus* CRISPR1-Cas9", Genome Research, 30(1), 2020, 107-117.
Bentley, David L., "Coupling mRNA processing with transcription in time and space", Nat Rev Genet 15(3), 2014, 163-175.
Briner, Alexandra E., et al., "Guide RNA functional modules direct Cas9 activity and orthogonality", Mol Cell 56, 2014, 333-339.
Briner, Alexandra E., et al., "Lactobacillus buchneri genotyping on the basis of clustered regularly interspaced short palindromic repeat (CRISPR) locus diversity", Appl Environ Microbiol 80, 2014, 994-1001.
Casamitjana-Martinez, Eva, et al., "Root-Specific CLE19 Overexpression and the sol1/2 Suppressors Implicate a CLV-like Pathway in the Control of *Arabidopsis* Root Meristem Maintenance", Curr. Biol. 13, 2003, 1435-1441.
Cermak, Tomáš, et al., "A Multipurpose Toolkit to Enable Advanced Genome Engineering in Plants", Plant Cell 29, 2017, 1196-1217.
Chavez, Alejandro, et al., "Highly efficient Cas9-mediated transcriptional programming", Nat Methods 12, 2015, 326-328.
Chen, Baohui, et al., "Dynamic imaging of genomic loci in living human cells by an optimized CRISPR/Cas system", Cell 155, 2013, 1479-1491.
Clough, Steven J., et al., "Floral dip: a simplified method for Agrobacterium-mediated transformation of *Arabidopsis thaliana*", Plant J 16, 1998, 735-743.
Dominguez, Antonia A., "Beyond editing: repurposing CRISPR-Cas9 for precision genome regulation and interrogation", Nat Rev Mol Cell Biol 17, 2016, 5-15.
Gao, Yangbin, et al., "Self-processing of ribozyme-flanked RNAs into guide RNAs in vitro and in vivo for CRISPR-mediated genome editing", J Integr Plant Biol 56, 2014, 343-349.
Gasiunas, Giedrius, et al., "Cas9-crRNA ribonucleoprotein complex mediates specific DNA cleavage for adaptive immunity in bacteria", PNAS 109(36), 2012, E2579-E2586.
Jinek, et al., "A Programmable Dual-RNA-Guided DNA Endonuclease in Adaptive Bacterial Immunity", Science (American Association for the Advancement of Science), 337(6096), 2012, 816-821.
Lee, Ciaran M., et al., "The Neisseria meningitidis CRISPR-Cas9 System Enables Specific Genome Editing in Mammalian Cells", Molecular Therapy 24(3), 2016, 645-654.
Ma, Hanhui, et al., "Multiplexed labeling of genomic loci with dCas9 and engineered sgRNAs using CRISPRainbow", Nat Biotechnol 34, 2016, 528-530.
Miyamoto, Takafumi, et al., "Synthesizing biomolecule-based Boolean logic gates", ACS Synth Biol 2, 2013, 72-82.
Nishimasu, Hiroshi, et al., "Crystal structure of Cas9 in complex with guide RNA and target DNA", Cell, 156(5), 2014, 935-949.
Sarkar, Ananda K., et al., "Conserved factors regulate signalling in *Arabidopsis thaliana* shoot and root stem cell organizers", Nature 446, 2007, 811-814.

(Continued)

*Primary Examiner* — Nancy J Leith
(74) *Attorney, Agent, or Firm* — Myers Bigel, P.A.

(57) ABSTRACT

The invention relates to logic-gate-based Type II or Type V CRISPR-Cas constructs and methods for modifying gene expression using the CRISPR-Cas constructs and CRISPR-Cas effector proteins.

21 Claims, 25 Drawing Sheets

Specification includes a Sequence Listing.

(56) References Cited

OTHER PUBLICATIONS

Sarrion-Perdigones, Alejandro, et al., "GoldenBraid: an iterative cloning system for standardized assembly of reusable genetic modules", PLoS One 6, 2011, 21622.
Singh, Vijai, "Recent advances and opportunities in synthetic logic gates engineering in living cells", Syst Synth Biol 8, 2014, 271-282.
Smanski, Michael J., et al., "Synthetic biology to access and expand nature's chemical diversity", Nat Rev Microbiol 14, 2016, 135-149.
Song, J., et al., "Biochemical and Structural Insights into the Mechanism of DNA Recognition by *Arabidopsis* Ethylene Insensitive3", PLoS One 10, 2015, e0137439.
Steinert, Jeannette, et al., "Highly efficient heritable plant genome engineering using Cas9 orthologues from *Streptococcus thermophilus* and *Staphylococcus aureus*", Plant J 84(6), 2015, 1295-1305.
Stepanova, Anna N., et al., "Multilevel interactions between ethylene and auxin in *Arabidopsis* roots", The Plant Cell Online 19, 2007, 2169-2185.
Tiwari, et al., "The EDLL motif: a potent plant transcriptional activation domain from AP2/ERF transcription factors", The Plant Journal: For Cell and Molecular Biology, 70(5), 2012, 855-865.
Tsai, Shengdar Q., et al., "Dimeric CRISPR RNA-guided FokI nucleases for highly specific genome editing", Nat Biotechnol 32, 2014, 569-576.
Vazquez-Vilar, Marta, et al., "GB3.0: a platform for plant bio-design that connects functional DNA elements with associated biological data", Nucleic Acids Res 45, 2017, 2196-2209.
Xie, Kabin, et al., "Boosting CRISPR/Cas9 multiplex editing capability with the endogenous tRNA-processing system", Proc Natl Acad Sci U S A 112, 2015, 3570-3575.

* cited by examiner

Streptococcus pyogenes (Spy)

*Streptococcus thermophilus* CRISPR1 (*Sth1*)

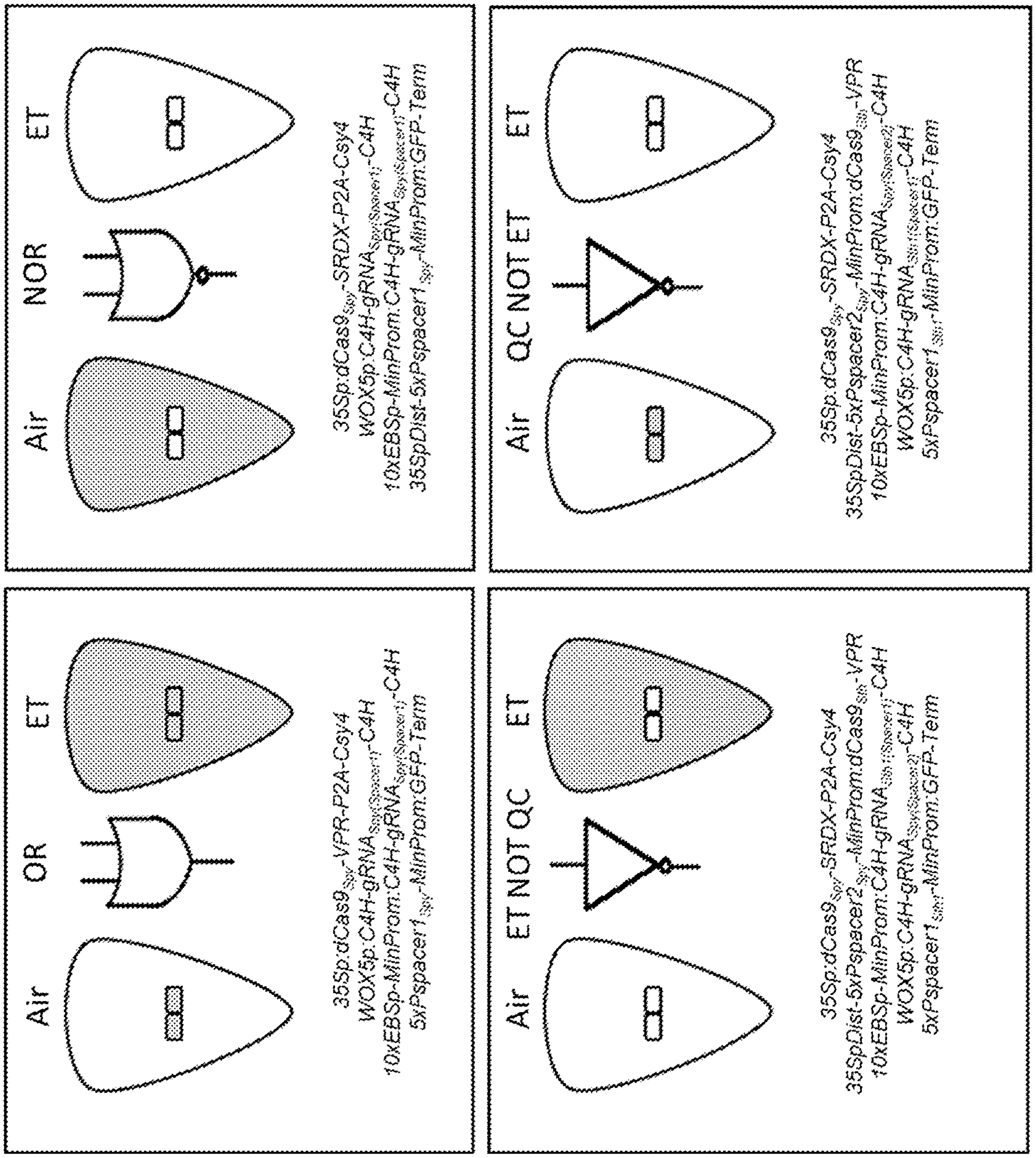
FIG. 10B (con't)

| AtU6p-crRNA$_{WT}$-AtU6t_AtU6p-tracrRNA$_{WT}$-AtU6t_35S-dCas9-EDLL-Tnos_35S-MS2-VPR-Tnos_SlDFRp-mCherry-Term35S#0 | 35S-HH-crRNA$_{WT}$-HDV-Term35S#0 | 35S-tRNA-crRNA$_{WT}$-tRNA-Term35S#0 |
|---|---|---|
| | AtU6p-tracrRNA$_{WT}$-AtU6t | |
| | 35S-dCas9-EDLL-Tnos_35S-MS2-VPR-Tnos_SlDFRp-mCherry-Term35S#0 | |

| | |
|---|---|
| AtU6p-sgRNA$_{Sth}$-AtU6t | AtU6p-crRNA$_{Sth24}$-AtU6t<br>AtU6p-tracrRNA$_{Sth24M}$-AtU6t |
| 35S-dCas9$_{Sth}$-EDLL-Term35S#0_35S-MS2-VPR-Tnos_SlDFRp$_{Sth}$-mCherry-Term35#0 | |

SEQUENCE LISTING

<160> NUMBER OF SEQ ID NOS: 30

<210> SEQ ID NO 1
<211> LENGTH: 42
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or u

<400> SEQUENCE: 1
nnnnnnnnnn nnnnnnnnnn guuuuagagc uaugcuguuu ug 42

<210> SEQ ID NO 2
<211> LENGTH: 83
<212> TYPE: RNA
<213> ORGANISM: Artificial Sequence
<220> FEATURE:
<223> OTHER INFORMATION: Synthetic polynucleotide

<400> SEQUENCE: 2
ggaaccauuc aaaacagcau agcaaguuaa aauaaggcua guccguuauc aacuugaaaa 60
aguggcaccg agucggugcu uuu 83

<210> SEQ ID NO 3
<211> LENGTH: 57
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: n is a, c, g, or u

<400> SEQUENCE: 3
nnnnnnnnnn nnnnnnnnnn nguuuuugua cucucaagau uuaaguaacu guacaac 57

<210> SEQ ID NO 4
<211> LENGTH: 102
<212> TYPE: RNA
<213> ORGANISM: Artificial Sequence
<220> FEATURE:
<223> OTHER INFORMATION: Synthetic polynucleotide

<400> SEQUENCE: 4
guaaggggcg ccuuacacag uuacuuaaau cuugcagaag cuacaaagau aaggcuucau 60
gccgaaauca acacccuguc auuuuauggc agggguguuu cg 102

<210> SEQ ID NO 5
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 5
gactggttgg tgagagaaga gtctttgtac tctcaagatt taag 44

<210> SEQ ID NO 6
<211> LENGTH: 129
<212> TYPE: DNA
<213> ORGANISM: Artificial Sequence
<220> FEATURE:
<223> OTHER INFORMATION: Synthetic polynucleotide

<400> SEQUENCE: 6
cttaaatctt gagaagctac aaagataagg cttcatgccg aaatcaacac cctgtcattt 60
tatggcaggg tggggagcac atgaggaatc acccatgtgc gactcccaca gtcactgggg 120
agtcttccc 129

<210> SEQ ID NO 7

<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 7
gactggttgg tgagagaaga gtgacggaac aaaggtagaa ttgg 44

<210> SEQ ID NO 8
<211> LENGTH: 129
<212> TYPE: DNA
<213> ORGANISM: Artificial Sequence
<220> FEATURE:
<223> OTHER INFORMATION: Synthetic polynucleotide

<400> SEQUENCE: 8
ccaattctac ctttagcttc cgtcataagg cttcatgccg aaatcaacac cctgtcattt 60
tatggcaggg tggggagcac atgaggaatc acccatgtgc gactcccaca gtcactgggg 120
agtcttccc 129

<210> SEQ ID NO 9
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 9
attgactggt tggtgagaga agagttttag agctatgctg ttttgttttt tttgcaa 57

<210> SEQ ID NO 10
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 10
attgaaacag catagcaagt taaaataagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 11
<211> LENGTH: 107
<212> TYPE: DNA
<213> ORGANISM: Artificial Sequence
<220> FEATURE:
<223> OTHER INFORMATION: Synthetic polynucleotide

<400> SEQUENCE: 11
attgttttag agctatgctg ttttgaatgg tcccaaaacg actggttggt gagagaagag 60
ttttagagct atgctgtttt gaatggtccc aaaacttttt tttgcaa 107

<210> SEQ ID NO 12
<211> LENGTH: 154
<212> TYPE: DNA
<213> ORGANISM: Artificial Sequence
<220> FEATURE:
<223> OTHER INFORMATION: Synthetic polynucleotide

<400> SEQUENCE: 12
attgttggaa ccattcaaaa cagcatagca agttaaaata aggctagtcc gttatcaact 60
tgaaaaagtg gcaccgagtc ggtgcgggag cacatgagga atcacccatg tgcgactccc 120
acagtcactg gggagtcttc cctttttttt gcaa 154

<210> SEQ ID NO 13
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 13
attgactggt tggtgagaga agagtagacg agctatgctg ttttgttttt tttgcaa 57

<210> SEQ ID NO 14
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 14
attgaaacag catagcaagt gtctataagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 15
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 15
attgactggt tggtgagaga agagaaaacg agctatgctg ttttgttttt tttgcaa 57

<210> SEQ ID NO 16
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 16
attgaaacag catagcaagt gtttttaagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 17
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 17
attgactggt tggtgagaga agagatttag agctatgctg ttttgttttt tttgcaa 57

<210> SEQ ID NO 18
<211> LENGTH: 141
<212> TYPE: DNA
<213> ORGANISM: Artificial Sequence
<220> FEATURE:

<223> OTHER INFORMATION: Synthetic polynucleotide

<400> SEQUENCE: 18
attgaaacag catagcaagt taaattaagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 19
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 19
attgactggt tggtgagaga agagaatacg agctatgctg ttttgttttt tttgcaa 57

<210> SEQ ID NO 20
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 20
attgaaacag catagcaagt gtatttaagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 21
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 21
attgatgaaa ttaggatcat gtagaaaacg agctatgctg ttttgttttt tttgcaa 57

<210> SEQ ID NO 22
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 22
attgactggt tggtgagaga agagttttag acgatacgac aaatgttttt tttgcaa 57

<210> SEQ ID NO 23
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 23
attgtttgtc gtatcgaagt taaaataagg ctagtccgtt atcaacttga aaaagtggca 60
ccgagtcggt gcgggagcac atgaggaatc acccatgtgc gactcccaca gtcactgggg 120
agtcttccct tttttttgca a 141

<210> SEQ ID NO 24
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 24
cgtcgactgg ttggtgagag aagagtttta gagctatgct gttttgtttt ggcc 54

<210> SEQ ID NO 25
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 25
ccatccagtc ctgatgagtc cgtgaggacg aaacgagtaa gctcgtc 47

<210> SEQ ID NO 26
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 26
ggccggcatg gtcccagcct cctcgctggc gccggctggg caacatgctt cggcatggcg 60
aatgggacgc tt 72

<210> SEQ ID NO 27
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 27
tgcagactgg ttggtgagag aagagtttta gagctatgct gttttgtttt aaca 54

<210> SEQ ID NO 28
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 28
ccataacaaa gcaccagtgg tctagtggta gaatagtacc ctgccacggt acagacccgg 60
gttcgattcc cggctggtgc a 81

<210> SEQ ID NO 29
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 29
aacaaagcac cagtggtcta gtggtagaat agtaccctgc cacggtacag acccgggttc 60
gattcccggc tggtgcagct t 81

<210> SEQ ID NO 30

-continued

```
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 30

attgactggt tggtgagaga agagtctttg tactctggta ccagaagcta caaagataag     60

gcttcatgcc gaaatcaaca ccctgtcatt ttatggcagg gtggggagca catgaggaat    120

cacccatgtg cgactcccac agtcactggg gagtcttccc tttttttgc aa             172
```

CrRNA:tracrRNA-BASED BINARY LOGIC GATE DESIGN AS A TOOL FOR SYNTHETIC BIOLOGY

STATEMENT OF GOVERNMENT SUPPORT

This invention was made with government support under grant number IOS1750006 awarded by the National Science Foundation. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5051.970.WO_ST25.txt, 8453 bytes in size, generated on Dec. 5, 2020 and filed via EFS-Web, is provided in lieu of a paper copy. This Sequence Listing is hereby incorporated herein by reference into the specification for its disclosures.

STATEMENT OF PRIORITY

This application claims the benefit, under 35 U.S.C. § 119 (e), of U.S. Provisional Application No. 62/947,277 filed on Dec. 12, 2019, the entire contents of which is incorporated by reference herein.

FIELD OF THE INVENTION

The invention relates to logic-gate-based Type II or Type V CRISPR-Cas constructs and methods for modifying gene expression using the CRISPR-Cas constructs and CRISPR-Cas effector proteins.

BACKGROUND OF THE INVENTION

The ability to control gene expression in a tissue specific manner is desirable. The present invention provides new compositions and methods for their use in modifying complex gene expression patterns to generate new and more precise patterns of gene expression.

SUMMARY OF THE INVENTION

One aspect of the invention comprises a logic-gate-based system for modifying (altering, controlling) gene expression or modifying a genome, the system comprising: (A) at least one orthogonal (or independent) pair of hybridizing synthetic nucleic acid constructs, each of the at least one orthogonal pairs comprising (i) a CRISPR nucleic acid (e.g., crRNA, crDNA) construct comprising a repeat sequence and at least one spacer sequence having substantial complementarity to a target nucleic acid, the CRISPR nucleic acid operably linked to a first promoter and (ii) a trans-activating CRISPR (tracr) nucleic acid (e.g., tracrRNA, tracrDNA) construct comprising a sequence that is complementary to the repeat sequence of the CRISPR nucleic acid of the same orthogonal pair of hybridizing synthetic nucleic acid constructs, the tracr nucleic acid operably linked to a second promoter, which when both (i) and (ii) are (concurrently) expressed in a cell, a synthetic CRISPR nucleic acid-tracr nucleic acid (crRNA-tracrRNA) hybrid is formed having a secondary structure comprising a lower stem, and optionally, an upper stem and which hybrid forms a complex with a Type II or Type V CRISPR-Cas effector protein (e.g., Type II or Type V CRISPR-Cas nuclease (e.g., active HNH and RuvC or RuvC (RuvC-like)), deactivated Type II or Type V CRISPR-Cas effector protein (dCRISPR-Cas effector protein (e.g., dCas9, dCas12b), e.g., inactive HNH and inactive RuvC, or inactive RuvC); or Type II or Type V CRISPR-Cas nickase (nCRISPR-Cas effector protein (e.g., Cas9n, cas12bn), e.g., inactive HNH or inactive RuvC)), and (B) at least one nucleic acid operably linked to a third promoter and encoding a Type II or Type V CRISPR-Cas effector protein (e.g., Cas9, dCas9, Cas9n; Cas12b, dCas12b, Cas12bn), that forms a complex with at least one synthetic CRISPR nucleic acid-tracr nucleic acid hybrid formed by the at least one orthogonal pair of hybridizing nucleic acid constructs; wherein the CRISPR nucleic acid of each orthogonal pair of hybridizing synthetic nucleic acid constructs and a tracr nucleic acid of any other of the at least one orthogonal pairs of hybridizing synthetic nucleic acid constructs comprise at least one non-natural mismatch (e.g., 1, 2, 3, 4, 5, 6, 7, 8, 9, 10 or more mismatches) between the repeat sequence of the CRISPR nucleic acid of each orthogonal pair of hybridizing synthetic nucleic acid constructs and the sequence that is complementary to the repeat sequence of the CRISPR nucleic acid of a tracr nucleic acid of any other of the at least one orthogonal pairs of hybridizing synthetic nucleic acid.

A second aspect provides a pair of hybridizing nucleic acid constructs, comprising: (A) a CRISPR nucleic acid (e.g., crRNA, crDNA) construct comprising a repeat sequence and at least one spacer sequence having substantial complementarity to a target nucleic acid; and (B) a trans-activating CRISPR (tracr) nucleic acid (e.g., tracrRNA, tracrDNA) construct comprising a sequence that is complementary to the repeat sequence of the CRISPR nucleic acid of the same orthogonal pair of hybridizing synthetic nucleic acid constructs, which when both (A) and (B) are expressed in a cell, a synthetic CRISPR nucleic acid-tracr nucleic acid (e.g., crRNA-tracrRNA) hybrid is formed, wherein the synthetic CRISPR nucleic acid-tracr nucleic acid hybrid comprises a lower stem and/or optionally, an upper stem, and the lower stem, and/or when present, the upper stem, comprise at least one nucleotide modification (e.g., 1, 2, 3, 4, 5, 6, or 7 or more nucleotide modifications, optionally at least one base pair modification) as compared to a lower stem and/or an upper stem of a wild type (Type II or Type V) CRISPR nucleic acid-tracr nucleic acid hybrid corresponding to the synthetic CRISPR nucleic acid-tracr nucleic acid hybrid.

Additional aspects provide methods for modifying the expression of at least one gene in a cell or modifying a genome of a cell, comprising introducing into the cell at least one pair of hybridizing nucleic acid constructs and a Type II or Type V CRISPR-Cas effector protein, or a nucleic acid construct encoding a Type II or a Type V CRISPR-Cas effector protein, wherein the Type II or Type V CRISPR-Cas effector protein forms a complex with the synthetic CRISPR nucleic acid-tracr nucleic acid hybrid formed by the at least one pair of hybridizing synthetic nucleic acid constructs, thereby modifying the expression of the at least one gene in the cell or modifying the genome of the cell.

Additionally provided herein are cells and organisms comprising the logic gate systems of the invention, and/or comprising the at least one pair or at least two pairs of hybridizing nucleic acid constructs of the present invention These and other aspects of the invention are set forth in more detail in the description of the invention below.

DETAILED DESCRIPTION

Figure 1:
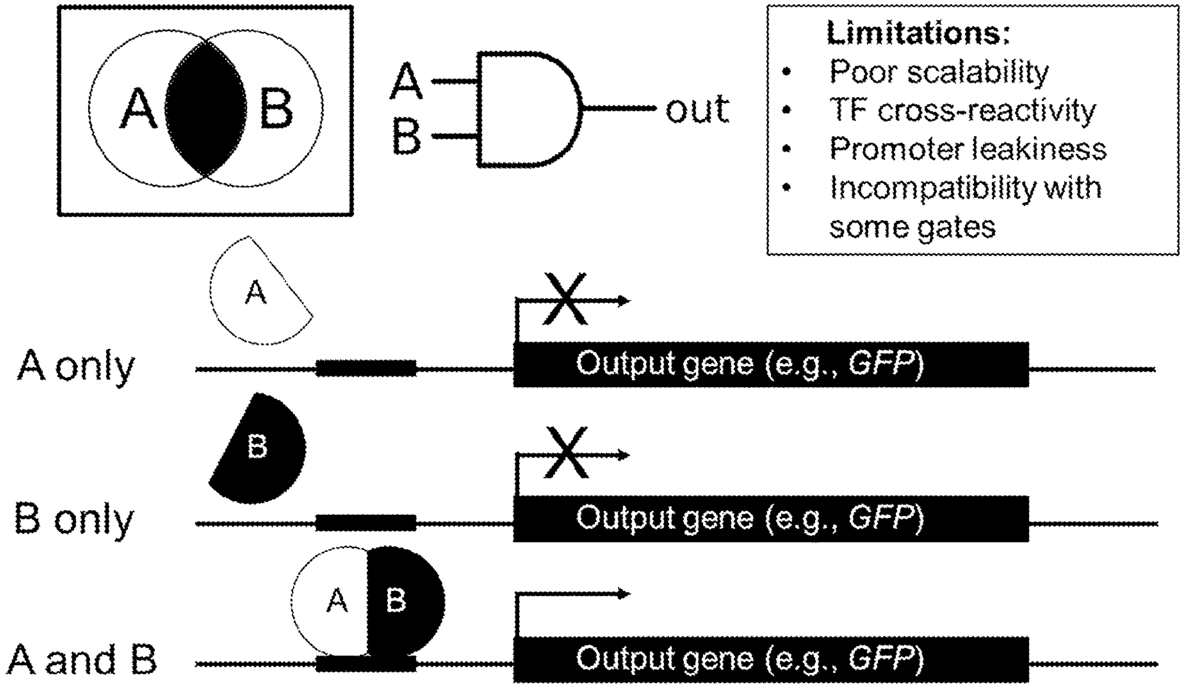
FIG. 1 shows an example of a classical genetic logic gate: the AND gate.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence," "nucleic acid," "nucleic acid molecule," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms "complementary" or "complementarity," as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any value or range therein, complementarity). In some embodiments, substantial complementarity means at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% complementarity, and any value or range therein). In some embodiments, substantial complementarity means at least about 70%, about 75%, about 80%, about 85%, or about 90% complementarity (e.g., about 90%, 91%, 92%, 93%, 94%, 95%, 96%, 97%, 98%, 99%, and/or 100% complementarity).

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments, substantial identity means at least about 90% identical (e.g., about 90%, 91%, 92%, 93%, 94%, 95%, 96%, 97%, 98%, 99%, and/or 100%).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

Any nucleotide sequence and/or heterologous nucleic acid construct of this invention can be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the reference nucleotide sequence but which still encodes a polypeptide having the same function as that encoded by the original, native nucleotide sequence. Thus, in some embodiments of the invention, the nucleotide sequence and/or heterologous nucleic acid construct of this invention can be codon optimized for expression in the particular species of interest. In some embodiments, a Cas9 nuclease may be encoded by a nucleotide sequence that is codon optimized for the organism comprising the target DNA.

In some embodiments, the recombinant nucleic acid molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In some embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the action of a human, they exist apart from their native environment and therefore are not products of nature, however, in some embodiments, they can be introduced into and exist in a recombinant host cell.

In any of the embodiments described herein, the nucleotide sequences and/or recombinant nucleic acid molecules of the invention can be operatively associated with a variety of promoters and other regulatory elements for expression in an organism of interest and/or a cell of an organism of interest. Thus, in representative embodiments, a recombinant nucleic acid of this invention can further comprise one or more promoters operably linked to one or more nucleotide sequences.

By "operably linked" or "operably associated" as used herein, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

As used herein, a "CRISPR-Cas effector protein" can be any CRISPR-Cas endonuclease, its nuclease-dead/deactivated or nickase version, or portion thereof comprising a sequence-specific nucleic acid binding domain (DNA binding domain). A CRISPR-Cas effector protein can be, but is not limited to, a CRISPR-Cas effector protein from a Type II CRISPR-Cas system or a Type V CRISPR-Cas system (e.g., Cas9, Cas12b). In some embodiments, a CRISPR-Cas effector protein may be fused to an accessory protein for carrying out different aspects of this invention. Alternatively, the CRISPR-Cas effector protein and an accessory protein may be designed such that the accessory protein is recruited to the CRISPR-Cas ribonucleoprotein complex. Accordingly, in some embodiments, an accessory protein may be fused to the CRISPR-Cas effector protein or recruited to the CRISPR-Cas ribonucleoprotein complex. An accessory protein may be any protein that can be associated with a CRISPR-Cas effector protein including, but not limited to, a transcriptional activator, a transcriptional repressor, a chromatin remodeling factor, a histone or DNA modification enzyme, a base editor, a fluorescent protein (e.g., a marker protein), and/or a reverse transcriptase.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art.

The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Example promoters useful with this invention can include, but are not limited to, RNA Polymerase II promoters CaMV 35S, AtWOX5, SlWOX5, 10xEBSp (synthetic promoter consisting of 10 copies of the DNA binding site of the EIN3 master transcriptional regulator of the ethylene response fused to the minimum 35S promoter), SlDFR, and/or AtRCH p and an RNA Polymerase III promoter AtU6.

In some embodiments, a recombinant nucleic acid molecule of the invention can be an "expression cassette" or can be comprised within an expression cassette. As used herein, "expression cassette" means a recombinant nucleic acid molecule comprising a nucleotide sequence of interest (e.g., the nucleotide sequences of the invention), wherein said nucleotide sequence is operably associated with at least a control sequence (e.g., a promoter). Thus, some embodiments of the invention provide expression cassettes designed to express the nucleotides sequences of the invention.

An expression cassette comprising a nucleotide sequence of interest may be chimeric, meaning that at least one of its components is heterologous or recombinant (non-naturally occurring) with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond a heterologous nucleotide sequence of interest and correct mRNA polyadenylation. The termination region may be native to the transcriptional initiation region, may be native to the operably linked nucleotide sequence of interest, may be native to the host cell, or may be from another source (i.e., foreign or heterologous to the promoter, to the nucleotide sequence of interest, to the host, or any combination thereof).

An expression cassette of the invention also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an Agrobacterium binary vector in double or single stranded linear or circular form which may or may not be self-transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention and/or expression cassettes can be comprised in vectors as described herein and as known in the art.

As used herein, "contact", contacting", "contacted," and grammatical variations thereof, refers to placing the components of a desired reaction together under conditions suitable for carrying out the desired reaction (e.g., transcriptional control, genome editing, nicking, cleavage, and/or amplifying nucleic acids).

"Introducing," "introduce," "introduced" (and grammatical variations thereof) in the context of a polynucleotide of interest means presenting the nucleotide sequence of interest to the host organism or cell of said organism (e.g., host cell) in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides can be introduced into a host cell in a single transformation event, in separate transformation events, or, for example, they can be incorporated into an organism by conventional breeding protocols.

The term "transformation" as used herein refers to the introduction of a heterologous nucleic acid into a cell. Transformation of a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast or mitochondrial genome. Stable transformation as used herein can also refer to a transgene that is maintained extrachromosomally, for example, as a minichromosome or a plasmid.

Accordingly, in some embodiments, a target nucleic acid may be introduced and as such, a system as described herein may further comprise an introduced target nucleic acid as a component.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, the nucleotide sequences, constructs, expression cassettes (e.g., comprising the logic gate systems and pairs of hybridizing nucleic acid constructs) can be expressed transiently and/or they can be stably incorporated into the genome of the host organism. The logic gate system and pairs of hybridizing nucleic acid constructs may be introduced into the genome of a cell in a tissue specific, cell type specific, and precise manner through, for example, homologous recombination.

A recombinant nucleic acid molecule/polynucleotide of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid molecule/polynucleotide of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events, or, alternatively, where relevant, a nucleotide sequence can be incorporated into a plant, for example, as part of a breeding protocol.

In some embodiments, the heterologous or recombinant nucleic acid constructs of the invention are "synthetic." A "synthetic" nucleic acid molecule, a "synthetic" nucleotide sequence or a "synthetic" polypeptide is a nucleic acid molecule, nucleotide sequence or polypeptide that is not found in nature but is created by a human hand and is therefore not a product of nature.

Type II CRISPR-Cas systems comprise three subtypes: Type II-A, Type II-B and Type II-C, each of which comprise the multidomain protein, Cas9, in addition to the adaptation polypeptides, Cas1, Cas2 and optionally, Csn2 and/or Cas4. Most Type II loci also encode a tracrRNA. Organisms comprising exemplary Type II CRISPR-Cas systems include, but are not limited to, *Legionella pneumophila, Streptococcus thermophilus, Streptococcus pyogenes* and *Neisseria lactamica*, optionally *Legionella pneumophila* str. Paris, *Streptococcus thermophilus* CNRZ1066 and *Neisseria lactamica* 020-06.

CRISPR-Cas systems and groupings of Cas9 nucleases are well known in the art and include, for example, a *Streptococcus thermophilus* CRISPR 1 (Sth CR1) group of Cas9 nucleases, a *Streptococcus thermophilus* CRISPR 3 (Sth CR3) group of Cas9 nucleases, a *Lactobacillus buchneri* CD034 (Lb) group of Cas9 nucleases, and a *Lactobacillus rhamnosus* GG (Lrh) group of Cas9 nucleases. Additional Cas9 nucleases include, but are not limited to, those of *Lactobacillus curvatus* CRL 705. Still further Cas9 nucleases useful with this invention include, but are not limited to, a Cas9 from *Lactobacillus animalis* KCTC 3501, and *Lactobacillus farciminis* WP 010018949.1.

Thus, as used herein, "Cas9 nuclease" refers to a large group of endonucleases that catalyze the double stranded DNA cleavage in the CRISPR Cas system. These polypeptides are well known in the art and many of their structures (sequences) are characterized (See, e.g., WO2013/176772; WO/2013/188638). The domains for catalyzing the cleavage of the double stranded DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)). Cas9 nucleases useful with the present invention include active Cas9 having intact HNH and RuvC motifs, as well as nuclease dead Cas9 (dCas9) in which both the HNH and RuvC motifs are mutated and inactive, and a nickase Cas9 (Cas9n) in which one or the other of the HNH motif or the RuvC motif is inactivated. A Cas9 nuclease useful with this invention may be obtained from any wild type Type II CRISPR-Cas system.

In some embodiments, the invention may comprise a functional fragment of a Cas9 polypeptide. A Cas9 functional fragment retains one or more of the activities of a native Cas9 polypeptide including, but not limited to, HNH nuclease activity, RuvC nuclease activity, DNA, RNA and/or PAM recognition and binding activities. A functional fragment of a Cas9 nuclease may be encoded by a fragment of a Cas9 polynucleotide.

Type V CRISPR-Cas systems also comprise multiple subtypes including some of which utilize a dual guide mechanism involving a CRISPR nucleic acid and a tracr nucleic acid such as subtype B, C, E, F, and G. In some embodiments, a CRISPR-Cas system useful with this invention can be Type V-B CRISPR-Cas system. In some embodiments, the Type V-B CRISPR-Cas system can be Cas12b.

In some embodiments, the invention may comprise a functional fragment of a Cas12b nuclease. A Cas12b functional fragment retains one or more of the activities of a native Cas12b nuclease including, but not limited to, RuvC nuclease activity, DNA, RNA and/or PAM recognition and binding activities. A functional fragment of a Cas12b nuclease may be encoded by a fragment of a Cas12b polynucleotide. Cas12b nucleases useful with the present invention include active Cas12b having an intact RuvC motif, as well as nuclease dead Cas12b (dCas12b) in which the RuvC motif is mutated and inactive. A Cas12b polypeptide useful with this invention may be obtained from any wild type Type V-B CRISPR-Cas12b system.

The term "genome" as used herein includes an organism's chromosomal/nuclear genome as well as any mitochondrial, chloroplast, and/or plasmid genome.

A "hairpin sequence" as used herein, is a nucleotide sequence comprising hairpins (e.g., that forms one or more hairpin structures). A hairpin (e.g., stem-loop, fold-back) refers to a nucleic acid molecule having a secondary structure that includes a region of complementary nucleotides that form a double strand that are further flanked on either side by single stranded-regions. Such structures are well known in the art. As known in the art, the double stranded region can comprise some mismatches in base pairing or can be perfectly complementary. In some embodiments of the present disclosure, a hairpin sequence of a nucleic acid construct can be located at the 3' end of a tracr nucleic acid.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences, CRISPR repeat-spacer-repeat sequences, and/or CRISPR arrays.

A "repeat sequence" as used herein refers, for example, to any repeat sequence of a wild-type Type II CRISPR-Cas system, a wild-type Type V CRISPR-Cas system, or a repeat sequence of a synthetic CRISPR array, which are separated by "spacer sequences" (e.g., a repeat-spacer sequence or a repeat-spacer-repeat sequence of the invention). A repeat sequence useful with this invention can be any known or later identified repeat sequence of a Type II or Type V CRISPR locus. Accordingly, in some embodiments, a repeat-spacer sequence or a repeat-spacer-repeat comprises a repeat that is substantially identical (e.g. at least about 70% identical (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a repeat from CRISPR array of a wild-type Type II CRISPR-Cas system or a wild-type Type V CRISPR-Cas system. In additional embodiments, a repeat sequence useful with this invention can comprise a nucleotide sequence comprising a partial repeat that is a fragment or portion of consecutive nucleotides of a repeat sequence of a CRISPR array wild-type Type II CRISPR-Cas system or a wild-type Type V CRISPR-Cas system.

As used herein, "CRISPR array" of a Type II CRISPR-Cas system or a Type V CRISPR-Cas system refers to a nucleic acid construct that comprises from 5' to 3' a repeat-spacer-repeat sequence or comprises from 5' to 3' at least one repeat-spacer sequence (e.g., about 1, 2, 3, 4, 5, 6, 7, 8, 9, 10, 11, 12, 13, 14, 15, 16, 17, 18, 19, 20, 21, 22, 23, 24, or 25 repeat-spacer sequences, and any range or value therein). When more than one repeat-spacer is comprised in a CRISPR array, the spacer of the prior (5' to 3') repeat-spacer sequence can be linked to the repeat of the following repeat-spacer (e.g., the spacer of a first repeat-spacer sequence is linked to the repeat of a second repeat-spacer sequence). In some embodiments, a CRISPR array can comprise two repeats (or two partial repeats) separated by a spacer (e.g., a repeat-spacer-repeat sequence).

Any wild type Type II CRISPR-Cas system and components thereof (e.g., Cas9 polypeptide, crRNA, tracrRNA, repeats) may be useful with the present invention. Example wild type Type II CRISPR-Cas systems may include, but are not limited to, a wild type Type II CRISPR-Cas system from *Streptococcus* spp., *Lactobacillus* spp., *Staphylococcus* spp., *Bifidobacterium* spp., *Corynebacterium* spp., *Oenococcus* spp., *Enterococcus* spp., *Mycoplasma* spp., *Campylobacter* spp., *Francisella* spp., *Helicobacter* spp., *Listeria* spp., *Neisseria* spp., *Kandleria* spp., *Leuconostoc* spp., *Pediococcus* spp., *Weissella* spp., or *Olsenella* spp.

In some embodiments, an example wild type Type II CRISPR-Cas system may include, but are not limited to, a wild type Type II CRISPR-Cas system from *Mycoplasma* gallisepticum, *Mycoplasma canis* PG14, *Mycoplasma synoviae* 53, *Bifidobacterium bombi, Bifidobacterium dentium* LMG 11045, *Bifidobacterium merycicum* LMG 11341, *Campylobacter jejuni, Staphylococcus pseudointermedius* ED99, *Staphylococcus lugdensis* M23590, *Enterococcus faecalis* TX0012, *Corynebacterium diphtheriae, Francisella novicida* U112, *Kandleria vitulina* DSM 20405, *Neisseria meningitidis* Z2491, *Helicobacter mustelae, Listeria innocua, Lactobacillus agilis* DSM 20509, *Lactobacillus animalis* DSM 20602, *Lactobacillus apodemi* DSM 16634, *Lactobacillus brevis subsp gravensis* ATCC 27305, *Lactobacillus buchneri* CD034, *Lactobacillus buchneri* DSM 20057, *Lactobacillus* cacaonum DSM 21116, *Lactobacillus casei* str Zhang, *Lactobacillus ceti* DSM 22408, *Lactobacillus coryniformis subsp coryniformis* KCTC 3167, *Lactobacillus coryniformis torquens, Lactobacillus crispatus* FB049-03, *Lactobacillus curvatus* CRL 705, *Lactobacillus delbrueckii* subsp *lactis* CRL 581, *Lactobacillus delbrueckii jakobsenii* DSM 26046, *Lactobacillus diolivorans* DSM 14421, *Lactobacillus farciminis* DSM 20184, *Lactobacillus fermentum* DSM 20055, *Lactobacillus floricola* DSM 23037A, *Lactobacillus floricola* DSM 23037B, *Lactobacillus fuchuensis* DSM 14340, *Lactobacillus futsaii* JCM 17355, *Lactobacillus gasseri* K7, *Lactobacillus graminis* DSM 20719, *Lactobacillus hammesii* DSM 16381, *Lactobacillus hominis* CRBIP, *Lactobacillus hordei* DSM 19519A, *Lactobacillus hordei* DSM 19519B, *Lactobacillus jensenii* DSM 20557, *Lactobacillus johnsonii* DPC 6026, *Lactobacillus lindneri* DSM 20690, *Lactobacillus mali* ATCC 27304, *Lactobacillus mindensis* DSM 14500, *Lactobacillus mucosae* DSM 13345, *Lactobacillus namurensis* DSM 19117, *Lactobacillus nantensis* DSM 16982, *Lactobacillus nodensis* DSM 19682A, *Lactobacillus nodensis* DSM 19682B, *Lactobacillus oligofermentans* DSM 15707, *Lactobacillus otakiensis* DSM 19908, *Lactobacillus ozensis* DSM 23829, *Lactobacillus paracasei* subsp *paracasei* 8700:2, *Lactobacillus paracasei* subsp *tolerans* Lp17, *Lactobacillus paracollinoides* DSM 15502, *Lactobacillus parakefiri* DSM 10551, *Lactobacillus pentosus* KCA1, *Lactobacillus pentosus* IG1, *Lactobacillus plantarum* EGD-AQ4, *Lactobacillus psittaci* DSM 15354, *Lactobacillus rennini* DSM 20253, *Lactobacillus reuteri* m1c3, *Lactobacillus rhamnosus* GG, *Lactobacillus rossiae* DSM 15814, *Lactobacillus ruminis* ATCC 25644, *Lactobacillus sakei carnosus* DSM 15831, *Lactobacillus salivarius* TCC 118, *Lactobacillus sanfranciscensis* DSM 20451, *Lactobacillus saniviri* DSM 24301, *Lactobacillus senmaizukei* DSM 21775, *Lactobacillus tucceti* DSM 20183, *Lactobacillus versmoldensis* DSM 14857, *Lactobacillus zymae* DSM 19395, *Leuconostoc gelidum* JB7, *Leuconostoc pseudomesenteroides* 4882, *Oenococcus kitaharae* DSM 17330, *Pediococcus inopinatus* DSM 20285, *Pediococcus lolii* DSM 19927, *Pediococcus parvulus* DSM 20332A, *Pediococcus parvulus* DSM 20332B, *Pediococcus stilesii* DSM 18001, *Streptococcus agalactiae* GB00300, *Streptococcus gallolyticus* ATCC BAA-2069, *Streptococcus henryi* DSM 19005, *Streptococcus mutans* NLML5, *Streptococcus oralis* SK304, *Streptococcus anginosus* 1_2_62CV, *Streptococcus anginosus* DSM 20563, *Streptococcus* dysagalactiae subsp *equisimilis, Streptococcus equi* subsp *zooepidemicus, Streptococcus gordonii Challis* substr CH1 *Streptococcus infantarius* subsp *infantarius, Streptococcus intermedius* B196, *Streptococcus lutetiensis* 033, *Streptococcus mitis* SK321, *Streptococcus mutans* UA 159, *Streptococcus orisratti* DSM 15617, *Streptococcus parasanguinis* F0449, *Streptococcus salivarius* K12, *Streptococcus sanguinis* SK330, *Streptococcus vestibularis* ATCC 49124, *Streptococcus pyogenes, Streptococcus thermophilus, Lactobacillus composti* DSM 18527, *Lactobacillus concavus* DSM 17758, *Lactobacillus secaliphilus* DSM 17896, *Weissella halotolerans* DSM 20190, *Weissella kandleri* DSM 20593, or *Olsenella uli.*

Any wild type Type V CRISPR-Cas system and components thereof (e.g., Cas12b polypeptide, crRNA, tracrRNA, repeats) may be useful with the present invention. Example wild type Type V CRISPR-Cas systems may include, but are not limited to, a wild type Type V CRISPR-Cas system from *Alicyclobacillus* spp., *Oleophilus* spp. and/or *Deltaproteobacteria* spp. In some embodiments, an example wild type Type V CRISPR-Cas system may include, but are not limited to, a wild type Type V CRISPR-Cas system from *Alicyclobacillus acidoterrestris* or *Deltaproteobacteria* bacterium.

A "spacer sequence" as used herein is a nucleotide sequence that is complementary to a target DNA (i.e., target region in the genome or the "protospacer sequence", which is adjacent to a protospacer adjacent motif (PAM) sequence). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. In some embodiments, the spacer sequence has at least 90% (e.g., at least 90%, 91%, 92%, 93%, 94%, 95%, 96%, 97%, 98%, 99%, or 100%) complementarity to the target DNA. In some embodiments, the spacer sequence has 100% complementarity to the target DNA.

As used herein, a "target DNA," "target region" or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a repeat-spacer sequence or repeat-spacer-repeat sequence. In some embodiments, a target region may be about 10 to about 40 consecutive nucleotides in length located immediately adjacent to a PAM sequence (PAM sequence located immediately 3' of the target region in a Type II CRISPR-Cas system) in the genome of the organism.

In some embodiments, a target region (e.g., target DNA) useful with this invention may be any DNA. In some embodiments, a target region may be located within an essential gene or it may be located in a non-essential gene.

A "trans-activating CRISPR (tracr) nucleic acid" or "tracr nucleic acid" as used herein refers to any tracr RNA (or its encoding DNA). A tracr nucleic acid comprises from 5' to 3' an upper stem, often a bulge, a lower stem, *nexus* hairpins and terminal hairpins. A trans-activating CRISPR (tracr) nucleic acid functions in hybridizing to the repeat portion of mature or immature crRNAs, recruits Cas9 protein to the target site, and may facilitate the catalytic activity of Cas9 by inducting structural rearrangement. The functional composition of tracrRNA molecules is listed above. Sequences for tracrRNAs are specific to the CRISPR-Cas system and can be variable. Any tracr nucleic acid, known or later identified, can be used with this invention. In some embodiments, a tracrRNA useful with this invention may be a wild type tracrRNA or a synthetic tracrRNA, wherein the synthetic tracrRNA comprises at least one non-native nucleotide as compared to a wild type tracrRNA. A tracrRNA useful with this invention may be a "processed" or "pre-processed" tracr of any Type II or Type V CRISPR-Cas system.

As used herein, "at least one orthogonal pair of hybridizing nucleic acid constructs" refers to pairs of hybridizing nucleic constructs that are independent of each other. That is, the hybridizing nucleic acid constructs (crRNA, tracrRNA) of one pair that is fully orthogonal from another pair of hybridizing nucleic acid constructs do not hybridize to the hybridizing nucleic acid constructs of the other pair. Thus, when at least two fully orthogonal pairs of hybridizing nucleic acid constructs are present, the hybridizing nucleic acid constructs (crRNA, tracrRNA) of each pair do not hybridize to the hybridizing nucleic acid constructs of the other pair.

In some embodiments, "at least one orthogonal pair of hybridizing nucleic acid constructs" also refers to pairs of hybridizing nucleic acid constructs in which the orthogonal pairs may hybridize weakly or inefficiently due to mismatches between the crRNA and tracrRNA; that is, there may be sufficient complementarity to allow weak or inefficient cross hybridization between the orthogonal pairs. Such a system in which orthogonal pairs of hybridizing nucleic acid constructs may weakly interact may be used to, for example, fine tune the activity of a CRISPR-Cas effector protein (e.g., nuclease, activation, repression, etc.) against specific targets. For example, using a single crRNA and a series of tracrRNA with different number/position mismatches with the single crRNA and each of the tracrRNA under a different promoter, the expression of the target nucleic acid (e.g., one or more target nucleic acids) may be controlled under different conditions. For example, under conditions under which a promoter 1 driving the expression of the tracrRNA with least complementarity with the single crRNA, the expression of the target nucleic acid would be very low, but when the activity of a promoter 2 driving the expression of a second tracrRNA having good complementarity to the single crRNA is high, the expression of the target nucleic acid will be high. Alternatively, in some embodiments, a single tracRNA may be used along with multiple crRNAs that harbor a variable number of stem mismatches relative to tracrRNA. If each crRNA targets a different gene, then different levels of activation/repression/cutting can be achieved in parallel, even if all crRNAs are driven by the same-strength promoter.

As used herein, a "target nucleic acid" refers to any nucleic acid in a cell or in vitro (in a cell free system) and can be any nucleic acid (e.g., a gene, portion of a gene, a regulatory element of a gene, a synthetic sequence, intergenic sequence, repetitive sequence, etc.) or a portion thereof. In some embodiments, a target nucleic acid can comprise a single target nucleic acid or can comprise two or more nucleic acids. A target nucleic acid may be introduced and incorporated into the genome of the cell (e.g., chromosome, plastid, mitochondria or microchomosome) or it may be introduced into a cell or system and expressed transiently (e.g., on a circular plasmid/episome or a linear molecule). A target nucleic acid may be endogenous or may be heterologous to the cell or cell-free system. As used herein, the term "heterologous" refers to a nucleotide/polypeptide that originates from a foreign species, or, if from the same species, is substantially modified from its native form in composition and/or genomic locus by deliberate human intervention.

"Introducing," "introduce," "introduced" (and grammatical variations thereof) in the context of a polynucleotide of interest means presenting a nucleotide sequence of interest to a cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear, the mitochondrial, and the plastid genome, and therefore includes integration of the nucleic acid into, for example, the chloroplast or mitochondrial genome. Stable transformation as used herein can also refer to a transgene that is maintained extrachromosomally, for example, as a minichromosome or a replicating plasmid.

Accordingly, in some embodiments, a target nucleic acid may be introduced and as such, a system as described herein may further comprise an introduced target nucleic acid as a component.

In some embodiments, "hybridizing weakly" or "hybridizing inefficiently" when used in reference to a crRNA and a tracrRNA pair means a reduced hybridization of at least about 20% to about 99% (e.g, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% reduced, and any value or range therein) as compared to a crRNA and a tracrRNA pair that do not comprise mismatches when hybridized.

Figure 2:
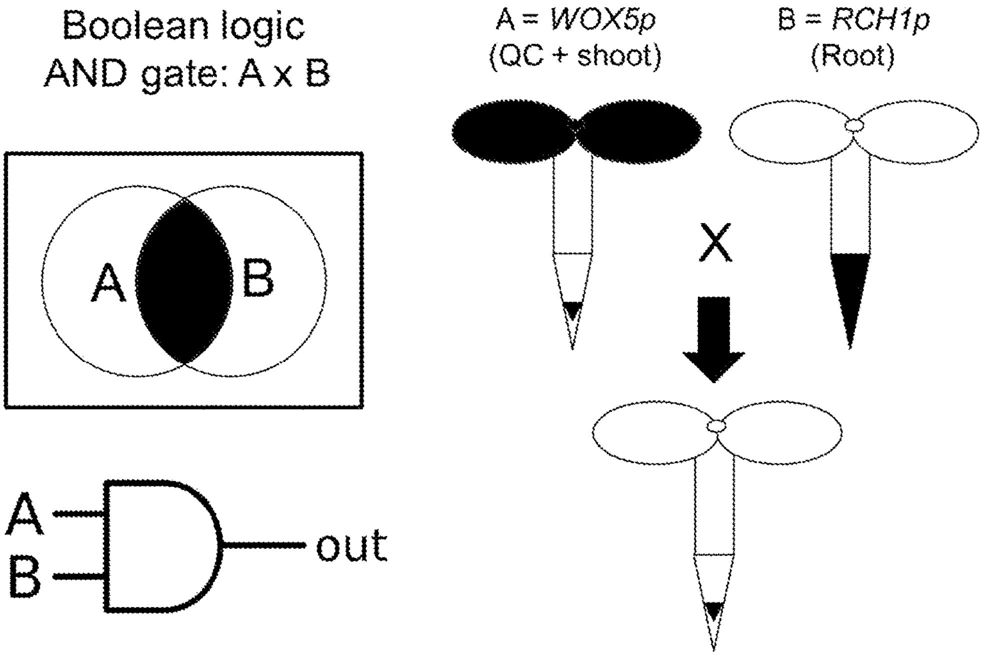
FIG. 2 shows an example of the logic gate system of the present invention. As shown, for example, one can restrict expression of a gene of interest if conditions A and B are met using the so-called logic AND gate. Here, the gene of interest will only be expressed in tissues where both A and B drivers are active. If A is a root-quiescent center (QC)-enriched marker WOX5p with leaky shoot expression and B is a root-specific driver such as RCH1p, then the activity of the output gene should be restricted only to the root QC using a Boolean AND logic gate.
Figure 3:
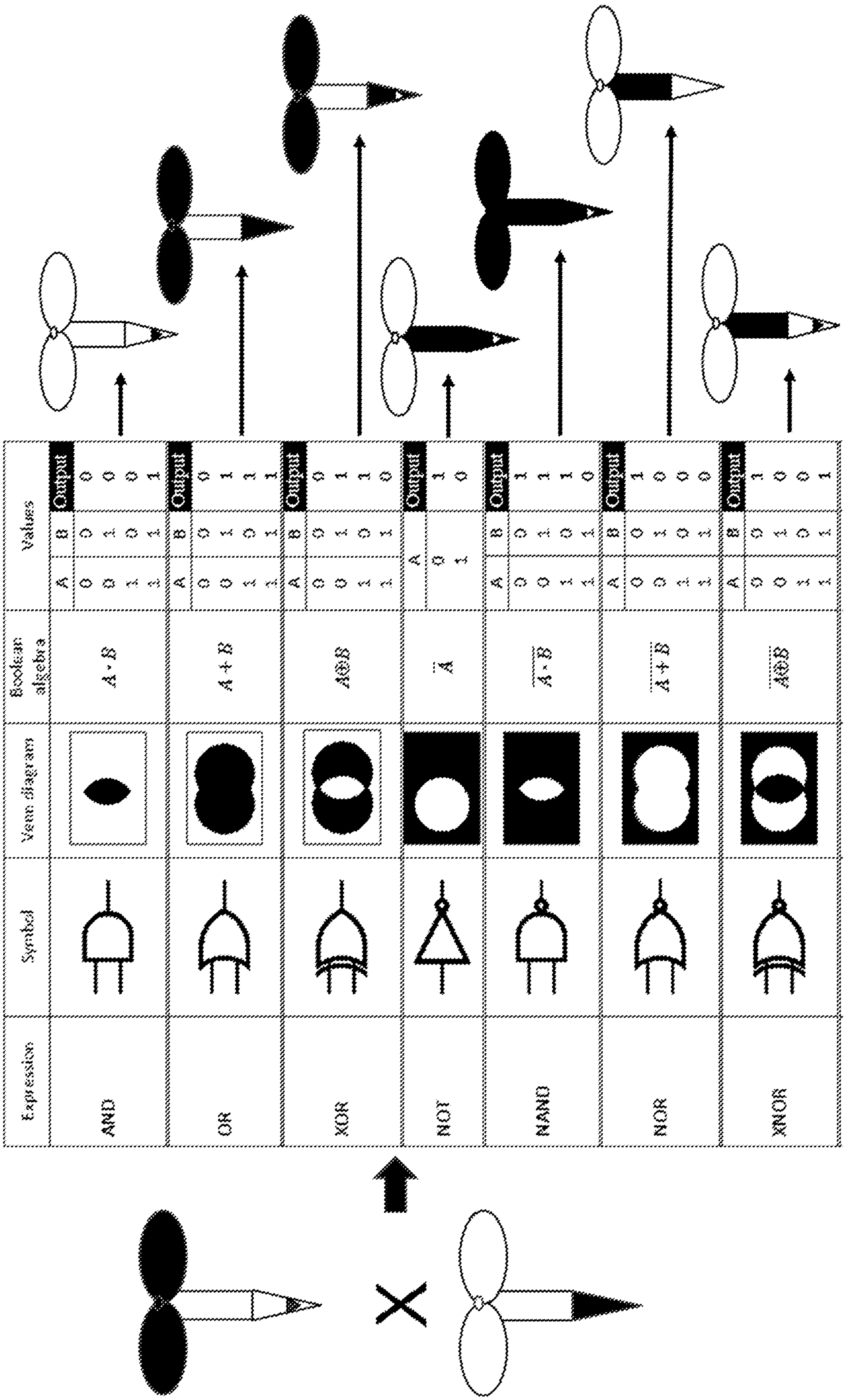
FIG. 3 shows that many other derived patterns of expression are obtainable using other types of basic logic gates provided by the logic gate system of the present invention.

Synthetic genetic circuits are man-made gene expression control mechanisms that enable scientists to manipulate the endogenous gene expression programs in a living cell. By plugging in synthetic pathways and/or genetic devices, the cell can be reprogramed to perform novel or enhanced functions, such as, for example, produce one or more biomolecules of interest (e.g., nucleic acids, proteins, lipids, sugars, or other metabolites), sense and respond to specific stimuli (e.g., biosensors for anthrax, TNT, or metabolite levels), break down polymers (e.g., digest cellulose), degrade and detoxify harmful chemicals/pollutants (e.g., remediate oil spills or heavy metal pollution), kill pathogenic cells (e.g., cancer cells) and much more. Synthetic circuits of this invention are generated using a combination of chemical DNA synthesis and classical molecular biology tools following the design principles of basic electronic devices that rely on modularity, reusability and predictable behavior. One property of these synthetic molecular circuits is that they are able to "interpret" complex input signals and "react" accordingly. To achieve this, logic gates analogous to those used in electronics are used to generate desired patterns and levels of activity of the circuit functional outputs, i.e. to precisely control gene expression in response to specific signal combinations. Basic logic gates YES, NOT, AND, NAND, OR, NOR, XOR, and XNOR (FIG. 1, FIG. 2 and FIG. 3) are used individually or in combinations to confer when and where a selected set of genes of interest is active. For example, in an AND gate (FIG. 1, FIG. 2 and FIG. 3), an output reporter gene/pathway will only be expressed if both input genes A and B are "on", whereas in an XOR gate the output reporter will be expressed only where either A or B are active, but it will be turned off if neither or both A and B are "on" (FIG. 3).

Over the years, numerous versions of the genetic control mechanisms that recapitulate individual basic logic gates have been reported, with some of the genetic devices successfully connecting a limited number of logic gates to perform more complex functions (or in engineering terms, computations) with several inputs and outputs. However, in contrast with true electronic devices that can reuse a small number of identical logic gates in thousands of different positions of a complex electronic circuit, the reusability of the individual genetic elements in a biological circuit is very limited and the connectivity or "wiring" of these elements into one coherent device is exceptionally challenging. The reason for that is that each connection has to be represented by a different biochemical activity that needs to have no crosstalk with any of the unintended elements in the circuit. Thus, one of the challenges synthetic biology faces is to develop a scalable system that would enable the combination of multiple genetic cis-elements that communicate to one another via highly specific trans-factors that only function as intended and show zero cross-reactivity with other elements in the circuit.

Figure 4:
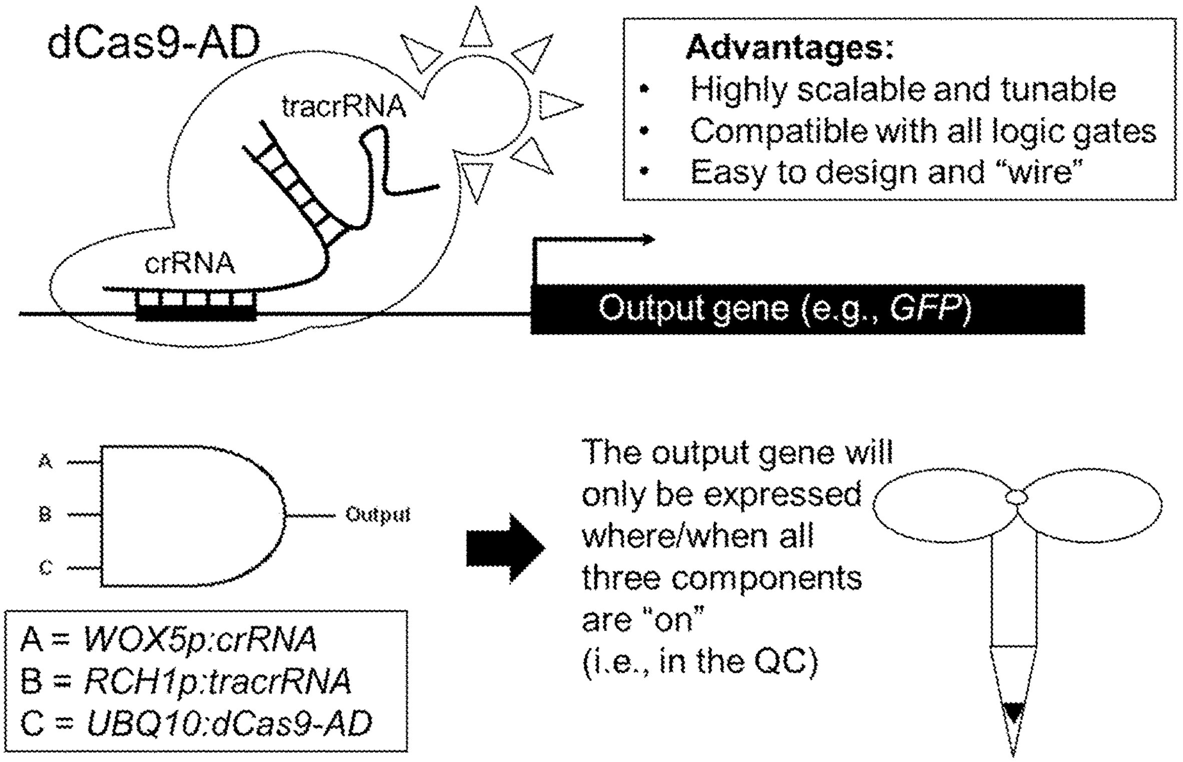
FIG. 4 provides an exemplary CRISPR-based AND gate. The system is based on crRNA and tracrRNA as the A and B inputs that hybridize to one another to form a dual guide RNA. They will assemble with a nuclease-dead or -deactivated CRISPR nuclease (e.g., dCas9, dCas12b) that is converted to a transcription factor (TF) through being fused to a transcriptional activation domain. If crRNA is driven by a QC-enriched WOX5p, tracrRNA is driven by a root-specific promoter RCH1p, and dCas9 TF is expressed constitutively from a constitutive UBQ10 promoter, the output gene will only be expressed in the QC.
Figure 5:
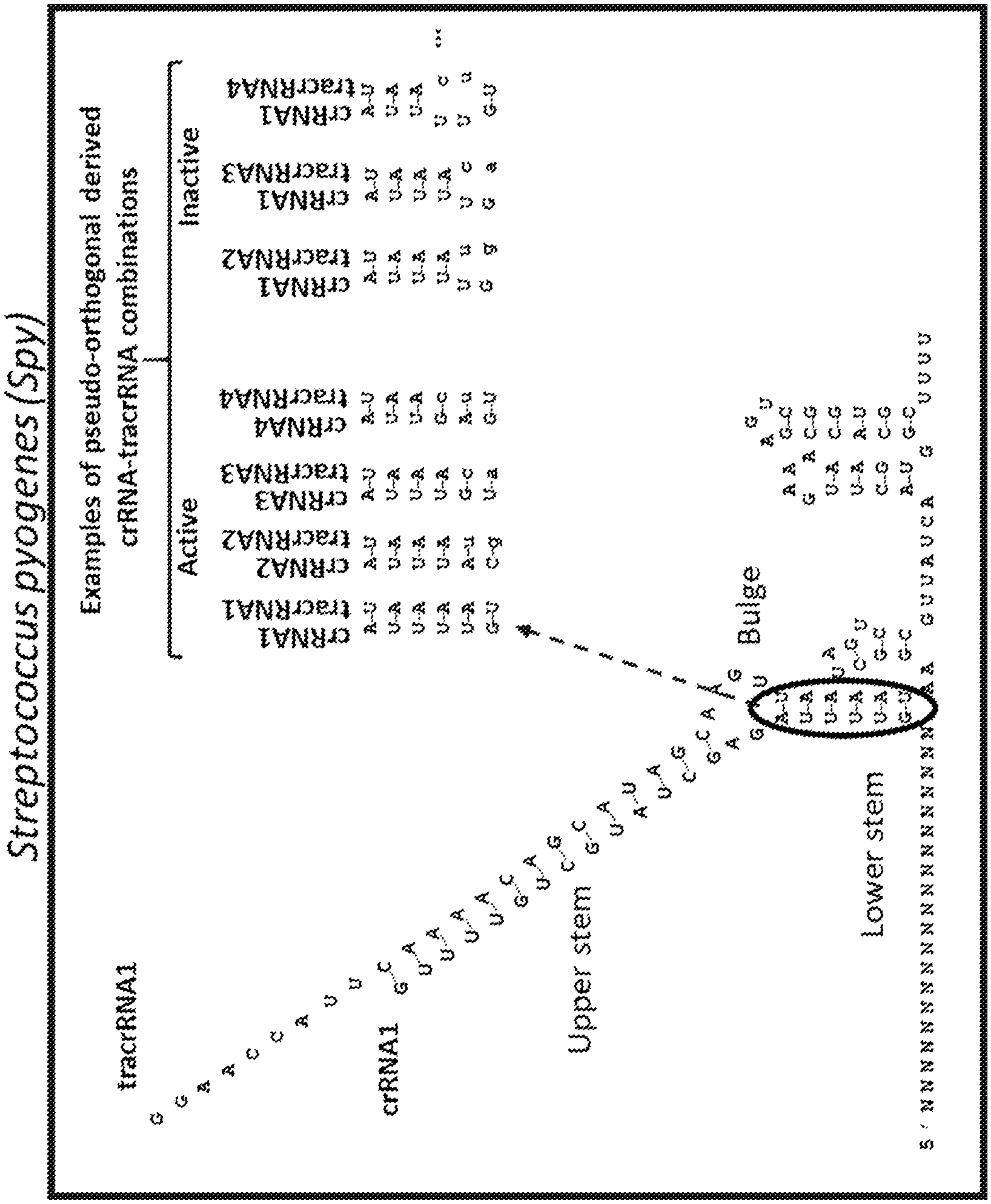
FIG. 5 demonstrates the scalability of the CRISPR-base logic gate system of the invention. For the functional dual guide RNA/Cas effector protein ribonucleoprotein (RNP) complex to form, the crRNA and tracrRNA need to base-pair to one another. Disruption of base-pairing through mutations in the lower stem of the paired region of guide RNA abolishes Cas9 activity, whereas restoration of base pairing via complementary mutations restores Cas9 activity. This base-pairing requirement can be used to generate multiple pseudo-orthogonal (i.e. non-cross-reacting) crRNA-tracrRNA pairs that can work in parallel in the same cell with, for example, the same Cas9 on different DNA targets. That would permit co-existence of independent individual logic gates or of a single multi-gate genetic circuit in the same cell. crRNA1 (SEQ ID NO:1); tracrRNA1 (SEQ ID NO:2).

Several approaches have been used previously to integrate molecular inputs in the form of transcriptional activation. These methods have relied on the functional complementarity of two parts of a split transcription factor (such as the Gal4 DNA binding domain and the GAL4 activation domain) with each part driven by a different promoter. Thus, only when the two parts of the transcription factor are expressed at the same time in the same cell, the expression of the target nucleic acid regulated by this split transcription factor would be activated. This approach has many limitations, the main one being that thus far only a handful of well-characterized natural or engineered (such as TALEN) transcription factors have been proven suitable for this type of experimental approach. Another strategy to achieve this type of signal integration has been also achieved by using a promoter to drive the expression of a single guide RNA and another promoter to drive the dCas9 protein. Thus, only when both promoters are active, the dCas9 targets would be activated/repressed. In contrast, the system of the present invention is based on the use of two RNAs instead of two proteins or a protein and an RNA to serve as signal integrators (FIG. 4). The advantage of the proposed crRNA-tracrRNA system is that not only does it allow for the design of molecular signal integrators, but also to generate large numbers of orthogonal devices (FIGS. 5, 9A and 9B), and thus, large molecular circuits capable of refined logic operations and thus, refined and precise expression patterns.

Figure 6:
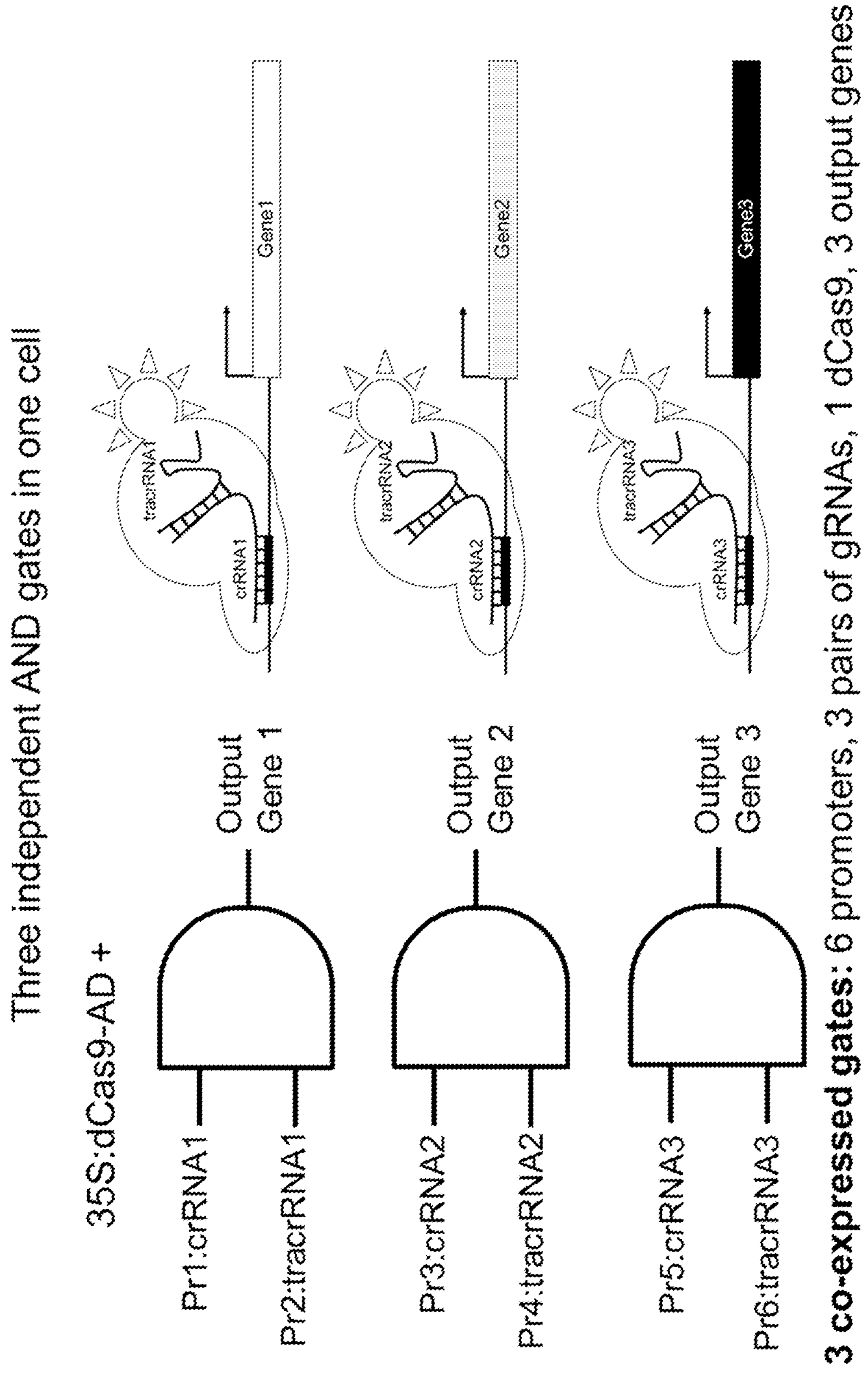
FIG. 6 provides a further example of the scalability of the CRISPR-base logic gate system of the invention. Here, three co-expressed pseudo-orthogonal AND gates collect the input of six different promoters of interest driving three pairs of guide RNAs to independently control three different genes through a single dCas9.
Figure 7:
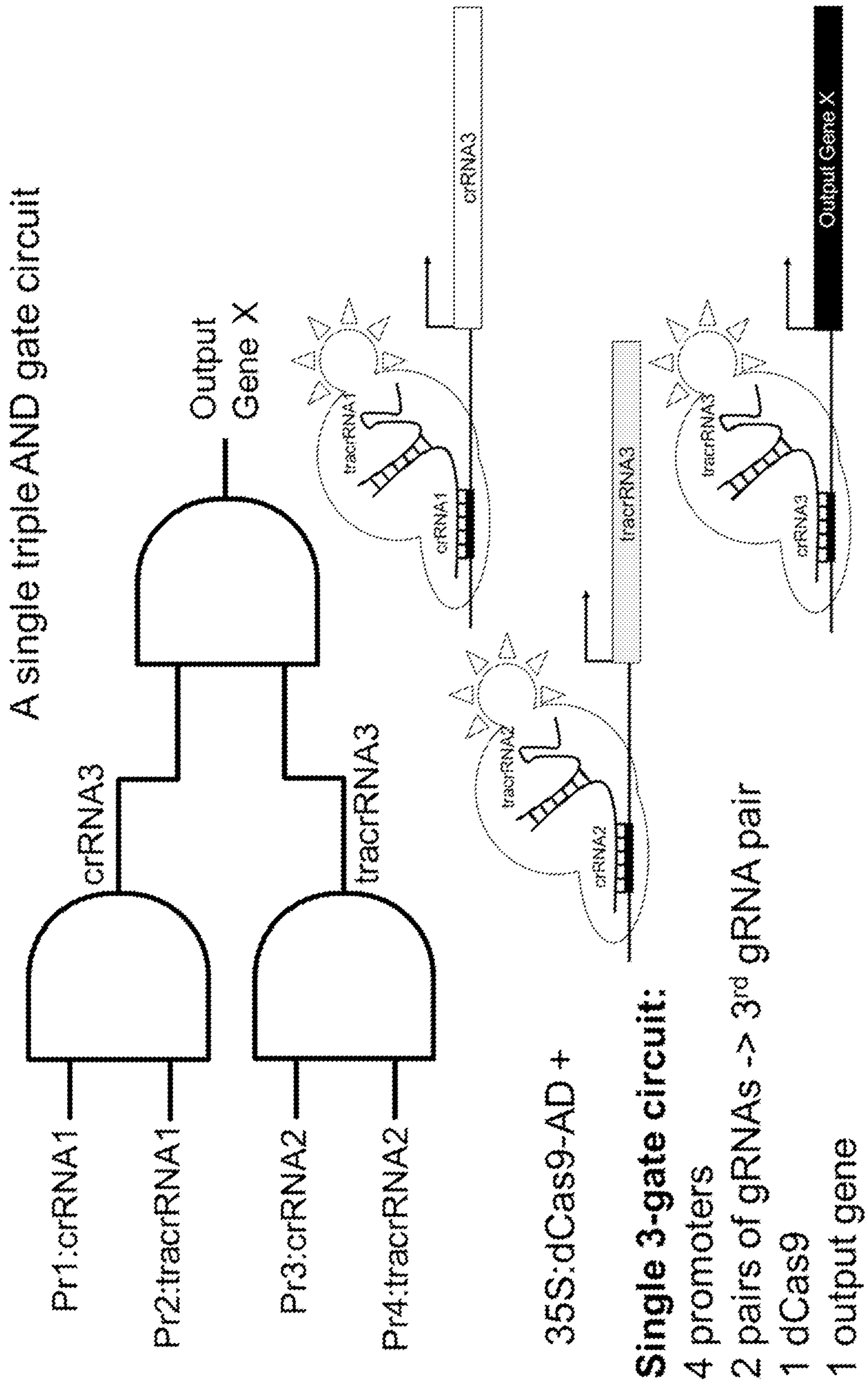
FIG. 7 provides an example of a single triple AND gate circuit where four promoters of interest drive expression of two pairs of gRNAs that control expression of the third gRNA pair that regulates expression of a single output gene, all through the use of a single dCas9 protein.
Figure 9A:
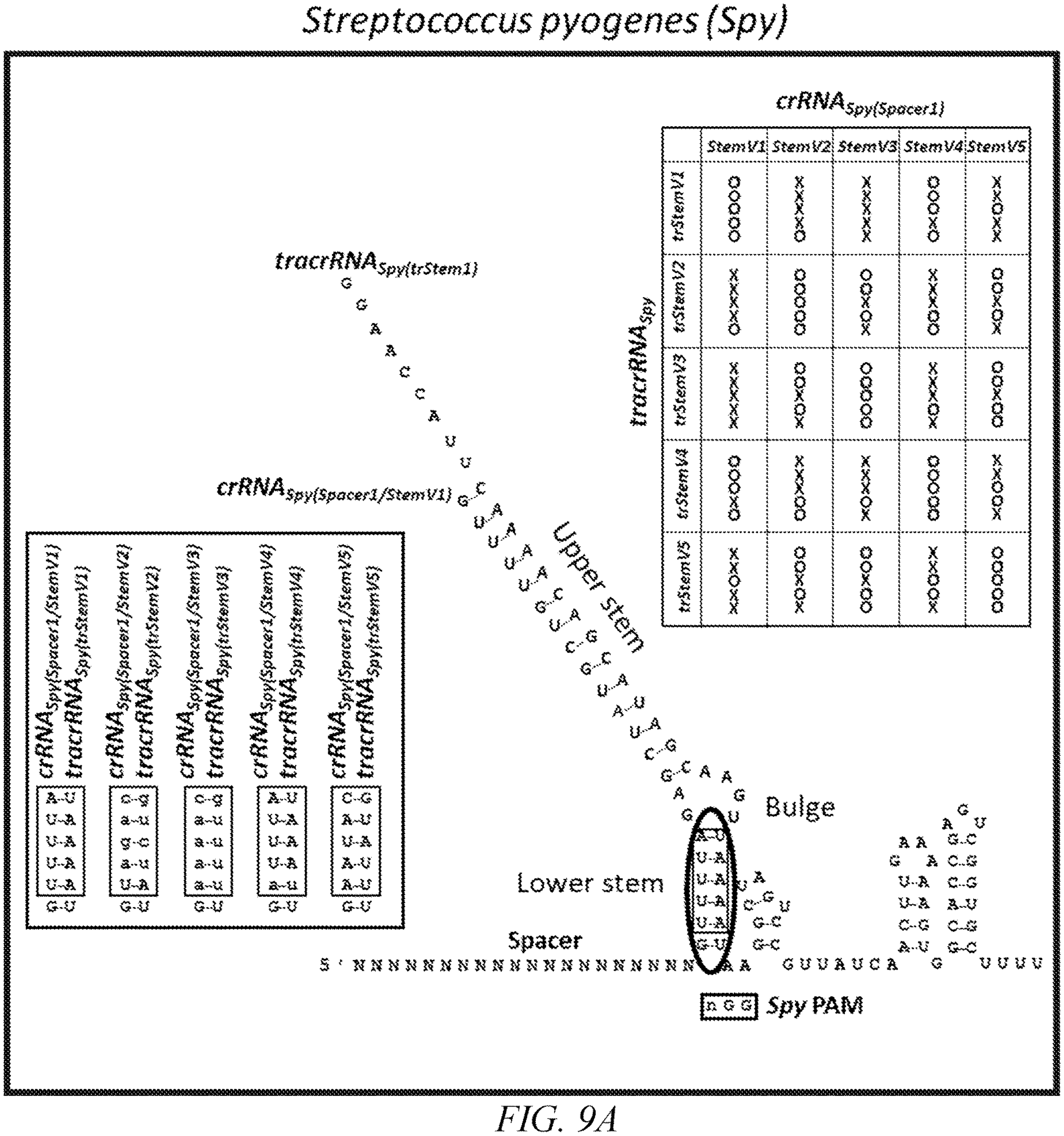
FIGS. 9A-9B. WT crRNA:tracrRNA pairs of *S. pyogenes* (FIG. 9A, Spy) and *S. thermophilus* CRISPR1 (FIG. 9B, Sth1) represent orthogonal CRISPR systems. Pseudo-orthogonal CRISPR systems can be generated on the basis of either Spy or Sth1 by introducing complementary mutations in the lower stems of crRNA:tracrRNA pairs. Lower insets show the variable sequences of the gRNA lower stems (corresponding to the WT sequence marked with the oval in the gRNA structure) that can be introduced into the mutant crRNA:tracrRNA pairs, with modified base pairs marked in lower case. Upper insets show a schematic view of five lower-stem base pairs (the regions surrounded by rectangles in the gRNA structures in the lower insets), with the matching and mismatching base pairs marked as circles and crosses, respectively. $crRNA_{Spy(Spacer/StemV1)}$ (SEQ ID NO:1); $tracrRNA_{Spy(trStem1)}$ (SEQ ID NO:2); $CrRNA_{Sth1(Spacer/StemV1)}$ (SEQ ID NO:3); $tracrRNA_{Sth1(trStem1)}$ (SEQ ID NO:4).
Figure 9B:
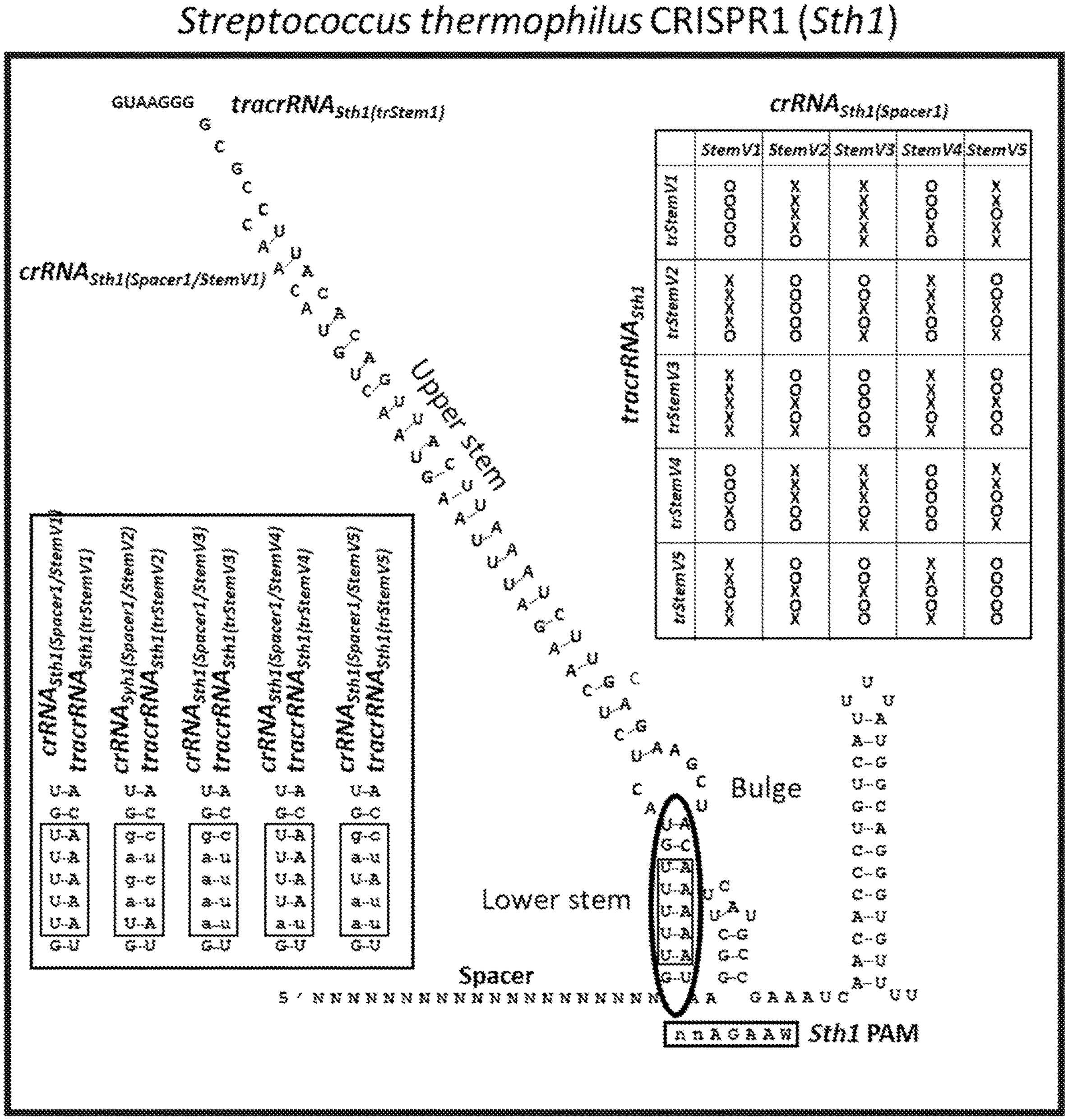
Figure 12:
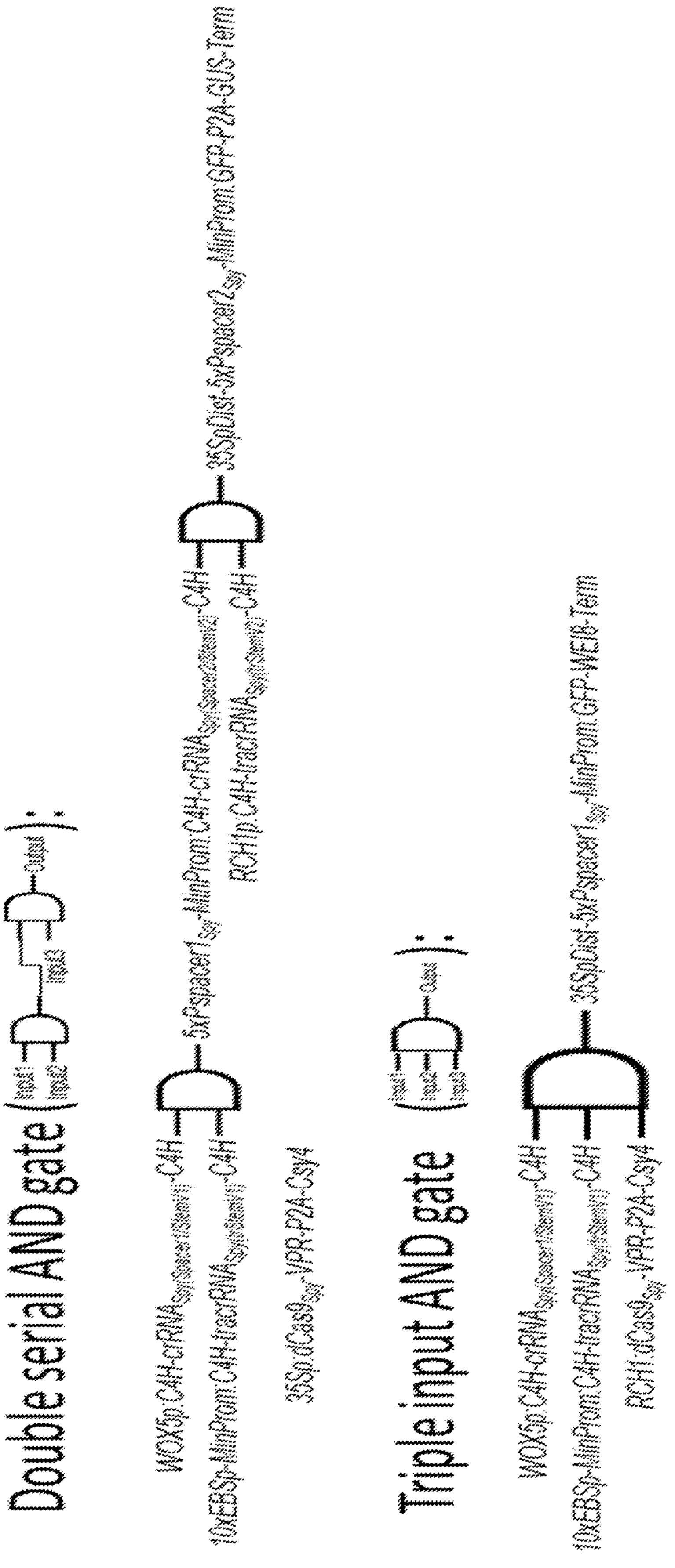
FIG. 12 provides example logic gates showing a double serial AND gate (FIG. 12, upper panel) and a triple input AND gate (FIG. 12, lower panel).

CRISPR-Cas systems, and CRISPR/Cas9, in particular, have emerged as a versatile biotechnological tool to not only induce targeted mutations in a genome, but also to regulate expression of genes of interest by fusing a nuclease-dead version of, for example, Cas9, dCas9, to transcriptional activator (dCas9-AD, aka CRISPRa) or repressor domains (dCas9-RD, aka CRISPRi) and targeting these synthetic transcription factors to the genes' promoters by designing single guide RNA (sgRNA, i.e., fused crRNA and tracrRNA) to recognize specific promoter regions. By using, for example, stimulus-inducible or tissue-specific promoters to drive Cas9 or any other CRISPR-Cas system protein that utilizes hybridizing nucleic acid molecules (e.g., crRNA, tracrRNA) and by taking advantage of the orthogonality of the CRISPR-Cas proteins (e.g., Cas9, Cas12b) from different bacterial species that are active only when assembled with their corresponding sgRNAs (and not with sgRNAs of other species), the present invention shows that one can combine multiple Type II CRISPR-Cas and Type V CRISPR-Cas systems in a living cell to either run several parallel simpler circuits or one combinatorial larger circuit (FIGS. 6, 7 and 12). While the scalability of this approach is potentially limited by the number of independent (non-cross-reacting) Type II CRISPR-Cas and Type V CRISPR-Cas effector polypeptides and guide pairs (e.g., Cas9/sgRNA pairs; Cas12b/sgRNA pairs) available, this invention shows that modifying sgRNA (upper and/or lower stem) to confer specificity of gene regulation allows many more pseudo-orthogonal genetic logic gates to be generated for each existing Type II CRISPR-Cas and Type V CRISPR-Cas complex (e.g., each Cas9/sgRNA complex; each Cas12b/sgRNA complex) (FIGS. 9A-9B). Thus, making the number of possible Type II CRISPR-Cas and Type V CRISPR-Cas pairs available in the many thousands. Further, the utilization of various modified forms of the CRISPR-Cas effector proteins (e.g., Cas9 (e.g., dCas9, Cas9n (nickase); Cas12b (e.g., dCas12b, Cas12bn (nickase)), in addition to active CRISPR-Cas effector proteins, increases the potential of the possible pairs to control not only gene expression (e.g., via Cas9 or Cas12b fusion to a transcriptional regulation domain), but also nucleic acid cutting (e.g., via dCas9, Cas9n, dCas12b, or Cas12bn), visualization (e.g., via CRISPR-Cas effector protein fusion to a reporter), or chromatin state (e.g., via CRISPR-Cas effector protein fusion to a chromatin remodeler or to a histone modification enzyme).

In native CRISPR/Cas9 systems (including, but not limited to, Type II CRISPR-Cas9 systems, e.g., *Streptococcus pyogenes, Spy*, and *S. thermophiles CRISPRJ, Sth*1), and in native Type V-B, Type V-C, Type VE, Type V-F and Type V-G, two different small RNAs, crRNA and tracrRNA, assemble to form a dual guide RNA (dgRNA) (FIGS. 9A-9B, 14 and 15) to target or guide the Type II or Type V CRISPR Cas effector protein to a complementary region on a DNA. crRNA and tracrRNA pair through two complementary regions called the upper and lower stems often separated by a bulge. Disruption of the base-pairing via mutations in as little as two nucleotides in the lower stem region blocks the activity of CRISPR Cas effector protein, e.g., Cas9 activity. However, restoration of base-pairing via complementary mutations enables assembly/folding of functional guide RNA and restores the activity of CRISPR Cas effector protein (FIGS. 14, 15, 16, 17, 18, and 19). Thus, a set of mutant complementary crRNA:tracrRNA pairs may be developed that would support the activity of Cas9, but fail to pair with wild-type and other mutant versions of guide RNAs (FIGS. 9A-9B, 15, 16, 17, 18, and 19). These pairs can be used to generate large sets of pseudo-orthogonal logic gates (e.g., AND gates where both components are required to target the CRISPR Cas effector protein to the DNA) that do not cross-react with all other elements in the circuit and thus can be used in a genetic circuit in either parallel or sequential steps to execute complicated biological tasks. Thus, by expressing multiple non-cross-hybridizing crRNA:tracrRNA pairs one can enable noise-free integration of multiple inputs in a cell in a variety of genetic circuits.

The crRNA and tracrRNA pair with one another through their 3' and 5' regions, respectively, forming an imperfect hairpin comprised of a lower stem, a bulge and an upper stem (FIGS. 9A-9B). As an example, a 42nt-long *Streptococcus pyogenes* crRNA contains two regions: a 20nt 5' spacer region (that is complementary in sequence to a genomic locus of interest (target DNA) and that guides Cas9 to the target DNA) and a 22nt 3' stem (or handle) region partially complementary to the tracrRNA. An 89nt-long tracrRNA consists of a 27nt stem (or handle) region of complementarity to crRNA and a 62nt scaffolding region with two internal hairpins that are required for optimal Cas9 activity (FIG. 9A).

Figure 20:
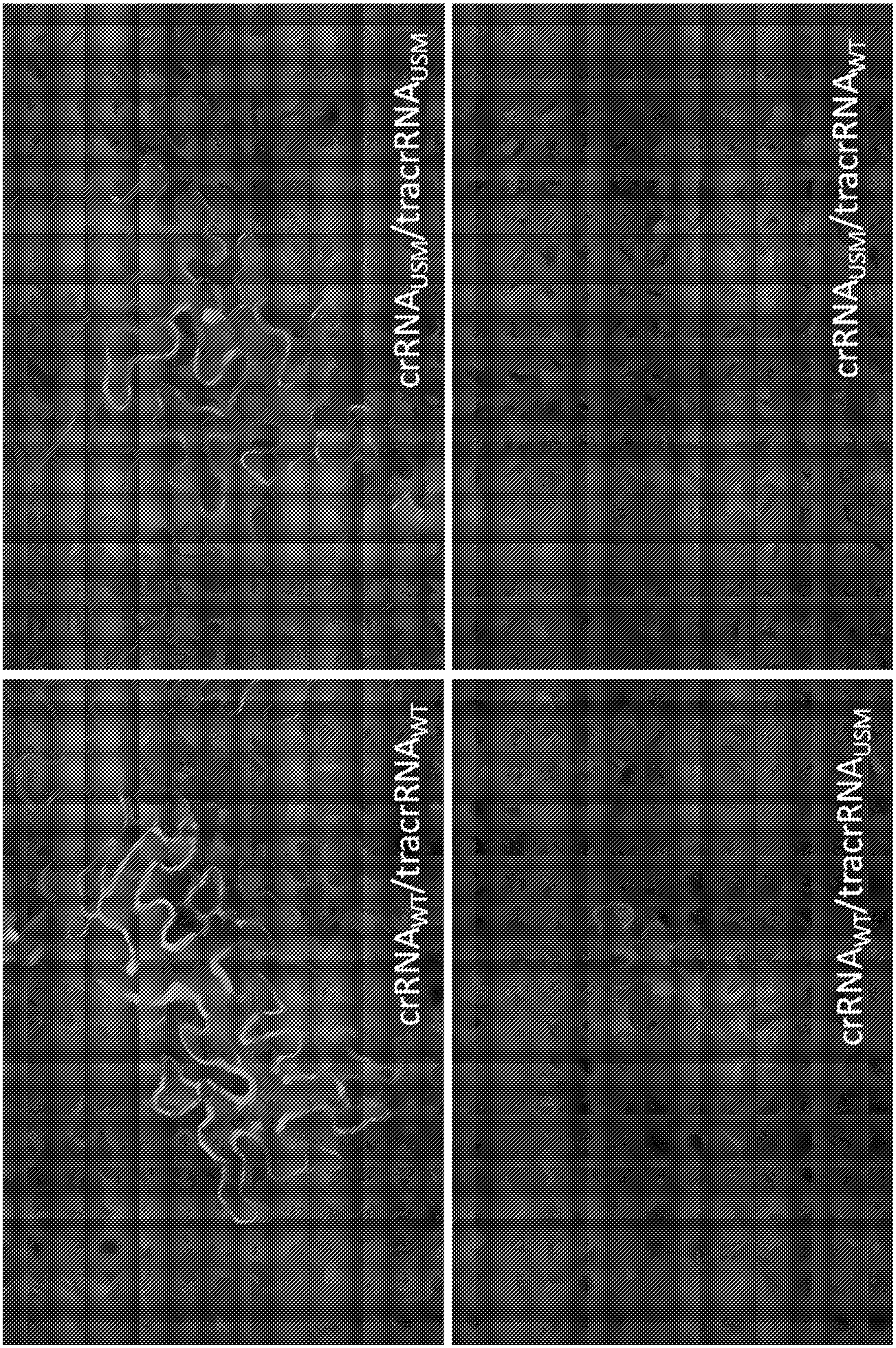
FIG. 20. Mutations in the upper stem of *S. pyogenes* crRNA and tracrRNA are well tolerated in a matched (complementary) combination, but not in mis-matched (non-complementary) combinations of the dual gRNA pair. The mutant USM crRNA/tracrRNA pair was constructed by swapping the 12 terminal base pairs [that correspond to the upper stem region] between crRNA and tracrRNA.

The upper stem of an crRNA-tracrRNA hybrid is at least in part dispensable for the function of guide RNA and can be shortened to, for example, five complementary base pairs, with a tetraloop added to connect crRNA and tracrRNA as in the classical sgRNA. In a further example, the tetraloop may be removed if the crRNA and tracrRNA are connected into a sgRNA via the bulge converted to a terminal loop. In contrast, the bulge and the lower stem appear to be essential for CRISPR Cas effector protein/crRNA:tracrRNA complex function and mutations that change the sequence and disrupt the base pairing of the lower stem abolish CRISPR Cas effector protein activity (e.g., abolish Cas9 activity). However, drastic complementary changes in the lower stem sequences that nonetheless fully preserve the crRNA:tracrRNA base pairing (and the resultant secondary structure) do not interfere with the Cas9 function (FIGS. 14, 15, 16, 17, 18, and 19). Likewise, a swap of the upper stem sequences (replacement of 12 3' terminal nucleotides of crRNA by 12 5' terminal nucleotides of tracrRNA and vice versa) is also well tolerated and does not render the Cas9 inactive as long as the upper stem complementarity is preserved (FIG. 20). Thus, the present invention utilizes mutant crRNA and tracrRNA pairs designed to support the function of Cas9 (e.g., nucleic acid binding, endonuclease and/or nickase activity) when co-expressed together but not when co-expressed with their non-complementary counterparts (e.g., sets of non-cross-interacting crRNA and tracrRNA pairs (FIGS. 9A-9B) in the design of logic gates.

Traditionally, the expression of the crRNA and tracrRNA in living cells is driven by RNA Polymerase III (RNAPIII) promoters, but these promoters are mostly constitutive. To confer stimulus-regulated or tissue-specific expression to crRNA and tracrRNA in living cells, RNA Polymerase II (RNAPII) promoters can be employed to drive their expression. However, RNAPII-transcribed transcripts normally get capped in the 5', cleaved in the 3', polyadenylated and exported out of the nucleus, which is expected to interfere with the crRNA and tracrRNA function. Several systems have been previously used to solve this problem. The RNA endoribonuclease Csy4 from *Pseudomonas aeruginosa*, tRNA, and ribozymes have been shown to function in plants. For example, to remove the mRNA cap and poly(A) tail and to retain the small RNAs in the nucleus, previously described ribozymes may be included in the small RNA gene sequences to allow excision of mature crRNA and tracrRNA from the otherwise capped and polyadenylated transcripts. Thus, in our system, each component of a crRNA:tracrRNA pair may be expressed under synthetic or native RNAPII-controlled promoters to drive activation or repression of output by targeting deactivated CRISPR Cas effector proteins (dCas9-AD or dCas9-RD (AD=transcription activation domain; RD=transcription repression domain)) to the target promoters specifically in the tissues where both crRNA and tracrRNA are co-expressed. Thus, in some embodiments, alternative complementary crRNA:tracrRNA pairs may be expressed under the synthetic or natural RNAPII-controlled promoters of interest.

As discussed, the ability of a crRNA-tracrRNA complex to guide a CRISPR Cas effector protein to a specific DNA sequence depends on the proper base-pairing in the lower and upper stem of this RNA complex. However, the actual nucleotide sequence of the stem may be altered as long as base-pair complementarity is preserved. Utilizing these characteristics, a large number of crRNA-tracrRNA orthogonal pairs may be generated. By using different promoters to drive the expression of the crRNA and the tracrRNA in each orthogonal pair, and by combining several of these orthogonal pairs in specific arrayed configurations (logic gates), complex logic operations on input signals (promoter activities) may be carried out by these novel molecular devices.

Figure 10A:
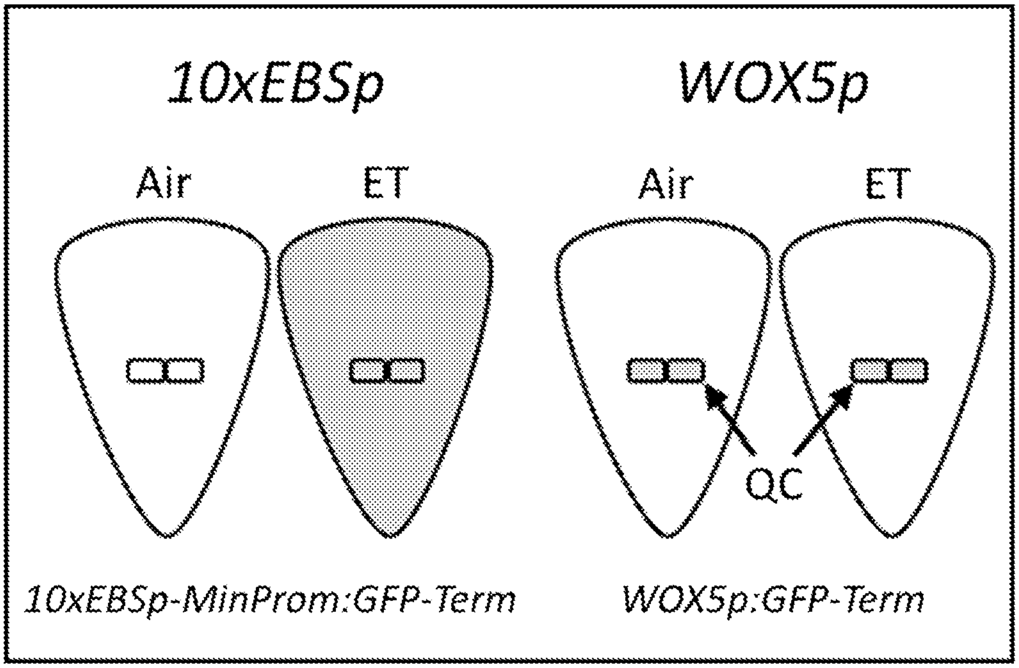
FIG. 10A-10B. Original (FIG. 10A) and derived (FIG. 10B) patterns of gene expression obtainable with two drivers, synthetic ethylene (ET)-inducible promoter 10xEBSp and native QC-enriched promoter WOX5p, using the logic gate design of the present invention. Example construct schematics for each logic gate are shown. dCas9 is a nuclease-dead version of Cas9; VPR is a transcriptional activation domain; 35Sp and 35SpDist are the full and distal part of the 35S promoter; P2A is a self-cleaving peptide; Csy4 is a nuclease that cuts RNA in a C4H hairpin; Spacer and Stem are two variable parts of crRNA; trStem is a variable part of tracrRNA; 5xPspacer is a tandem of five copies of the gRNA target site that is identical to Spacer but also carries a PAM (NGG for Spy and NNAGAAW for Sth1) in the 3'; MinProm and Term are synthetic minimal promoter and 3'UTR; GFP is a fluorescent protein gene.
Figure 10B:
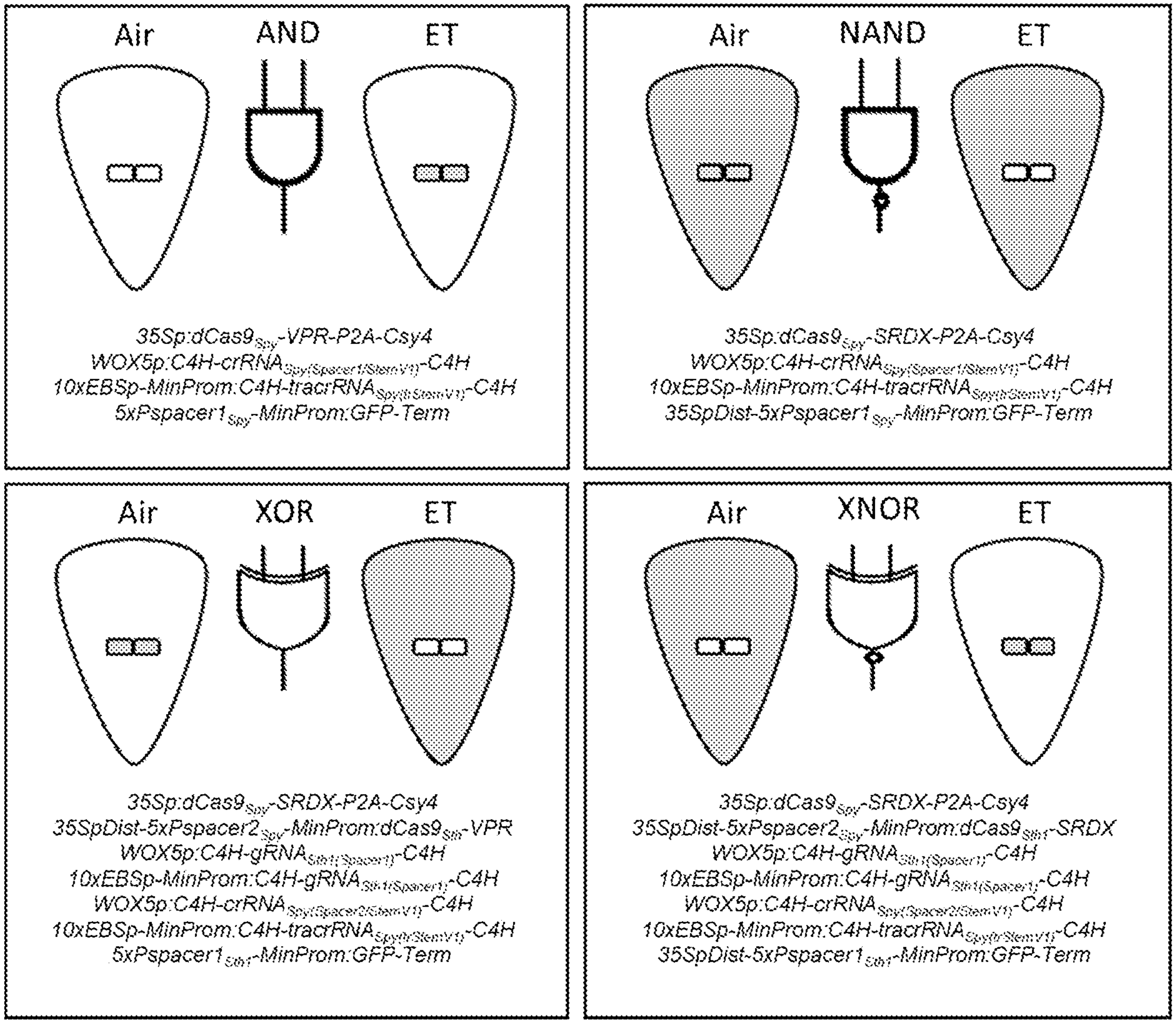

Some of the capabilities of this system can be illustrated by an example of expressing a tracrRNA under the synthetic hormone-inducible promoter 10xEBSp and crRNA under a tissue-specific promoter WOX5p and by fusing a 35Sp-driven dCas9 to the VPR transcriptional activation domain (FIGS. 10A-10B). The resulting logic AND gate will lead to the activation by a hormone (ethylene) of the output GFP reporter gene (or any gene of interest) exclusively in the tissue of choice (the root quiescent center, QC, in this example). Likewise, by converting dCas9 to a repressor with the help of the SRDX domain, a GFP reporter can be expressed ubiquitously except for the ethylene-mediated repression occurring specifically in the QC (representing a NAND gate) (FIGS. 10A-10B).

Accordingly, utilizing the compositions and methods of the present invention, higher order combinations of logic gates are possible. In some embodiments, use of two incompatible orthogonal versions of a CRISPR Cas effector protein (e.g., Cas9 from *S. pyogenes* and *S. thermophilus*) that work exclusively with their own crRNA:tracrRNA partners, (e.g., dCas9a-VPR64 (a transcriptional activator) and dCas9b-SRDX (a transcriptional repressor) can be co-expressed to differentially regulate different subsets of target nucleic acids or genes in the same cell (or the same subset in different cells of a multicellular organism) by a desired array of stimuli. By using a combination of dual and single guide RNAs with two or more orthogonal versions of a CRISPR Cas effector protein (e.g., Cas9 from Spy and Sth1) with each uniquely recognizing its own guide RNA (sgRNA or crRNA-tracrRNA hybrid), countless number of independent modules may be generated. For example, with just two Cas9 nucleases and two sets of guide RNAs all basic logic gates can be recreated (see, e.g., FIG. 10A-10B). As a further example, utilizing two promoters (for example, a hormone-inducible promoter and a tissue-specific promoter) as described herein for driving the expression of guide RNAs, a wide array of derived patterns of gene expression can be produced, many of which are not otherwise available in the existing collection of native and synthetic promoters.

Figure 8:
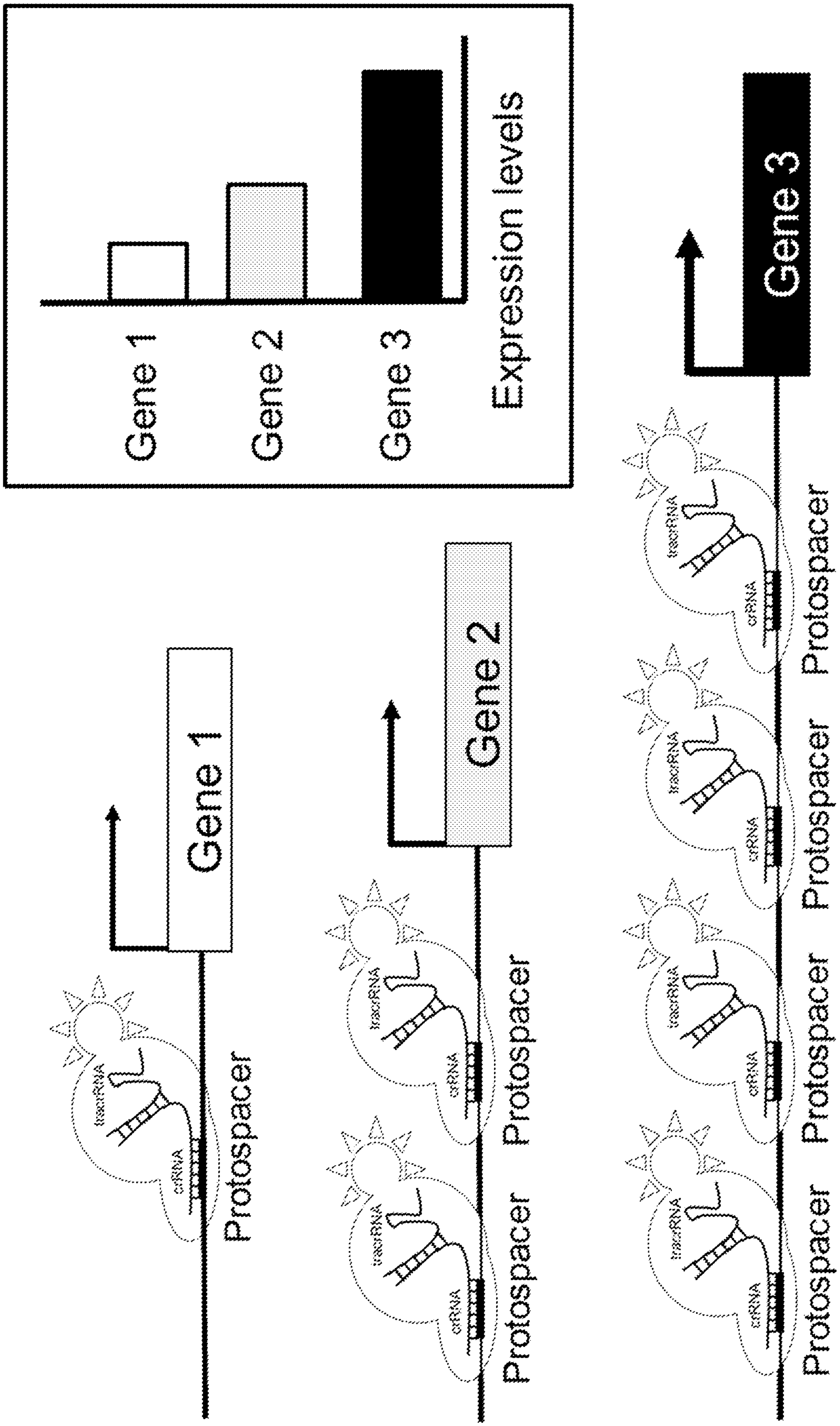
FIG. 8 is an example showing the tunability of the logic gate system of this invention. By regulating the copy number of target protospacer sequences in the promoters of genes of interest, one in theory should be able to tune the levels of expression of the output gene.
Figure 11:
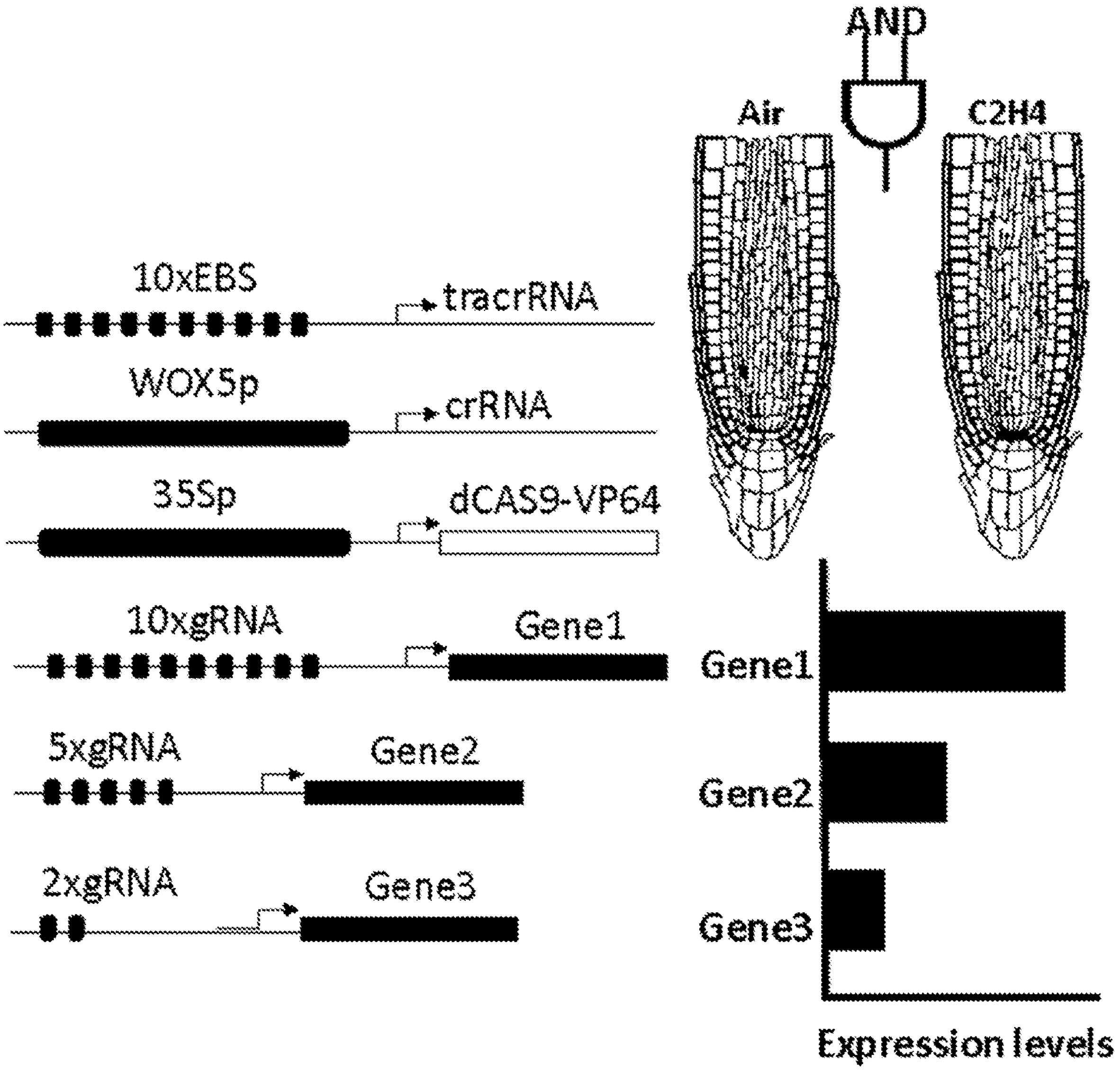
FIG. 11. Coordinated but independently tunable expression levels of multigenic circuit outputs.

In addition to single-gate circuits, multiple logic gates (e.g., 2, 3, 4, 5, 6, 7, 8, 9, 10, 11, 12, 13, 14, 15, 16, 17, 18, 19, 20, 21, 22, 23, 24, 25, or more) of different types operating in a cell may be constructed using the compositions and methods of the present invention, thereby enabling execution of complex genetic programs in several parallel non-interfering circuits or in a single larger multi-step synthetic circuit. An advantage of the present invention is that multiple crRNA:tracrRNA pairs will only work in combination with each other to recruit deactivated or dead CRISPR Cas effector proteins (e.g., dCas9-XD (XD refers to either activation (AD) or repression (RD) domain)) to synthetic promoters of interest and will not interfere with the activity of other co-expressed logic gates that utilize additional non cross-reacting crRNA:tracrRNA pairs complexed with the same CRISPR Cas effector protein. As illustrated with the examples provided above (e.g., FIGS. 9A, 9B, 10A, 10B), the ability to generate dozens of crRNA-tracrRNA pairs that could be expressed simultaneously without interfering with each other opens the possibility to generate true synthetic circuits of unprecedented complexity. Although in the above examples, a reporter gene is utilized as the readout of the different molecular circuits, it is apparent that the CRISPR-based system of this invention could also be used to control the coordinate expression of complex multigenic pathways. Furthermore, the use of synthetic promoters based on the multimerization of CRISPR nucleic acid (crRNA/crDNA) protospacer (target) sequences offers the additional advantage of independent fine-tuning of the levels of expression of each component of the multigenic pathway, while maintaining the coordinate expression of all the genes in the pathway as dictated by the intrinsic properties of a synthetic circuit of interest (FIGS. 8 and 11). Simply by varying the number of protospacer sequence copies in the promoters of output genes, one can achieve the desired level of activity of each gene in the pathway.

Further, the abundance of gene expression data from both endogenous and synthetic promoters represents an invaluable source of "raw" inputs where to "plug-in" synthetic circuits to generate new expression patterns specifically tailored for concrete applications. In addition to generating novel combinations of existing expression patterns, the synthetic genetic circuits also allow for adjustable robustness and specificity. Thus, for example, a combination of AND gates can be used to ensure that the output gene is activated only when not just one but several stimulus-specific gene markers are activated, achieving the highest specificity possible.

The compositions and methods of this invention can be used to take advantage of any stimulus-regulated or stage/tissue-specific promoters (native or synthetic) in any transformable species of interest. The simplicity by which large numbers of orthogonal logic gates can be generated with the proposed crRNA:tracrRNA system makes it possible to combine several logic gates in a single circuit, opening the possibility to develop highly programmable traits. These traits would be expressed/realized only when a predetermined set of conditions (environmental, developmental, tissue-type, etc.) is met or, in other words, when a number of native (endogenous) and/or synthetic promoters are active or, vice versa, inactive in a specific preset combination.

Thus, the base-pairing requirements between the crRNA and the tracrRNA can be utilized to generate large numbers of orthogonal crRNA-tracrRNA pairs. By using different promoters to drive the expression of the crRNA and tracrRNA in a crRNA-tracrRNA pair, and by combining several of those orthogonal pairs, molecular circuits capable of complex logic operations can be easily designed to control the expression of one or more target nucleic acids. In some embodiments, the output is not measured with regard to gene expression, but also in regard to DNA cutting done in tissue/stage-specific manner (via CRISPR Cas effector proteins (e.g., Cas9, Cas12b, and the like, with functional nuclease domains)). For example, this may be desired for the purpose of destroying specific cell types in a complex tissue (e.g., by targeting repetitive elements in the DNA such as transposons to induce cell death via multiple dsDNA breaks).

Accordingly, in some embodiments, the present invention provides a logic gate based system for modifying (altering, controlling) gene expression or modifying a genome, the system comprising: (A) at least one orthogonal (or independent) pair (e.g., 1, 2, 3, 4, 5, 6, 7, 8, 9, 10, 11, 12, 13, 14, 15, or more orthogonal pairs) or at least two orthogonal (or independent) pairs (e.g., 2, 3, 4, 5, 6, 7, 8, 9, 10, 11, 12, 13, 14, 15, or more orthogonal pairs) of hybridizing nucleic acid constructs, each orthogonal pair comprising: (i) a CRISPR nucleic acid (e.g., crRNA, crDNA) construct comprising a repeat sequence and at least one spacer sequence having substantial complementarity to a target nucleic acid, the CRISPR nucleic acid operably linked to a first promoter, and (ii) a trans-activating CRISPR (tracr) nucleic acid (e.g., tracrRNA, tracrDNA) construct comprising a sequence that is complementary to the repeat sequence of the CRISPR nucleic acid of the same orthogonal pair of hybridizing synthetic nucleic acid constructs, the tracr nucleic acid operably linked to a second promoter, which when both (i) and (ii) are (concurrently) expressed in a cell, a synthetic CRISPR nucleic acid-tracr nucleic acid (crRNA-tracrRNA) hybrid is formed having a secondary structure comprising a lower stem, and optionally, an upper stem and which hybrid forms a complex with a Type II or Type V CRISPR-Cas effector protein (e.g., Type II or Type V CRISPR-Cas nuclease (e.g., active HNH and RuvC or RuvC (RuvC-like)), deactivated Type II or Type V CRISPR-Cas effector protein (dCRISPR-Cas effector protein (e.g., dCas9, dCas12b), e.g., inactive HNH and inactive RuvC, or for Type V, an inactive RuvC); or Type II or Type V CRISPR-Cas nickase (nCRISPR-Cas effector protein (e.g., Cas9n, cas12bn), e.g., inactive HNH or inactive RuvC)), and (B) at least one nucleic acid operably linked to a third promoter and encoding a Type II or Type V CRISPR-Cas effector protein (e.g., Cas9, dCas9, Cas9n; Cas12b, dCas12b, Cas12bn), that forms a complex with at least one synthetic CRISPR nucleic acid-tracr nucleic acid hybrid formed by the at least one orthogonal pair of hybridizing nucleic acid constructs; wherein the CRISPR nucleic acid of each orthogonal pair of hybridizing synthetic nucleic acid constructs and a tracr nucleic acid of any other of the at least one orthogonal pairs of hybridizing synthetic nucleic acid constructs comprise at least one non-natural (as compared to the wild type) mismatch (e.g., 1, 2, 3, 4, 5, 6, 7, 8, 9, 10 or more mismatches) between the repeat sequence of the CRISPR nucleic acid of each orthogonal pair of hybridizing synthetic nucleic acid constructs and the sequence that is complementary to the repeat sequence of the CRISPR nucleic acid of a tracr nucleic acid of any other of the at least one orthogonal pairs of hybridizing synthetic nucleic acid. In some embodiments, the at least one spacer sequence may be at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) complementary to a target DNA. In some embodiments, each pair of hybridizing nucleic acid constructs can form a complex with the same CRISPR-Cas effector protein (e.g., a Type II or Type V CRISPR Cas polypeptide, e.g., Cas9, Cas12b) as at least one other pair of hybridizing nucleic acid constructs and/or a different CRISPR-Cas effector protein from at least one other pair of hybridizing nucleic acid constructs, in any combination.

In some embodiments, the at least one orthogonal pair or at least two orthogonal pairs of hybridizing nucleic acid constructs and at least one CRISPR-Cas effector protein (e.g., 1, 2, 3, 4, 5, 6, 7, 8, 9, 10 or more) form a logic gate. In some embodiments, the logic gate provides AND, OR, NAND, NOR, XOR, XNOR, NOT, or YES Boolean logic functions, and any combination thereof.

In some embodiments, a Type II or Type V CRISPR-Cas effector protein may be a dCas effector protein (e.g., dCas9, dCas12b) having an inactive HNH and inactive RuvC (e.g., inactive RuvC for a Type V CRISPR Cas effector protein) and the target nucleic acid may be located on a fourth promoter that is operably linked to an output nucleic acid. In some embodiments, a Type II or Type V CRISPR-Cas effector protein may be an active Type II CRISPR-Cas nuclease (e.g., Cas9, Cas12b), a Type II or Type V CRISPR-Cas nickase (e.g., nCas9, nCas12b), and/or a deactivated/dead Type II or Type V CRISPR-Cas effector protein (e.g., dCas9, dCas12b), and the target nucleic acid may be any nucleic acid in the cell, wherein the target DNA is cut (resulting in, for example, tissue-specific gene inactivation via indels, gene replacement or modification via homologous recombination, or targeted cell death upon cutting DNA in repetitive elements in the genome). Thus, in some embodiments, a Cas9 nuclease useful with the invention may be a dCas9 (from any source) and the target DNA is located in a fourth promoter that is operably linked to an output nucleic acid, wherein the target DNA is activated and/or repressed. In some embodiments, a Cas9 nuclease may be an active Cas9 nuclease or a nickase (nCas9) (from any source) and the target DNA may be any DNA in the cell.

In some embodiments, a lower stem and/or, when present, an upper stem of a synthetic CRISPR nucleic acid-tracr nucleic acid hybrid formed by at least one of the at least one orthogonal pairs of hybridizing nucleic acid constructs may comprise at least one nucleotide modification (optionally at least two nucleotide modification, e.g., at least one base pair modification) as compared to the lower stem and/or upper stem of the corresponding wild type Type II or Type V CRISPR crRNA-tracrRNA hybrid having the same secondary structure as the synthetic hybrid.

In some embodiments a first, second, and third promoters may be separately selected from a synthetic promoter, an endogenous promoter, or a naturally occurring heterologous promoter. In some embodiments, a first, second, and third promoters may be the same or different from each other, or any combination thereof. In some embodiments, a fourth promoter may be the same or different from each of the first, second and third promoters, or any combination thereof. In some embodiments, the first and second promoters that are operably linked to the CRISPR nucleic acid and the tracr nucleic acid, respectively, of each orthogonal pair of constructs may be different from the first and second promoters operably linked to a CRISPR nucleic acid and a tracr nucleic acid, respectively, of any other of the at least one orthogonal pair of hybridizing synthetic nucleic acid constructs.

In some embodiments, each pair of the at least one orthogonal pair of hybridizing synthetic nucleic acid constructs or at least two orthogonal pairs of hybridizing synthetic nucleic acid constructs may form a different synthetic CRISPR nucleic acid-tracr nucleic acid hybrid.

In some embodiments, at least one of the synthetic CRISPR nucleic acid-tracr nucleic acid hybrids formed by the at least one orthogonal pairs of hybridizing synthetic nucleic acid constructs or at least two orthogonal pairs of hybridizing synthetic nucleic acid constructs may form a complex with a Type II or Type V CRISPR-Cas effector protein that is different from a Type II or Type V CRISPR-Cas effector protein that forms a complex with a synthetic CRISPR nucleic acid-tracr nucleic acid hybrid formed by at least one other of the at least one or at least two orthogonal pairs of hybridizing synthetic nucleic acid constructs.

In some embodiments, at least one of the synthetic CRISPR nucleic acid-tracr nucleic acid hybrids formed by the at least one or at least two orthogonal pairs of hybridizing synthetic nucleic acid constructs may form a complex with a Type II or Type V CRISPR-Cas effector protein that is the same as a Type II or Type V CRISPR-Cas effector protein that forms a complex with a synthetic CRISPR nucleic acid-tracr nucleic acid hybrid formed by at least one other of the at least one orthogonal pairs of hybridizing synthetic nucleic acid constructs.

In some embodiments, a logic gate system of this invention may comprise at least two Type II CRISPR-Cas effector proteins and/or Type V CRISPR-Cas effector proteins, each of which may be operably linked to a different promoter. In some embodiments, a logic gate system of this invention may comprise at least two Type II CRISPR-Cas effector proteins and/or Type V CRISPR-Cas effector proteins, each of which may be operably linked to the same promoter. In some embodiments, a promoter operably linked to the output nucleic acid may be a synthetic promoter, a naturally occurring heterologous promoter that is heterologous to cell or to the output nucleic acid. In some embodiments, a promoter operably linked to the output nucleic acid may be endogenous to the cell or to the output nucleic acid.

In some embodiments a wild type Type II CRISPR nucleic acid-tracr nucleic acid may be a wild type Type II CRISPR nucleic acid and a wild type Type II tracr nucleic acid from, for example, *Lactobacillus* spp. Type II system, a *Bifidobacterium* spp. Type II system, a *Staphylococcus* spp. Type II system, a *Neisseria* spp. Type II system, a *Campylobacter* spp. Type II system, a *Kandleria* spp. Type II system, a *Leuconostoc* spp. Type II system, an *Oenococcus* spp. Type II system, a *Pediococcus* spp. Type II system, a *Streptococcus* spp. Type II system, a *Weissella* spp. Type II system, and/or a *Olsenella* spp. Type II system. In some embodiments, a wild type Type II CRISPR nucleic acid-tracr nucleic acid may be a wild type Type II CRISPR nucleic acid and a wild type Type II tracr nucleic acid from *Streptococcus pyogenes* or *Streptococcus thermophilus*.

In some embodiments a wild type Type V CRISPR nucleic acid-tracr nucleic acid may be a wild type Type V CRISPR nucleic acid and a wild type Type V tracr nucleic acid from, for example, an *Alicyclobacillus* spp. Type V system, a *Oleophilus* spp. Type V system, and/or a *Deltaproteobacteria* spp. Type V system, optionally where the *Alicyclobacillus* spp. Type V system may be from *Alicyclobacillus acidoterrestris*, the *Deltaproteobacteria* spp. Type V system may be from *Deltaproteobacteria bacterium*.

An "output nucleic acid" as used herein refers to a nucleic acid encoding a gene product whose transcription is regulated by any of the aforementioned logic gates (comprised of a Type II or a Type V crRNA-tracrRNA and for example a dCas9-XD or a dCas12b-XD), to a nucleic acid that is cut by a Type II or Type V CRISPR-Cas effector protein (e.g. Cas9, Cas12b; e.g., to induce mutations in the target DNA) or to a nucleic acid bound by a Type II or Type V CRISPR-Cas effector protein operably linked to a chromatin modifier (e.g., to change chromatin state) or a fluorescent protein (e.g., to mark specific chromatin regions). In some embodiments, the output nucleic acid is operably linked to a synthetic promoter. In some embodiments, the output nucleic acid is operably linked to a naturally occurring heterologous promoter. In some embodiments, the output nucleic acid is operably linked to a promoter that is endogenous to the cell. In some embodiments, the output nucleic acid is operably linked to a promoter that is endogenous to the output nucleic acid.

In some embodiments, when two or more CRISPR-Cas effector proteins are provided, each may be operably linked to a different promoter. In some embodiments, at least two CRISPR-Cas effector proteins may be operably linked to the same promoter.

A target DNA may be any DNA in a cell including, but not limited to, chromosomal DNA, plasmid DNA, plastid DNA, mitochondrial DNA, repetitive DNA, coding DNA, non-coding DNA (e.g., promoter), intergenic DNA, transposon, and/or viral DNA.

In some embodiments, the secondary structure formed by the synthetic CRISPR nucleic acid-tracr nucleic acid hybrid of each of at least one orthogonal pair of hybridizing synthetic nucleic acid constructs may be the same as a secondary structure formed by a wild type (Type II or Type V) CRISPR nucleic acid-tracr nucleic acid hybrid. In some embodiments, a lower stem and/or, when present, a upper stem of the synthetic CRISPR nucleic acid-tracr nucleic acid hybrid formed by at least one of the at least one orthogonal pair of hybridizing nucleic acid constructs may comprise at least one nucleotide modification (e.g., 1, 2, 4, 6, 8, 10, 12, 14, 16, 18, 20, 22, 24, 26, 28, 30 or more nucleotide modifications) (optionally at least two nucleotide modification, i.e., a modification of at least one base pair, e.g., 2, 4, 6, 8, 10, 12, 14, 16, 18, 20, 22, 24, 26, 28, 30 or more nucleotide modifications, e.g., a modification of at least 1, 2, 3, 4, 5, 6, 7, 8, 9, 10, 11, 12, 13, 14, 15, 16, or more base pairs), thereby maintaining base pairing of the synthetic CRISPR nucleic acid-tracr nucleic acid hybrid) as compared to a lower stem and/or upper stem of a corresponding wild type (Type II or Type V) CRISPR crRNA-tracrRNA hybrid having the same secondary structure as the synthetic hybrid. In some embodiments, at least one of the at least two orthogonal pairs of hybridizing nucleic acid constructs is a wild type (Type II) CRISPR crRNA-tracrRNA hybrid (i.e., does not comprise any nucleotide modifications to the lower stem and/or upper stem as compares to the wild type). In some embodiments, when the logic gate system is designed, for example, to fine tune the activity of a CRISPR-Cas effector protein (e.g., nuclease, activation, repression, etc.) against specific targets or to generate different levels of activation/repression/cutting, there may be weak or inefficient binding between the orthogonal pairs of hybridizing nucleic acid constructs wherein the CRISPR nucleic acid-tracr nucleic acid hybrid that is formed comprises at least one non-natural mismatch (e.g., 1, 2, 3, 4, 5, 6, 7, 8, 9, 10, 11, 12, 13, 14, 15, 16, or more mismatches) as compared to a corresponding wild type (Type II or Type V) CRISPR crRNA-tracrRNA hybrid or as compared to the CRISPR nucleic acid-tracr nucleic acid hybrid between the crRNA and tracrRNA of the at least one pair of hybridizing nucleic acid constructs.

In some embodiments, a promoter useful with the invention (e.g., a first promoter, a second promoter, a third promoter, and/or a fourth promoter) may be a synthetic promoter, an endogenous promoter, or a naturally occurring heterologous promoter, the expression pattern of any of which may be, for example, constitutive, tissue specific, development-stage-specific, repressible and/or inducible. In some embodiments, a first promoter, second promoter, third promoter and/or fourth promoter may each be the same or different from one another in any combination (e.g., the first, second and third promoters may be the same but different from the fourth promoter; or the first and second promoter may be the same and the third promoter and fourth promoter may be different from the first and second promoter and different from each other, and the like). In some embodiments, a first promoter and a second promoter operably linked to a CRISPR nucleic acid and a tracr nucleic acid, respectively, of an orthogonal pair of hybridizing nucleic acid constructs may be different from a first promoter and a second promoter operably linked to a CRISPR nucleic acid and a tracr nucleic acid, respectively, of any other orthogonal pair of hybridizing synthetic nucleic acid constructs.

In some embodiments, each pair of the at least one orthogonal pair of hybridizing synthetic nucleic acid constructs forms a different synthetic CRISPR nucleic acid-tracr nucleic acid hybrid. Thus, in some embodiments, when three, four, five, six, or more orthogonal pairs of hybridizing synthetic nucleic acid constructs are provided, each pair may form a different synthetic CRISPR nucleic acid-tracr nucleic acid hybrid that is different from any other pair provided.

In some embodiments, at least one of the synthetic CRISPR nucleic acid-tracr nucleic acid hybrids formed by the at least one orthogonal pair of hybridizing synthetic nucleic acid constructs may form a complex with a CRISPR-Cas effector protein (e.g., Cas9, Cas12b) that is different from a CRISPR-Cas effector protein that forms a complex with a synthetic CRISPR nucleic acid-tracr nucleic acid hybrid formed by at least one other of the at least two orthogonal pairs of hybridizing synthetic nucleic acid constructs. In some embodiments, at least one of the synthetic CRISPR nucleic acid-tracr nucleic acid hybrids formed by the at least one orthogonal pair of hybridizing synthetic nucleic acid constructs forms a complex with a CRISPR-Cas effector protein that is the same as a CRISPR-Cas effector protein that forms a complex with a synthetic CRISPR nucleic acid-tracr nucleic acid hybrid formed by at least one other of the at least one orthogonal pairs of hybridizing synthetic nucleic acid constructs.

In some embodiments, a pair of hybridizing nucleic acid constructs is provided, the pair comprising: (A) a CRISPR nucleic acid (e.g., crRNA, crDNA) construct comprising a repeat sequence and at least one spacer sequence having substantial complementarity to a target nucleic acid; and (B) a trans-activating CRISPR (tracr) nucleic acid (e.g., tracrRNA, tracrDNA) construct comprising a sequence that is complementary to the repeat sequence of the CRISPR nucleic acid of the same orthogonal pair of hybridizing synthetic nucleic acid constructs, which when both (A) and (B) are expressed in a cell, a synthetic CRISPR nucleic acid-tracr nucleic acid (e.g., crRNA-tracrRNA) hybrid is formed, wherein the synthetic CRISPR nucleic acid-tracr nucleic acid hybrid comprises a lower stem and/or optionally, an upper stem, and the lower stem, and/or when present, the upper stem, may comprise at least one nucleotide modification (e.g., 1, 2, 3, 4, 5, 6, or 7 or more nucleotide modifications; optionally at least one base pair modification, e.g., 2, 4, 6, 7, 8, 10, 12 or more nucleotide modifications) as compared to a lower stem and/or an upper stem of a wild type (Type II or Type V) CRISPR nucleic acid-tracr nucleic acid hybrid corresponding to the synthetic CRISPR nucleic acid-tracr nucleic acid hybrid. In some embodiments, the crRNA (A) and the tracrRNA (B) may be expressed concurrently in the cell. In some embodiments, the crRNA (A) may be expressed prior to or after the tracrRNA (B) is expressed.

In some embodiments, at least two orthogonal pairs of hybridizing synthetic nucleic acid constructs are provided, comprising: (A) a first hybridizing pair comprising (1) a first synthetic CRISPR nucleic acid (e.g., crRNA, crDNA) construct and (2) a second synthetic trans-encoded CRISPR (tracr) nucleic acid (e.g., tracrRNA, tracrDNA) construct, which when both (A1) and (A2) are expressed in a cell, a first synthetic CRISPR nucleic acid-tracr nucleic acid hybrid is formed having the secondary structure of a first corresponding wild type (Type II or Type V) CRISPR nucleic acid-tracr nucleic acid hybrid that forms a complex with a first CRISPR-Cas effector protein (e.g., Cas9, Cas12b), wherein the first synthetic CRISPR nucleic acid-tracr nucleic acid hybrid comprises a first lower stem and a first upper stem, and the first lower stem and/or the first upper stem comprise at least one nucleotide modification (optionally at least two nucleotide modifications, e.g., at least one base pair modification that maintains base pairing of the synthetic CRISPR nucleic acid-tracr nucleic acid hybrid) as compared to a lower stem and/or an upper stem of the first corresponding wild type (Type II or Type V) CRISPR nucleic acid-tracr nucleic acid hybrid; and (B) a second hybridizing pair comprising (1) a second synthetic CRISPR nucleic acid (e.g., crRNA, crDNA) construct and (2) a second synthetic trans-encoded CRISPR (tracr) nucleic acid (e.g., tracrRNA, tracrDNA) construct, which when both (B1) and (B2) are expressed in a cell a second synthetic CRISPR nucleic acid-tracr nucleic acid hybrid is formed having the secondary structure of a second corresponding wild type (Type II or Type V) CRISPR nucleic acid-tracr nucleic acid hybrid that forms a complex with a second CRISPR-Cas effector protein, wherein the second synthetic CRISPR nucleic acid-tracr nucleic acid hybrid comprises a second lower stem and a second upper stem, and the second lower stem and/or the second upper stem comprise at least one nucleotide modification (optionally at least two nucleotide modifications, e.g., at least one base pair modification that maintains base pairing of the synthetic CRISPR nucleic acid-tracr nucleic acid hybrid) as compared to a lower stem and/or an upper stem of the second corresponding wild type (Type II or Type V) CRISPR nucleic acid-tracr nucleic acid hybrid, wherein the first synthetic CRISPR nucleic acid and the second synthetic tracr nucleic acid, and the second synthetic CRISPR nucleic acid and the first synthetic tracr nucleic acid do not hybridize to form a CRISPR nucleic acid-tracr nucleic acid hybrid that forms a complex with the first CRISPR-Cas effector protein or the second CRISPR-Cas effector protein. In some embodiments, the first and second CRISPR-Cas effector protein may be the same or they may be different. In some embodiments, the first synthetic CRISPR nucleic acid and the second synthetic tracr nucleic acid, and the second synthetic CRISPR nucleic acid and the first synthetic tracr nucleic acid may hybridize weakly or inefficiently to form a CRISPR nucleic acid-tracr nucleic acid hybrid that forms a complex with the first CRISPR-Cas effector protein or the second CRISPR-Cas effector protein.

In some embodiments, the at least two orthogonal pairs of constructs may further comprise a third hybridizing pair of nucleic acid constructs comprising, (C) a third hybridizing pair comprising (1) a third synthetic CRISPR nucleic acid (e.g., crRNA, crDNA) construct and (2) a third synthetic trans-encoded CRISPR (tracr) nucleic acid (e.g., tracrRNA, tracrDNA) construct, which when both (C1) and (C2) are expressed in a cell a third synthetic CRISPR nucleic acid-tracr nucleic acid hybrid is formed having the secondary structure of a third corresponding wild type (Type II or Type V) CRISPR nucleic acid-tracr nucleic acid hybrid that forms a complex with a third CRISPR-Cas effector protein (e.g., Cas9, Cas12b), wherein the third synthetic CRISPR nucleic acid-tracr nucleic acid hybrid comprises a third lower stem and optionally, a third upper stem, and the third lower stem and/or, when present, the third upper stem comprise at least one base pair modification that maintains base pairing of the synthetic CRISPR nucleic acid-tracr nucleic acid hybrid) as compared to a lower stem and/or an upper stem of the third corresponding wild type (Type II or Type V) CRISPR nucleic acid-tracr nucleic acid hybrid, wherein the third synthetic CRISPR nucleic acid does not hybridize with the first tracr nucleic acid or the second tracr nucleic acid to form a complex with the first, second or third CRISPR-Cas effector protein, and the third synthetic tracr nucleic acid does not hybridize to the first CRISPR nucleic acid or the second CRISPR nucleic acid to form a complex with the first, second or third CRISPR-Cas effector protein. In some embodiments, the first, second, and third CRISPR-Cas effector protein may be the same as each other or they may be different from one another, or any combination thereof. In some embodiments, the third synthetic CRISPR nucleic acid may weakly or inefficiently hybridize to the first synthetic tracr nucleic acid and/or the second synthetic tracr nucleic acid, and the third synthetic CRISPR nucleic acid and the first and/or second synthetic tracr nucleic acid may hybridize weakly or inefficiently to form one or more CRISPR nucleic acid-tracr nucleic acid hybrids that forms a complex with the first, second and/or third CRISPR-Cas effector protein.

In some embodiments, a first, second and/or third CRISPR-Cas effector protein may each be a different CRISPR-Cas effector protein or they may each be the same CRISPR-Cas effector protein, in any combination. Thus, the first, second and/or third CRISPR-Cas effector proteins may all be the same or they may each be different. Alternatively, the first and second CRISPR-Cas effector proteins may be the same as each other and different from the third CRISPR-Cas effector protein or the second and third CRISPR-Cas effector proteins may be the same as each other and different from the first CRISPR-Cas effector protein, and the like.

In some embodiments, the lower stem of the synthetic crRNA-tracrRNA hybrid may comprise at least one nucleotide modification (e.g., at least 1, 2, 3, 4, 5, 6, or 7 or more (e.g., up to the full length of the lower stem); optionally at least one base pair modification, e.g., 2, 4, 6, 7, and the like, base pair modifications) as compared to the lower stem of the corresponding wild type CRISPR (Type II or Type V) CRISPR nucleic acid-tracr nucleic acid hybrid. That is, in some embodiments, all nucleotides in a lower stem and/or upper stem (e.g., all base pairs) of a synthetic hybrid may be changed/modified (100%), while at the same time maintaining the base pairing and secondary structure as compared to a corresponding wild type CRISPR (Type II or Type V) CRISPR nucleic acid-tracr nucleic acid hybrid. As another example, only one base pair modification, two base pair modifications, three base pair modifications, four base pair modifications or more may be present in a lower stem of the synthetic hybrid (e.g., a change of one base pair in a five base pair stem, provides 80% identity to the WT; a change of one base pair in an nine base pair stem provides 89% identity to the WT), while at the same time maintaining the base pairing and secondary structure as compared to a corresponding wild type CRISPR (Type II or Type V) CRISPR nucleic acid-tracr nucleic acid hybrid.

In some embodiments, when present, the upper stem of a synthetic CRISPR nucleic acid-tracr nucleic acid hybrid may comprise at least one nucleotide modification (e.g., at least 1, 2, 3, 4, 5, 6, 7, 8, 9, 10, 11, 12, 13, 14, 15, or more (e.g., up to the full length of the upper stem) optionally at least one base pair modification) as compared to the upper stem of the corresponding wild type CRISPR (Type II or Type V) CRISPR nucleic acid-tracr nucleic acid hybrid. Thus, for example, all base pairs in an upper stem of a synthetic hybrid may be changed/modified (100%) while at the same time maintaining the base pairing and secondary structure as compared to a corresponding wild type CRISPR (Type II or Type V) CRISPR nucleic acid-tracr nucleic acid hybrid. For example, 10 base pairs (20 nucleotides) of a 15 base pair upper stem may be modified, while at the same time maintaining the base pairing and secondary structure as compared to a corresponding wild type CRISPR (Type II) CRISPR nucleic acid-tracr nucleic acid hybrid (which provides about 66% identity to the wild type sequence).

The CRISPR nucleic acid-tracr nucleic acid hybrids produced from the pairs of hybridizing nucleic acid constructs of the invention may comprise any combination of base pair modifications in the upper and lower stem.

As previously described, a corresponding wild type (Type II) CRISPR nucleic acid-tracr nucleic acid hybrid useful with this invention may be from any wild type Type II or Type V CRISPR-Cas system.

In some embodiments, a CRISPR nucleic acid construct of the invention may be operably linked to a first promoter and a tracr nucleic acid construct of the invention may be operably linked to a second promoter. In some embodiments, the first promoter and the second promoter may be the same. In some embodiments, the first promoter and the second promoter may be different. In some embodiments, a first promoter and a second promoter may be separately an endogenous promoter, a naturally occurring heterologous promoter and/or a synthetic promoter. In some embodiments, the expression pattern of the first promoter may be constitutive, tissue-specific, development-stage-specific, repressible and/or inducible and the expression pattern of the second promoter may be constitutive, tissue-specific, development-stage-specific, repressible and/or inducible.

A crRNA and/or a tracrRNA can be expressed from an RNA Pol I promoter, an RNA Pol II promoter or an RNA Pol III promoter. When expressed from an RNA Pol II promoter, removal of the 5' cap and poly(A) is carried out either by means of nuclease cleavage (in that case, nuclease sites need to flank the active part of crRNA and tracrRNA), ribozyme sequences (that are self-cleaving), or tRNA processing (with tRNA sequences flanking the active part of crRNA or tracrRNA), that rely on cellular or heterologously expressed nucleases, ribozyme self-cleavage, and cellular tRNA processing enzymes, respectively).

In some embodiments, a CRISPR nucleic acid construct may comprise at least one spacer sequence having substantial complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) or full complementarity (100%) with a target nucleic acid (e.g., target DNA). In some embodiments, a CRISPR nucleic acid construct may comprises at least one spacer sequence having about 80% to 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity) or about 90% to 100% complementarity (e.g., about 90%, 91%, 92%, 93%, 94%, 95%, 96%, 97%, 98%, 99%, and the like, complementarity) with a target DNA. In some embodiments, the CRISPR nucleic acid construct may comprise at least two spacer sequences that that are substantially complementary (e.g., about 70% to about 100%, about 80% to about 100%, or about 90 to 100% complementarity) to different target DNAs.

In some embodiments, a target nucleic acid may be any DNA in the cell including but not limited to DNA encoding a gene, intergenic DNA, non-coding DNA (e.g., functional, regulatory, repetitive), plastid (chloroplast) DNA, mitochondrial DNA, plasmid DNA, or viral DNA. In some embodiments, a target nucleic acid may be endogenous or it may be exogenous (e.g., a transgene, viral gene). In some embodiments, the target nucleic acid may be a promoter or a fragment of a promoter.

In some embodiments, the logic gate systems and pairs of hybridizing nucleic acid constructs of the present invention may be introduced into the genome of a cell in a tissue specific, cell type specific, and precise manner through homologous recombination.

In some embodiments, a method for modifying gene expression or modifying a genome of a cell is provided, comprising introducing into a cell a logic-gate-based system of the present invention as described herein. In some embodiments, a cell comprising the logic-gate-based system of the present invention is provided.

In some embodiments, a method for modifying (altering, controlling) the expression of at least one gene in a cell or modifying a genome of a cell is provided, comprising introducing into the cell at least one pair of hybridizing nucleic acid constructs of the invention and a CRISPR-Cas effector protein, or a nucleic acid construct encoding a CRISPR-Cas effector protein, wherein the CRISPR-Cas effector protein forms a complex with a synthetic CRISPR nucleic acid-tracr nucleic acid hybrid formed by the at least one pair of hybridizing synthetic nucleic acid constructs, thereby modifying the expression of the at least one gene in the cell or modifying the genome of the cell.

In some embodiments, a method for modifying (altering, controlling) the expression of at least one gene in a cell or modifying a genome of a cell is provided, comprising introducing into the cell at least two pairs of hybridizing nucleic acid constructs of the invention and a CRISPR-Cas effector protein, or a nucleic acid construct encoding a CRISPR-Cas effector protein, wherein the CRISPR-Cas effector protein forms a complex with a synthetic CRISPR nucleic acid-tracr nucleic acid hybrid formed by each of the at least two pairs of hybridizing synthetic nucleic acid constructs, thereby modifying the expression of the at least one gene in the cell or modifying the genome of the cell.

Modification of a genome can comprise a modification anywhere on a chromosome (e.g., gene, intergenic, non-coding (e.g., functional, regulatory, repetitive), or in plastid (chloroplast) DNA, mitochondrial DNA, plasmid DNA, or viral DNA. In some embodiments, the genome modification may be to a transgene. In some embodiments, the at least one gene for which expression is modified may be a transgene.

In some embodiments, each pair of hybridizing synthetic nucleic acid constructs that are introduced is orthogonal to (independent of) one another and forms different synthetic CRISPR nucleic acid-tracr nucleic acid hybrids from any other pair of hybridizing synthetic nucleic acid constructs that may be introduced into the cell. In some embodiments, the CRISPR nucleic acid and tracr nucleic acid of each orthogonal pair of hybridizing synthetic nucleic acid constructs do not hybridize to the CRISPR nucleic acid and tracr nucleic acid of any other introduced pair of hybridizing synthetic nucleic acid constructs to form a synthetic CRISPR nucleic acid-tracr nucleic acid hybrid having a secondary structure that forms a complex with a CRISPR-Cas effector protein. In some embodiments, the crRNAs and tracrRNAs of at least two pairs of hybridizing synthetic nucleic acid constructs that are introduced may weakly or inefficiently hybridize to form synthetic CRISPR nucleic acid-tracr nucleic acid hybrids having mismatches for use in, for example, fine-tuning the activity of a CRISPR-Cas effector protein (e.g., nuclease, activation, repression, etc.) against specific targets or to generate different levels of activation/repression/cutting.

In some embodiments, at least two pairs of hybridizing synthetic nucleic acid constructs form a synthetic CRISPR nucleic acid-tracr nucleic acid hybrid having a secondary structure that is different from a secondary structure formed by any other introduced pair of hybridizing synthetic nucleic acid constructs, and which forms a complex with a first CRISPR-Cas effector protein that is different from a second CRISPR-Cas effector protein, which forms a complex with the synthetic CRISPR nucleic acid-tracr nucleic acid hybrids formed by any other pair of hybridizing synthetic nucleic acid constructs introduced into the cell.

In some embodiments, each pair of at least two pairs of hybridizing synthetic nucleic acid constructs forms a synthetic CRISPR nucleic acid-tracr nucleic acid hybrid having a secondary structure that complexes with the same CRISPR-Cas effector protein.

In some embodiments, the methods of the invention comprise introducing at least two pairs of hybridizing nucleic acid constructs of the invention and a Type II or Type V CRISPR-Cas effector protein, or a nucleic acid construct encoding a Type II or Type V CRISPR-Cas effector protein, wherein the Type II or Type V CRISPR-Cas effector protein forms a complex with the synthetic CRISPR nucleic acid-tracr nucleic acid hybrid formed by each of the at least two pairs of hybridizing synthetic nucleic acid constructs. In some embodiments, each pair of the at least two pairs of hybridizing synthetic nucleic acid constructs that are introduced may be orthogonal to (independent of) one another and forms different synthetic CRISPR nucleic acid-tracr nucleic acid hybrids from any other pair of hybridizing synthetic nucleic acid constructs that is introduced into the cell. In some embodiments, the CRISPR nucleic acid and tracr nucleic acid of each orthogonal pair of hybridizing synthetic nucleic acid constructs do not hybridize to the CRISPR nucleic acid and tracr nucleic acid of at least one other pair of hybridizing synthetic nucleic acid constructs to form a synthetic CRISPR nucleic acid-tracr nucleic acid hybrid. In some embodiments, the CRISPR nucleic acid and tracr nucleic acid of each orthogonal pair of hybridizing synthetic nucleic acid constructs do not hybridize efficiently to the CRISPR nucleic acid and tracr nucleic acid of at least one other pair of hybridizing synthetic nucleic acid constructs to form a synthetic CRISPR nucleic acid-tracr nucleic acid hybrid.

In some embodiments, at least one pair (a first pair) of hybridizing synthetic nucleic acid constructs forms a first synthetic CRISPR nucleic acid-tracr nucleic acid hybrid having a secondary structure that is different from a secondary structure formed by at least one other pair (a second pair, third pair, fourth pair, fifth pair, etc.) of hybridizing synthetic nucleic acid constructs introduced into the cell, wherein the first synthetic CRISPR nucleic acid-tracr nucleic acid hybrid forms a complex with a first Type II and/or Type V CRISPR-Cas effector protein that is different from a second Type II and/or Type V CRISPR-Cas effector protein that forms a complex with the synthetic CRISPR nucleic acid-tracr nucleic acid hybrid formed by the at least one other pair of hybridizing synthetic nucleic acid constructs introduced into the cell.

In some embodiments, each pair of at least two pairs of hybridizing synthetic nucleic acid constructs forms a synthetic CRISPR nucleic acid-tracr nucleic acid hybrid having a secondary structure that may complex with the same Type II or Type V CRISPR-Cas effector protein, optionally wherein the Type II or Type V CRISPR-Cas effector protein is from the same wild type Type II or Type V CRISPR-Cas system.

In some embodiments, a Type II or Type V CRISPR-Cas effector protein is a dCRISPR-Cas effector protein (e.g., dCas9, dCas12b) having an inactive HNH and inactive RuvC (Type V— inactive RuvC).

In some embodiments, a Type II or Type V CRISPR-Cas effector protein may be an active Type II or Type V CRISPR-Cas nuclease (e.g., Cas9, Cas12b). In some embodiments, a Type II or Type V CRISPR-Cas effector protein may be a Type II or Type V CRISPR-Cas nickase (e.g., Cas9n, Cas12bn). In some embodiments, a Type II or Type V CRISPR-Cas effector protein may be a deactivated/dead Type II or Type V CRISPR-Cas effector protein (e.g., dCas9, dCas12b).

In some embodiments, the CRISPR nucleic acid and tracr nucleic acid of each pair of hybridizing synthetic nucleic acid constructs are operably linked to promoters that are different from the promoters that are operably linked to a CRISPR nucleic acid or a tracr nucleic acid of any other pair of hybridizing synthetic nucleic acid constructs introduced into the cell. In some embodiments, the CRISPR nucleic acid and tracr nucleic acid of at least one pair of hybridizing synthetic nucleic acid constructs are operably linked to at least one promoter that is the same as at least one promoter that is operably linked to a CRISPR nucleic acid or a tracr nucleic acid of another introduced pair of hybridizing synthetic nucleic acid constructs. Various configurations of promoters and CRISPR nucleic acid and/or a tracr nucleic acid constructs of the hybridizing pairs may be used to provide altered expression of a target nucleic acid or gene, for example, the same promoter may be used to restrict the expression of the crRNAs and tracrRNAs to specific tissue types. Thus, some embodiments of the invention provide selecting pairs of hybridizing synthetic nucleic acid constructs for modifying the expression of two or more nucleic acids.

In some embodiments a wild type Type II CRISPR nucleic acid-tracr nucleic acid may be a wild type Type II CRISPR nucleic acid and a wild type Type II tracr nucleic acid from, for example, *Lactobacillus* spp. Type II system, a *Bifidobacterium* spp. Type II system, a *Staphylococcus* spp. Type II system, a *Neisseria* spp. Type II system, a *Campylobacter* spp. Type II system, a *Kandleria* spp. Type II system, a *Leuconostoc* spp. Type II system, an *Oenococcus* spp. Type II system, a *Pediococcus* spp. Type II system, a *Streptococcus* spp. Type II system, a *Weissella* spp. Type II system, and/or a *Olsenella* spp. Type II system. In some embodiments, a wild type Type II CRISPR nucleic acid-tracr nucleic acid may be a wild type Type II CRISPR nucleic acid and a wild type Type II tracr nucleic acid from *Streptococcus pyogenes* or *Streptococcus thermophilus.*

In some embodiments a wild type Type V CRISPR nucleic acid-tracr nucleic acid may be a wild type Type V CRISPR nucleic acid and a wild type Type V tracr nucleic acid from, for example, an *Alicyclobacillus* spp. Type V system, a *Oleophilus* spp. Type V system, and/or a *Deltaproteobacteria* spp. Type V system, optionally where the *Alicyclobacillus* spp. Type V system may be from *Alicyclobacillus acidoterrestris*, the *Deltaproteobacteria* spp. Type V system may be from *Deltaproteobacteria bacterium.*

In some embodiments, the invention provides organisms and cells from organisms comprising a logic-gate-based system of the invention and/or at least one pair or at least two pairs of hybridizing nucleic acid constructs of the invention. In some embodiments, the cells may be cells from any organism. Non-limiting examples of organisms useful with the present invention are bacteria, archaea, fungi, plants, animals including mammals (e.g., primates, cattle, sheep, goats, horses, dogs, cats, or rodents (e.g., mice, rats, gerbils, guinea pigs)), insects, and/or birds. In some embodiments, the organism may be a human primate or a non-human primate.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Currently, research in the life sciences is highly restricted by the choice of promoters available to drive the expression of genes of interest in complex patterns and at desired levels. As provided herein, a series of programmable CRISPR-based synthetic genetic circuits capable of integrating multiple inputs are constructed from previously described synthetic and natural promoters to generate novel expression patterns. This technology allows the generation of many hundreds of orthogonal genetic components that in combination can perform complex logic operations.

Example 1

Five Spy (working with the Cas9 from *S. pyogenes*) and five Sib (working with the Cas9 from *S. thermophiles* CRISPR1) complementary gRNA pairs have been designed (FIGS. 9A-9B). Parameters that are likely to influence the activity of the crRNA:tracrRNA pairs (e.g. the number of mismatches and their relative position in the lower stem) as well as intra-species cross-reactivity among the pairs are tested using 25 (5×5) Spy and 2:5 (5×:5) Sthl cross-pair gRNA combinations. These pairs provide twenty five different combinations harboring 0, 1, 2, 3, 4 or 5nt mismatches at different relative positions in the lower stem (FIGS. 9A-911). Two different Cas9 systems (e.g., from Spy and Sth1) are used, which utilize different PAM sequences and rely on divergent crRNA:tracrRNA structures (FIGS. 9A-9B), thus doubling the total number of orthogonal genetic devices that can be generated and enabling a simple design of complex gates such as XNOR and XOR (FIGS. 10A-10B). In addition to testing the orthogonality of different crRNA:tracrRNA pairs with different mismatches, a complete AND gate module is assembled that consists of four types of transcriptional units (TUs). The AND gate module includes a dCas9, crRNA, tracrRNA and a reporter TU (Table 1) and is tested for functionality (in terms of activating a reporter, as compared in strength to the corresponding WT control (Table 1)). Lack of cross-reactivity is tested (see, Example 1 and Example 2 in Table 1 corresponding to one matching and one mismatching Spy gRNA combination) in transiently co-transformed plants using agroinfiltration of tobacco leaves. Fluorescence is evaluated qualitatively using fluorescence microscopy.

Using the two best performing Spy (for example, modules A, B) and two Sthl (modules C, D) crRNA:tracrRNA pairs from the transient expression experiments above, four inter-species (AC, AD, BC, BD, see e.g., module AC in Table 1) and two intra-species (AB and CD, see, e.g., module AB in Table 1) pairwise combinations are tested for functionality and orthogonality in stable transformations, Multi-TU constructs including a selectable marker are assembled by GB and transformed into Arabidopsis using the flower dip method.

The number of potential orthogonal pairs that can be generated using the compositions and methods of the present invention may be affected by the number of mismatches required to confer orthogonality, the positional effect of such mismatches, and the functional equivalence of the G-U base pairs. However, as an example, allowing G-Li base pairing, requiring 1 or more mismatches to confer orthogonality, and using the *S. pyogenes* short lower stem), a conservative estimate provides 32 orthogonal pairs that may be simultaneously expressed in a single cell. This number may be increased to 126 orthogonal pairs if the 7 base pairs of the longer lower stem of the crRNA-tracrRNA complex from *S. thermophilus* CRISPR1 is utilized. Further, this number may be as high as 4096 if only one mismatch is required for conferring orthogonality and G-U pairs in the lower stem were to disrupt the activity of the crRNA-tracrRNA complex. Thus, even with the most conservative estimates, the number of orthogonal modules than can be created with this new system is several times higher than anything that has been achieved previously using different systems.

Example 2. Modifying Gene Regulation in Auxin Biosynthesis

The present invention provides new molecular tools to precisely control the patterns and levels of gene expression. These tools are applied as described below to address the long-standing question of the role of local auxin production in root development using the synthetic CRISPR tools of the present invention to precisely manipulate gene expression. The compositions and methods provided by the present invention have broad applications beyond the study of auxin biosynthesis and can be applied to restrict or tune the expression of traits of interest such that the underlying gene(s) is/are turned "on" or "off" only when preset combinations of conditions (environmental, developmental, spatial, etc.) are met.

Auxin is a major phytohormone that controls a wide variety of developmental processes in plants, including the establishment of root architecture and root meristem maintenance. In roots, local auxin biosynthesis and transport play overlapping roles in the generation of robust morphogenic auxin gradients that instruct root development. To delineate the role of locally produced auxin in controlling root architecture, the CRISPR-based compositions and methods of the invention are developed to restrict the expression of auxin biosynthesis genes driven by tissue-specific yet leaky promoters to the root cell types of interest. The new tools take advantage of crRNA:tracrRNA hybrid pairs to combine inputs from two different drivers/promoters and delimit where a dCas9-based synthetic transcription factor activates or represses expression of a target nucleic acid or gene (in this example, an auxin biosynthesis gene). This approach is based on the generation of two or more pseudo-orthogonal gRNA pairs and is compatible with the construction of all basic logic gates to produce multiple derived patterns of expression. This strategy is not only scalable, but also enables tuning of the output gene expression levels, thus providing an unprecedented degree of flexibility.

The vast majority of tissue-specific markers in plants, including those that mark different cell lineages in roots, are also expressed elsewhere. For example, based on public microarray and RNA-seq data, root markers SHR, SCR, WOL, CO2, EN7, CVP2, ATHB8, TMO5, and CYCD6 are also highly expressed in several aerial organs and WOX5, COBL9/SHV2, WER, FEZ, SMB, IRT1 and GL2 are somewhat expressed in aerial tissues in addition to roots. Non-exclusive (i.e. multi-tissue/organ) or leaky expression of marker genes is a major limitation for many studies, from transgene complementation analyses to "cell-type specific" omics approaches on sorted protoplasts, with the results of such studies being only as reliable as the specificity of the drivers employed. Besides the obvious specificity concern, the "fixed" (i.e. non-tunable) strength of existing drivers further complicates the interpretation of the data. For example, if in a genetic complementation experiment, the auxin biosynthetic gene WEI8 driven by a strong promoter in tissue A complements the auxin deficient wei8 tar2 double mutant better than WEI8 driven by a weaker promoter in tissue B, the difference in the complementation ability can be attributed to either the difference in the expression pattern or to that in the strength of the drivers (or a combination of both). Finally, for some tissue/cell types, marker choices may be limited. To increase cell-type expression specificity, genetic logic gates can be used to activate the output gene(s) only when two or more different tissue-specific input genes are active in the same cell (logic AND gates). The main limitation of this approach, however, is that only a handful of orthogonal gate components are currently available, restricting the ability to generate genetic circuits capable of integrating multiple signals. To address this limitation, new easily programmable and scalable tools were developed as described herein to confer greater specificity and "tunability" to the drivers and to generate novel patterns of expression not currently achievable with the existing natural or synthetic promoters/markers/drivers. The new synthetic genetic devices described herein are used in this Example to induce auxin biosynthesis in specific cell types of the Arabidopsis auxin-deficient mutant wei8 tar2and to repress auxin production in specific cell types of tomato roots to unequivocally address the long-standing question on the role of local auxin biosynthesis in root development in two important plant reference systems.

Experimental strategy: To confer highly restricted patterns of expression that are more specific than those attainable with the existing drivers, undesired domains of expression from available drivers are "subtracted" by relying on the co-expression of two or more genes that overlap in their expression patterns only in the domain of interest; in other words, to increase specificity by using genetic logic AND gates. CRISPR/Cas9 has emerged as a versatile molecular technology to not only induce targeted mutations in a genome, but also to regulate expression of genes of interest by fusing a nuclease-dead version of Cas9, dCas9, to transcriptional activator (dCas9-AD) or repressor (dCas9-RD) domains and targeting these synthetic transcription factors to promoters of the genes of interest by designing guide RNAs (gRNAs) that recognize 20nt regions (protospacers) in the promoters of the genes of interest.

In native CRISPR/Cas9 systems (e.g., those of *Streptococcus pyogenes* (Spy) and *S. thermophilus* CRISPR1 (Sth1)), two different small RNAs, crRNA and tracrRNA, assemble to form a dual gRNA (FIGS. 9A-9B) to target the Cas9 protein to a complementary region on a DNA molecule. In the present example, instead of using a simplified engineered chimeric single gRNA to direct the dCas9 transcription factor to the promoters of interest, several modified versions of the original crRNA:tracrRNA dual gRNA pairs and their derivatives are used (FIGS. 9A-9B). crRNA and tracrRNA pair through a complementary region, and disruption of this base-pairing via mutations in as few as 2nt in the guide RNA blocks the Cas9 activity. However, restoration of base-pairing via complementary mutations enables assembly/folding of functional gRNA and restores Cas9 activity.

Thus, a set of mutant complementary crRNA:tracrRNA pairs are developed that support the activity of Cas9, but which fail to pair with wild-type and other mutant versions of gRNAs (FIGS. 9A-9B, 14, 15, 16, 17, 18, 19 and 20). The large number of possible orthogonal pairs are then exploited to generate sets of not cross-reacting genetic devices capable of performing complex logic operations on specific biological tasks, including, for example, restricting expression of the output gene(s) via leaky signal subtraction.

The structure-function relationships of well-defined motifs of the crRNA:tracrRNA pair (FIGS. 9A-9B) have been extensively characterized in several Cas9 systems including those of Spy and Sth1. crRNA and tracrRNA pair with one another through their 3' and 5' regions, respectively, forming an imperfect hairpin comprised of a lower stem, a bulge, and an upper stem (FIGS. 9A-9B). The upper stem is involved in gRNA processing, is largely dispensable for the function of mature gRNA, and can be shortened to just 5 complementary base pairs. Furthermore, mutations that change the upper loop sequence but do not disrupt the crRNA:tracrRNA base pairing are well tolerated. In contrast, the bulge and the lower stem appear to be essential for Cas9/crRNA:tracrRNA complex function and mutations that change the sequence and disrupt the base pairing of the lower stem abolish Cas9 activity. Remarkably, drastic complementary changes in the lower stem sequences that nonetheless fully preserve the crRNA:tracrRNA base pairing do not interfere with the Cas9 function. This property can be used to design mutant crRNA and tracrRNA pairs that support the activity of Cas9 when co-expressed together but not when co-expressed with their non-complementary counterparts, thereby developing a set of non-cross-interacting crRNA and tracrRNA pairs (FIGS. 9A-9B). The ease with which large numbers of orthogonal pairs can be created using this novel approach represents a key advantage of the proposed system and opens the possibility of designing large molecular circuits comprised of dozens of non-cross-interacting logic gates.

To confer stimulus-regulated or tissue-specific expression to crRNA and tracrRNA in living cells, RNA Polymerase II (RNAPII) promoters may be employed to drive their expression. However, RNAPII-transcribed transcripts normally get capped in the 5', cleaved in the 3', polyadenylated and exported out of the nucleus, which may interfere with the crRNA and tracrRNA function. Although several systems are available to solve this problem, RNA endoribonuclease Csy4 from *Pseudomonas aeruginosa* has recently been shown to be more efficient at processing transcripts than either the ribozyme or tRNA-based systems (Čermák et al., 2017. *Plant Cell* 29(6): 1196-1217). Thus, for this example, both components of a crRNA:tracrRNA pair are expressed under synthetic or native RNAPII-controlled promoters of interest to drive activation (or repression) of output genes (in this Example, encoding auxin biosynthesis enzymes) by targeting dCas9-AD (or dCas9-RD) to their promoters specifically in the tissues where both crRNA and tracrRNA are co-expressed. Additionally, combinations of multiple pseudo-orthogonal crRNA:tracrRNA pairs can be combined to perform more complex logic functions, such as achieving high degree of tissue specificity or creating novel patterns of gene expression.

Some of the capabilities of this system can be illustrated by expressing tracrRNA under a synthetic ethylene-inducible promoter 10xEBSp and crRNA under a QC-specific promoter WOX5p[9] (Sarkar et al., 2007. *Nature* 446: 811-814) and by fusing a 35Sp-driven dCas9 to the VPR transcriptional activation domain (FIG. 10A-10B). The resulting logic AND gate will lead to the activation by ethylene of the GFP reporter gene exclusively in the QC of the root.

Functionality and orthogonality of mutant crRNA: tracrRNA pairs (5 Spy and 5 Sth1) in Arabidopsis and tomato. We have designed five Spy and five Sth1 complementary gRNA pairs. Of the 25 (5×5) Spy and 25 (5×5) Sth1 cross-pair gRNA combinations that will be tested for intra-species cross-reactivity, various combinations will harbor 0, 1, 2, 3, 4 or 5nt mismatches at different relative positions in the lower stem (FIGS. 9A-9B). We have chosen to work with two different Cas9 systems (from Spy and Sth1, that utilize different PAM sequences and rely on divergent crRNA: tracrRNA structures) (FIGS. 9A-9B), thus doubling the total number of orthogonal genetic devices that can be generated and enabling a simple design of complex gates such as XNOR and XOR. DNA synthesis and a system based on type IIS restriction enzymes (e.g., GoldenBraid (GB) molecular cloning technology) is used make the DNA constructs Specifically, four types of transcriptional units (TUs) are assembled that together constitute a single genetic module representing an AND gate. Each module includes a dCas9, crRNA, tracrRNA and a reporter TV (Table 1) and is tested for functionality (e.g., in terms of activating a reporter, as compared in strength to the corresponding WT control (Table 1)) and lack of cross-reactivity (see, Example 1 and Example 2 in Table 1 corresponding to one of the matching and one mismatching Spy gRNA combinations) in transiently co-transformed plants using Arabidopsis and tomato mesophyll protoplasts and/or tobacco epidermis.

Fluorescence is evaluated qualitatively using fluorescence microscopy, as well as quantitatively using fluorescence-activated cell sorting (FACS) for protoplasts and a plate reader (fluorometer) for tobacco cells. In all cases, an ACT2 promoter driving the TagBFP blue fluorescent protein gene is used as an internal transformation control. The two best performing Spy (for example, modules A, B) and two Sth1 (modules C, crRNA:tracrRNA pairs, four inter-species (AC, AD, BC, BL), see, an example of a hypothetical module combination AC in Table 1) and two intra-species (AB and CD, see, an example of a hypothetical module AB in Table 1) pairwise combinations are tested for functionality and orthogonality in stable transformations. The multi-TU constructs include a selectable marker, are assembled by GB and transformed into Arabidopsis using the flower dip method.

Logic gates in stable transformants. To evaluate the versatility of the CRISPR-based system of the present invention as a new synthetic biology tool and to generate novel spatiotemporal patterns of expression, in addition to making the AND gates, we will also generate (I) universal NOR and NAND gates and a complex XOR logic gate as shown in FIGS. 10A-10B and (2) combine two AND gates to remove all shoot-specific expression of 10xEBSp and WOX5p (FIG. 11, upper panel). We have chosen to focus on the AND, NOR and NAND gates because of the utility of the gene expression patterns that these generate (FIGS. 10A-10B) and the universality of NOR and NAND (I.e., either of these gates by itself can implement any logic function without the need for additional logic gates). We also include a much more complex XOR gate to demonstrate that our CRISPR-based system is capable of producing any logic gate. For the dual AND gate circuit (FIG. 12, upper panel), a root-specific promoter of RG12/RCH1 (At5g48940)[33] that is expressed only in root tips including QC will be used (e.g., Casamitjana-Martinez et al., 2003. Curr. Biol. 13: 1435-1441). These logic gates are stably transformed into the short-generation Arabidopsis system.

To infer the effectiveness of the system at removing expression in non-root tissues, comparisons are made with the expression patterns of the reporter gene from the experiments with single and double AND gates. To maximize both the sensitivity and spatial resolution, both GM' and GUS' reporters are used as the outputs. Microscopy is employed to evaluate the derived root-specific patterns of expression of the output reporters.

crRNA-tracrRNA system applied to address the role of local auxin biosynthesis in root development in tomato and Arabidopsis. Using the AND, NOR and NAND logic gates, the auxin biosynthesis gene WEI8 is expressed with different patterns of expression (FIG. 10A-10B) in the auxin deficient wei8 tar2mutant background by replacing the reporter with GFP-WEI8 in the output construct. The ability of the different modules, and thus of WE/8 expression patterns, to complement the auxin deficient mutant is assessed in stably transformed Arabidopsis plants in air versus in ethylene. The primary focus is on evaluating auxin-dependent root phenotypes (e.g., meristem maintenance (plus/minus NPA), lateral root initiation and elongation, and ethylene-mediated root growth inhibition), however, complementation of other auxin defects is also examined. To further restrict the expression of GFP-WEI8 to the root tissues, an alternative three-input AND gate approach (FIG. 12, lower panel) to the double AND gate circuit is employed (FIG. 12, upper panel).

To dissect the role of auxin biosynthesis in tomato, equivalent gates to those used to manipulate GFP-WEI8 expression in Arabidopsis are used to repress in specific root tissues the transcriptional activity of the tomato Solyc06g071640 (a tomato WEIS/TAR orthologue highly expressed in roots). The synthetic 10xEBSp and SlWOX5pro are used to drive the crRNA and tracrRNA inputs for the AND, NOR and NAND logic gates. In contrast to our work in Arabidopsis where WEI8 activity is restored in specific tissues of a mutant (FIG. 10A-10B), in tomato the repressor version of dCas9, $dCas9_{Spy}$-SRDX, is targeted to the promoter of the Solyc06g071640 endogenous gene using a set of gene-specific crRNA constructs to repress the expression of this auxin biosynthetic gene in desired patterns. Ten and thirty NGG PAMs are in the 0.2 kb and 1.0 kb immediately, upstream of this transcription start site of Solyc06g071640, respectively, that can be used for designing crRNA constructs. The effectiveness of the repression achievable with this system can be assessed by qRT-PCR on dissected roots and shoots in the presence and absence of ethylene.

Similar approaches to those described above can be used to take advantage of any stimulus-regulated or stage/tissue-specific promoters (native or synthetic) in any "transformable" species. Furthermore, with the design exemplified above, the number of logic gate combinations can be further increased by employing two orthogonal versions of dCas9 (e.g., from Spy and Sth1, that work exclusively with their own crRNA:tracrRNA partners) and, in some instances, by also using single gRNAs, in theory enabling the construction of a complete set of logic gates (FIG. 10A-1.0B). Finally, the proposed use of synthetic promoters based on the multimerization on of crRNA target sequences (protospacers) offers an additional advantage of allowing for the fine-tuning of the levels of expression of genes of interest by varying the number of protospacer sequences in their promoters. The simplicity by which large numbers of orthogonal logic gates can be generated with the proposed crRNA:tracrRNA system opens the possibility of developing highly programmable agricultural traits. These traits would be expressed/realized only when a predetermined set of conditions (environmental, developmental, tissue-type, etc.) is met or, in other words, when a number of native and/or synthetic promoters are active or, vice versa, inactive in a specific preset combination.

Example 3

A Cas9 nuclease that retains its nucleic acid binding and nuclease activities may be used as described herein. In an example of an AND gate, use of an active Cas9 nuclease in combination with the constructs, system and methods of the present invention, the outputs of crRNA-tracrRNA-Cas9 complex binding to the targeted region in the DNA are double-stranded DNA cuts that occur only in specific cell types or under specific conditions where all three components (crRNA, tracrRNA, Cas9) are concomitantly expressed. Upon the use of, for example, a repetitive genomic element (e.g., a transposon) as the targeted protospacer, multiple cuts are triggered in the genome and such profound DNA damage is expected to lead to targeted cell death specifically in the cells/tissues that co-express the input logic AND gate constructs.

If one or more promoters driving the crRNA, tracrRNA, and/or Cas9 components of the logic gate are locally induced, for example, by pathogen attack at the site of infection, then the resulting DNA cleavage and cell death are expected to occur specifically at the infected site, mimicking the hypersensitive response and preventing the spread of the pathogen. A similar scenario can be envisioned for selectively destroying cancer cells (without affecting normal healthy tissues) based on the co-expression of several logic gate inputs that uniquely mark only cancerous cells.

Another example is the induction of homologous recombination at the sites of Cas9-induced DNA cleavage in a specific subset of cells (exclusively marked by the activity of the crRNA-tracrRNA pair) to introduce the desired transgene only in the cells of interest.

Example 4

As disclosed herein, the compositions and methods of the present invention have a very broad spectrum of applications. For example, in agriculture, this system could be used to drive the expression of, for example, BT toxin only in specific tissues (leaves, but not flowers), induced, for example, when a specific non-toxic chemical is applied. To achieve this specificity, tissue-specific promoters in the plant species of interest as well as promoters that are modulated by the non-toxic chemical are employed.

In some instances, organ specific promoters may not be available. However, this may be overcome by subtracting the expression in any unwanted tissues/patterns using other tissue specific promoters with the constructs, system and methods of the present invention. As an example, leaf specificity may be achieved in the absence of a leaf-specific promoter by using a promoter that has broad expression patterns (for example, expressed in leaves and flowers) and subtracting the expression in any unwanted tissues/patterns using, for example, a promoter that is active only in flowers. In this example, an A NOT B gate could be used to subtract the flower expression from the leaf-and-flower promoter. The output of this gate could then be combined through an AND gate with a promoter that is induced by a non-toxic chemical to activate BT expression only in leaves treated with, for example, a non-toxic agrochemical.

Example 5

Using transient assays in tobacco epidermis using the *Streptococcus pyogenes* (Spy) CRISPR/Cas9 system, we have demonstrated the validity of our CRISPR-based logic gate design and showed that the precise base pairing between crRNA and tracrRNA in the lower stem of the dual gRNA base paired region (the "handle") is required for Cas9 activity. We showed that mutations in as little as one or two base pairs greatly reduce and in two to five base pairs abolish Cas9 function in the context of synthetic transcriptional activator, dCas9-AD. In addition, we demonstrated that complementary mutations that restore the base pairing in the lower stem of the dual gRNA reactivate the dCas9 effector. Thus, the present invention allows us to make multiple (e.g., 2, 3, 4, 5, 6, 7, 8, 9, 10, 11, 12, 13, 14, 15, or 16) orthogonal dual gRNA pairs with three or more mismatches relative to other pairs that can co-exist in the same cell and regulate multiple target nucleic acids or genes independently through a single dCas9-based transcriptional effector.

In this example, additional experiments were directed at (1) testing the effect of upper stem mutations in the handle region (to further expand the repertoire of fully and/or partially orthogonal gRNA pairs that can be generated), (2) testing the use of RNA polymerase II promoters to drive gRNA components (to enable the use of tissue-specific or stimulus-regulated promoters in our logic gate designs), and (3) establishing the dual gRNA CRISPR system with the *S. thermophilus* version of the CRISPR components (to demonstrate the universality of our dual gRNA approach in the generation of logic devices and to enable an even wider variety of orthogonal devices that can be co-expressed at the same time to control different target nucleic acids.

(1) To evaluate the effect of upper stem mutations in the handle region, we swapped the 12 nucleotides above the bulge of the handle between crRNA and tracrRNA to produce crRNA$_{usm}$ and tracrRNA$_{usm}$ (usm=upper stem mutation). Our expectation was that this sequence swap will not interfere with the transcriptional activity of dCas9-AD because the upper stem of the gRNA handle does not make contact with Cas9 (Nishimasu et al. Cell 156: 935-949 (2014)) and the base pairing between the small RNAs was maintained in our redesign. In fact, the resulting crRNA$_{usm}$ and tracrRNA$_{usm}$ with the retained complementarity of the upper stem remained fully functional and comparable in their activity to their wild-type counterparts, crRNAwT and tracrRNAwT (FIG. 20, top panels). This sequence swapping lead to a 12 bp mismatch between crRNAwT and tracrRNA$_{usm}$, or between crRNA$_{usm}$ and tracrRNAwT, leading to a strong reduction or a complete loss of dCas9 transcriptional effector activity in the two mismatched combinations, respectively (FIG. 20, bottom panels). This result indicates that not only the lower, but also the upper stem of the dual gRNA handle region can be leveraged to tune down or abolish the transcriptional activity of the dCas9-AD-containing ribonucleoprotein complex, further expanding the number of possible orthogonal combinations of crRNA and tracrRNA that can be developed with this system.

Figure 21:
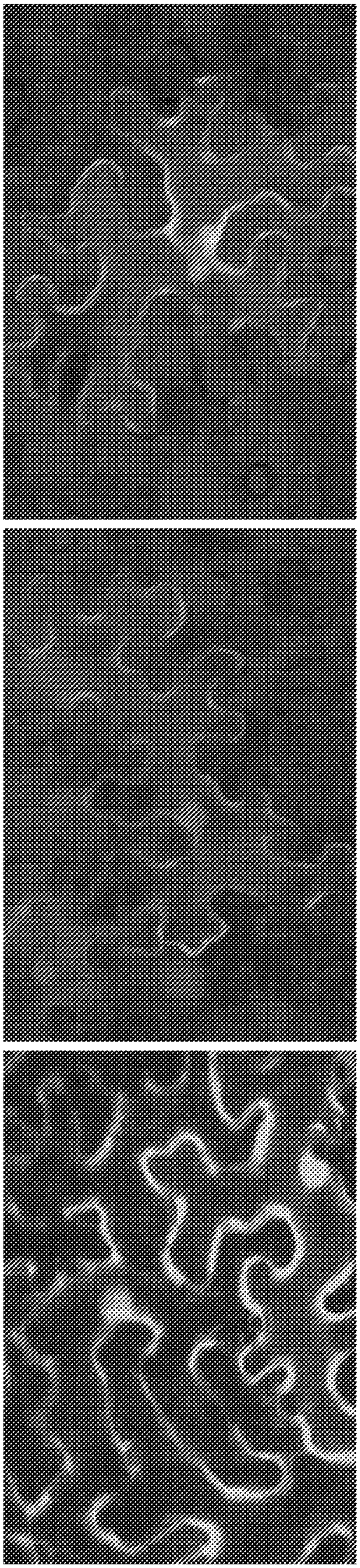
FIG. 21. The *S. pyogenes* dual gRNA CRISPR system is active when crRNA is driven by an RNA Pol II promoter 35Sp. The positive control construct harbors crRNA and tracrRNA driven by the U6p promoter (left panel). The 35Sp-driven crRNA is flanked either by the hammerhead (HH) and hepatitis delta virus (HDV) ribozymes (middle panel) or by tRNA intron (right panel) to enable crRNA processing that removes the 5' cap and the poly(A) tail (which is a prerequisite of the construct's nuclear retention). All other parts of the logic gate are the same, including the U6p-driven crRNA, 35Sp-driven dCas9 fused to the EDLL transcriptional activation domain, 35Sp-driven MS2 coat protein gene fused with a VPR transcriptional activation domain, and SlDFRp-driven mCherry reporter. The absolute strength and the pervasiveness of the mCherry reporter activation in the 35Sp-containing combinations (middle and right panels) may not be maximized in this experiment relative to the U6p control (left panel) due to the system components being split into three constructs (two panels on the right), as compared to a single, combined positive control construct (left panel).

(2) Our initial work utilized an RNA polymerase III promoter AtU6p to drive both crRNA and tracrRNA. To be able to take advantage of natural developmental stage- and tissue-specific promoters or synthetic and natural stimulus-regulated promoters in our logic gate designs, we also wanted to show the usefulness of RNA polymerase III promoters. Here, we employed the Cauliflower Mosaic Virus promoter 35Sp, the gold standard in transgenic work in plants. Problematically, RNA polymerase II transcripts are known to get capped, polyadenylated and exported out of the nucleus (Bentley *Nat Rev Genet* 15(3): 163-175 (2014)), whereas we needed the crRNA and tracrRNA to remain in the nucleus in order to regulate gene expression via dCas9-AD. Therefore, we employed the previously reported tRNA introns (ermak et al., *The Plant Cell,* 29(6), 1196-1217) (2017)) and ribozymes (Gao and Zhao, *Journal of Integrative Plant Biology,* 56(4), 343-349 (2014)) that upon processing cut out the active part of crRNA. 35Sp-driven crRNAwT flanked by either Hammerhead (HH) and Hepatitis Delta Virus (HDV) ribozyme sequences or by tRNA introns was functional in combination with U6p-driven tracrRNAwT and dCas9-AD, leading to the activation of the reporter mCherry (FIG. 21). Further optimizing of the system may be provided by increasing (1) the nuclear retention of the crRNA transcript, (2) the base pairing of cr/tracrRNA, and (3) the transcriptional activation potential of the system.

(3) Finally, we worked on establishing the dual gRNA transcriptional activation system with *S. thermophilus* (Sth) components that have not been previously implemented in plants. To our knowledge, only the gene editing activity of Cas9$_{Sth}$ working through a single gRNA has been reported to date (Steinert et al. *Plant J* 84(6):1295-1305 (2015)). We succeeded at converting Cas9$_{Sth}$ to dCas9$_{Sth}$-AD by introducing D9A/H599A amino acid substitutions (analogous to those of dCas9$_{Spy}$ D10A/H840A (Jinek et al., *Science* (*American Association for the Advancement of Science*), 337(6096), 816-821 (2012)) to disarm its nuclease activity and by fusing the EDLL activation domain (Tiwari et al., *The Plant Journal: For Cell and Molecular Biology,* 70(5), 855-865 (2012)) in its C-terminus to confer a transcriptional activation function. We have tested this novel dCas9$_{Sth}$-AD construct in combination with the previously reported U6p-driven single gRNA (Agudelo et al., *Genome Research,* 30(1), 107-117 (2020)), leading to a strong transcriptional activation of an mCherry reporter (FIG. 22), confirming the functionality of all of the parts in our system. We then went on to split single gRNA$_{Sth}$ into crRNA$_{Sth24}$ and tracrRNA$_{Sth24M}$. We were able to detect a moderate level of activity of the dual gRNA$_{Sth}$ components that is much lower than that observed with single gRNA$_{Sth}$ (FIG. 22), confirming the functionality of the system. Computational predictions of the dual gRNA$_{Sth}$ components point to these two small RNA molecules folding intramolecularly in a manner that interferes with the desired intermolecular base pairing of crRNA$_{Sth24}$ with tracrRNA$_{Sth24M}$ via the handle region and of crRNA$_{Sth24}$ with the protospacer in the target promoter (FIG. 23, top panel). Alternative crRNA$_{SthN2}$ and tracrRNA$_{SthN2}$ pairs were designed with minimal intramolecular folding (FIG. 23, bottom panel) and maximum preferred intermolecular base-pairing.

Exemplary Sequences Used in the Examples Include the Following:

1. *S. pyogenes*-based short (processed) crRNA targeting SIDFR protospacer, version 1:

(SEQ ID NO: 9)

Figure 16:
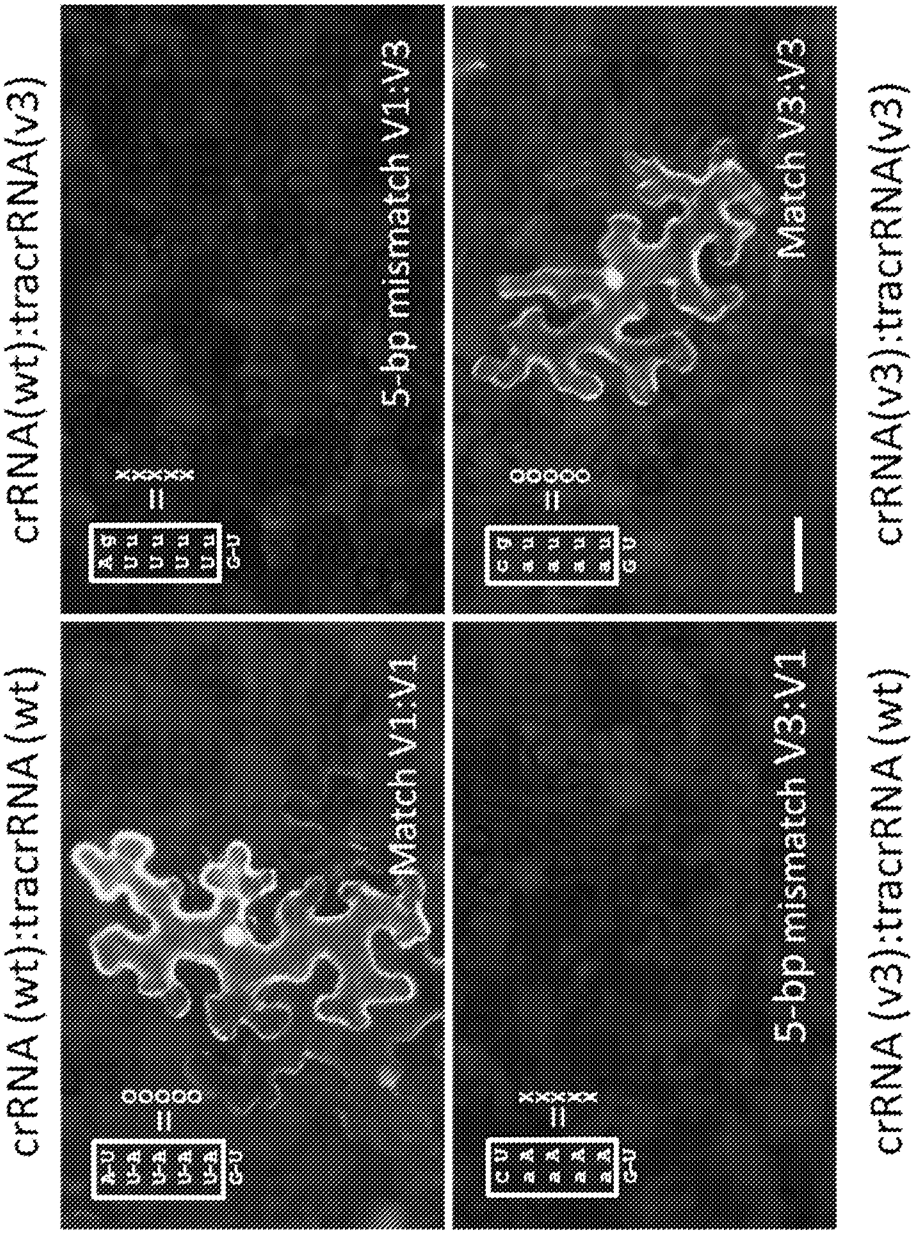
FIG. 16 provides an illustrative example of the orthogonality of the CRISPR-Cas logic gate system of the invention. Here, both matching WT:WT and Mut:Mut combinations activate the mCherry reporter, whereas the two reciprocal non-complementary combinations with 5 mismatches in the lower stem region do not.
Figure 17:
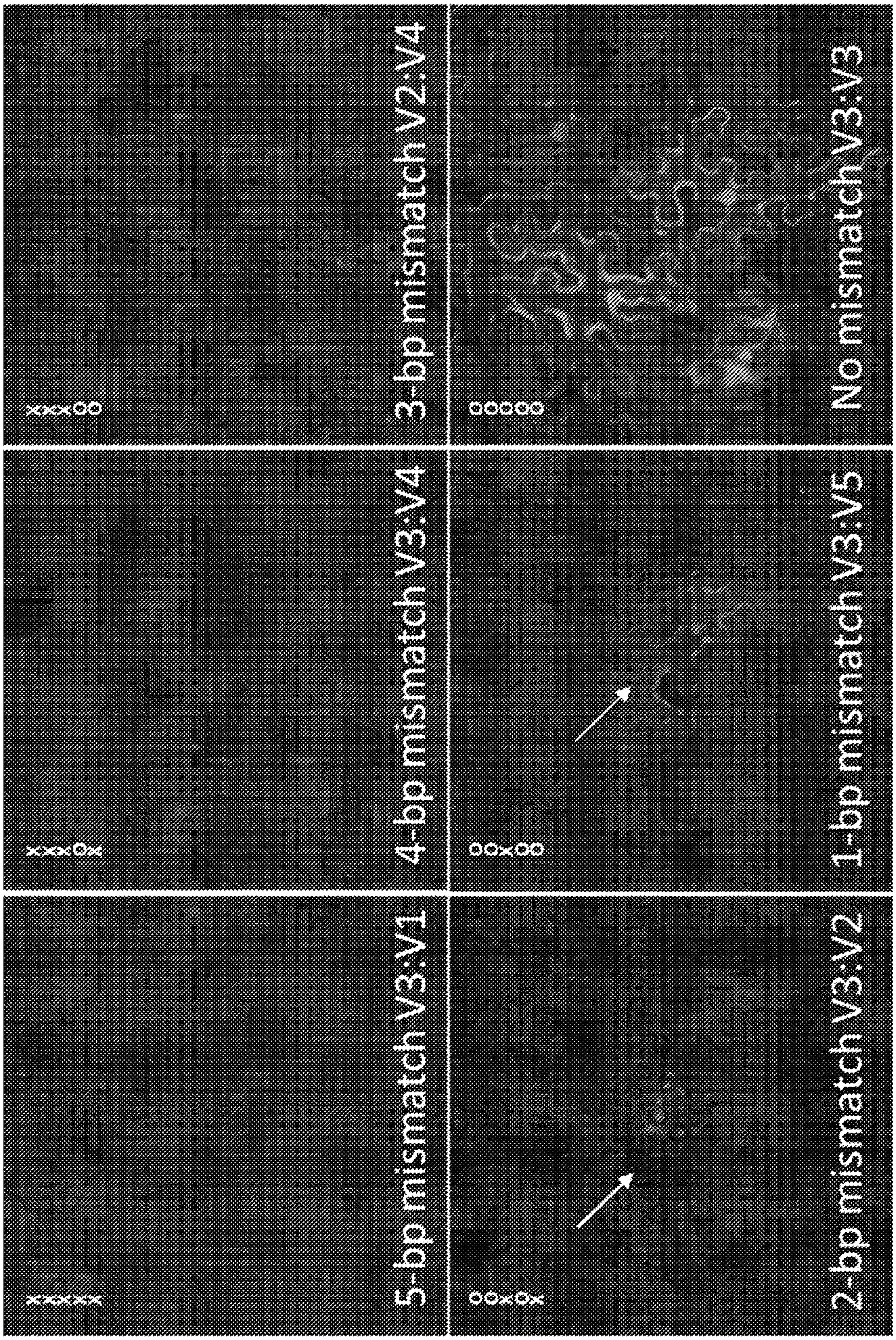
FIG. 17 provides another example of the orthogonality of the CRISPR-Cas logic gate system of the invention. Here, no activation of the mCherry output gene is observed when crRNA and tracrRNA harbor three or more mismatches in the lower stem region, whereas some activation is seen with one and two mismatches.
Figure 18:
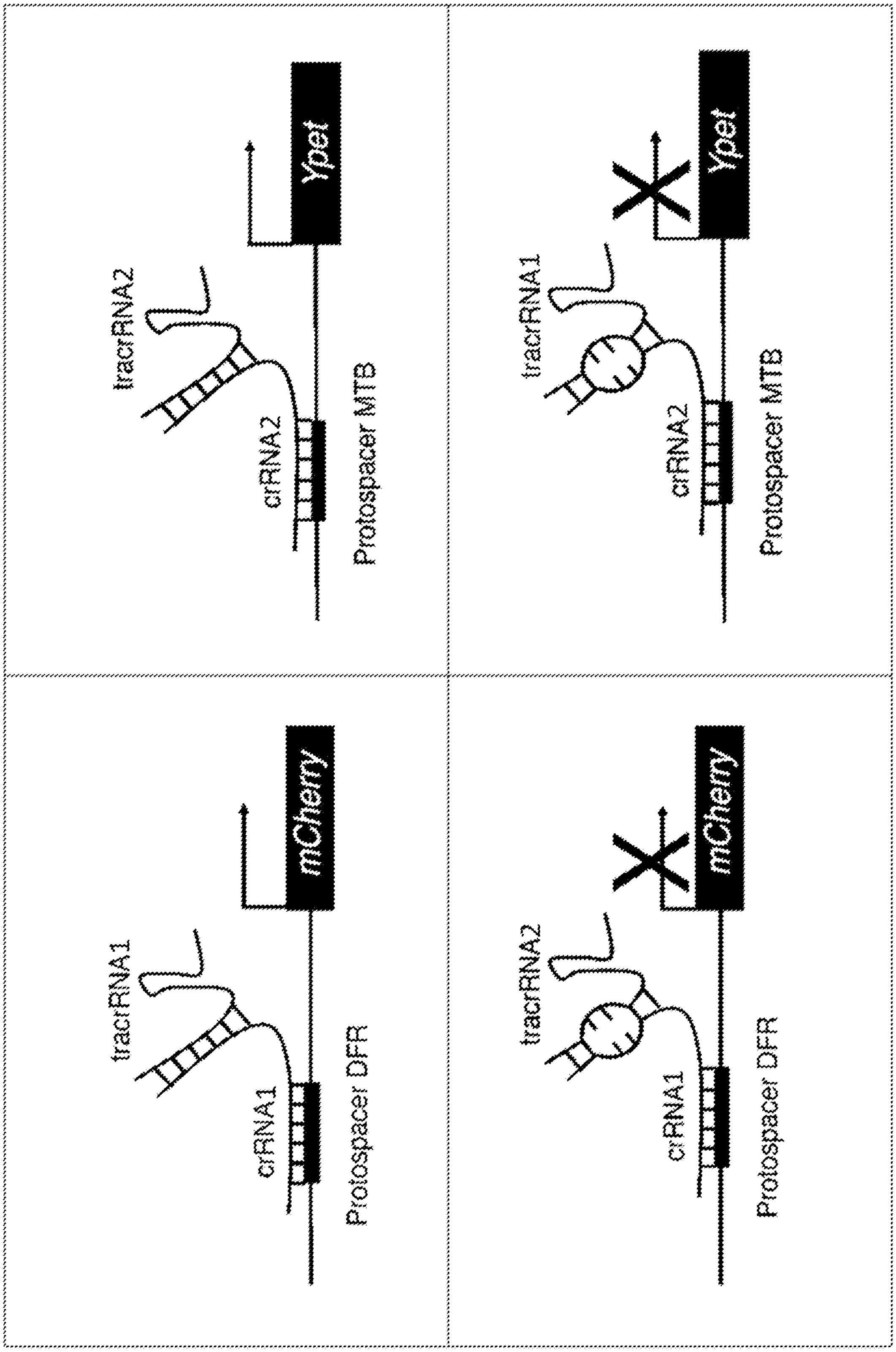
FIG. 18 shows a further example of the CRISPR-Cas logic gate system of the invention. Here, two pseudo-orthogonal pairs of crRNA and tracrRNAs are constructed that work with their respective target protospacers to activate two different fluorescent genes. Unlike matching combinations that induce their respective output reporter genes, non-complementary pairs with 5 mismatches in the stem region fail to activate the output reporters.
Figure 19:
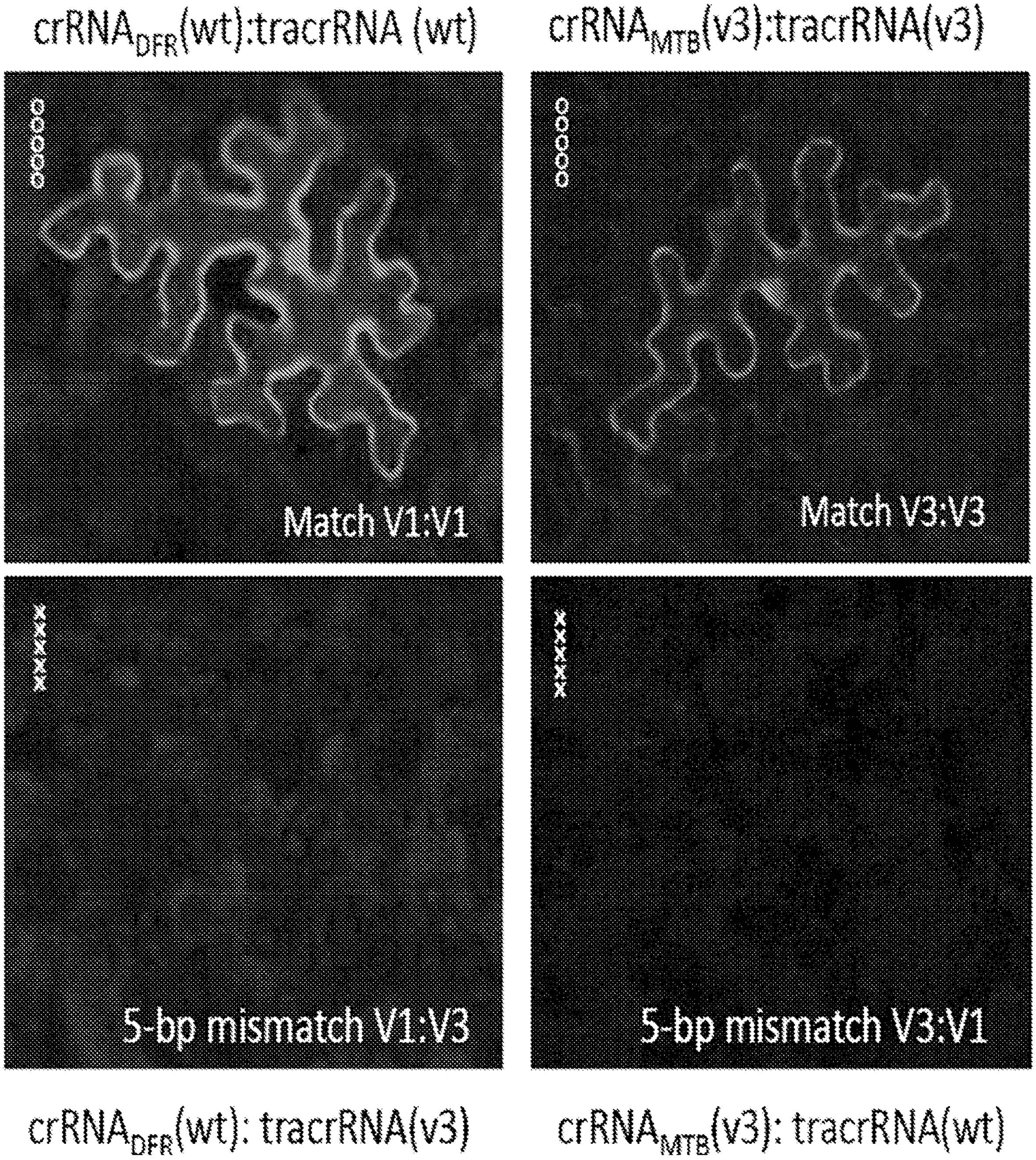
FIG. 19 shows the data for the orthogonal pairs of crRNA and tracrRNAs of FIG. 18.

ATTGACTGGTTGGTGAGAGAAGAGTTTTAGAGCTATGCTGTTTTG*TTTTTTTT*GCAA (Uppercase and underlined: barcode; italics: terminator) [see, e.g., 42 nt crRNA (e.g., FIG. 13); crRNA v1 (e.g., FIG. 14); crRNA (wt) (e.g., FIG. 16); $crRNA_{DFR}$(wt) (e.g., FIG. 19); $crRNA_{WT}$(e.g., FIGS. 20 and 21)]

2. *S. pyogenes*-based short (processed) tracrRNA fused to 2xMS2, version 1:

(SEQ ID NO: 10)

ATTGAAACAGCATAGCAAGTTAAAATAAGGCTAGTCCGTTATCAACTTGAAAAA

GTGGCACCGAGTCGGTGC*GGGAGC*ACATGAGGAATCACCCATGT*GCGACTC*CCACAGTCACTGGG

*GAGTCTTCCCTTTTTTTT*GCAA (bold and smaller font: MS2; italics and underlined: linker) [see, e.g., 75 nt tracrRNA (e.g., FIG. 13); tracrRNAv1 (WT) (e.g., FIG. 14); tracrRNA (wt) (e.g., FIGS. 16 and 19); tracrRNA v1 (e.g., FIG. 17); $tracrRNA_{WT}$ (e.g., FIGS. 20 and 21)]

3. *S. pyogenes*-based long (unprocessed) crRNA targeting SIDFR protospacer:

(SEQ ID NO: 11)

ATTGTTTTAGAGCTATGCTGTTTTGAATGGTCCCAAAACGACTGGTTGGTGAG

AGAAGAGTTTTAGAGCTATGCTGTTTTGAATGGTCCCAAAAC*TTTTTTTT*GCAA (bold: full repeat) [see, e.g., 92 nt crRNA (e.g., FIG. 13)]

4. *S. pyogenes*-based long (unprocessed) tracrRNA fused to 2xMS2:

(SEQ ID NO: 12)

ATTGTTGGAACCATTCAAAACAGCATAGCAAGTTAAAATAAGGCTAGTCCGTTAT

CAACTTGAAAAAGTGGCACCGAGTCGGTGC*GGGAGC*ACATGAGGAATCACCCATGT*GCGA*

*CTC*CCACAGTCACTGGG*GAGTCTTCCCTTTTTTTT*GCAA

Figure 13:
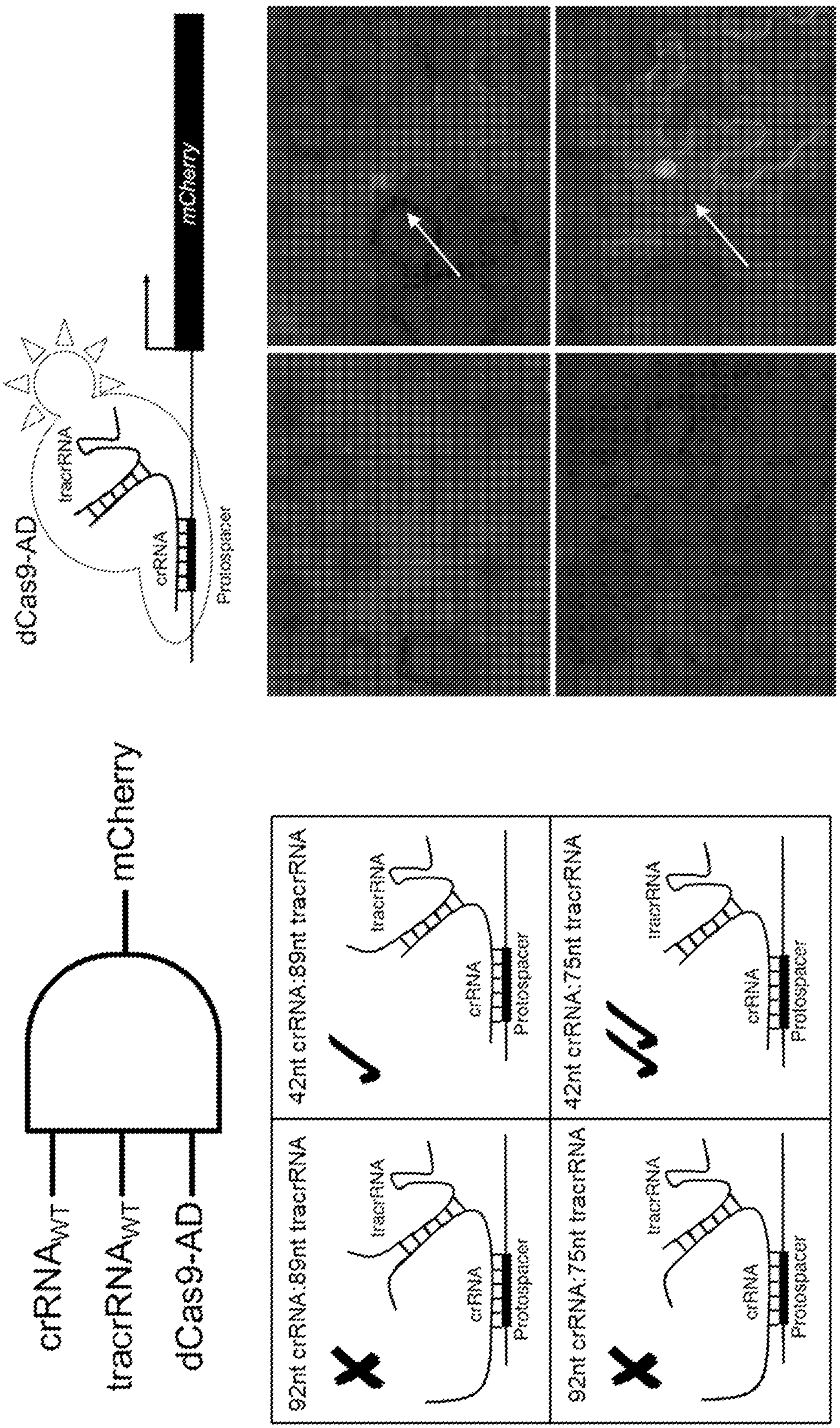
FIG. 13 provides an example of basic three-input logic AND gates that converge on the activation of mCherry expression using crRNA and tracrRNA of different lengths. Different versions of gRNAs were tested that correspond to the unprocessed and processed forms of these small RNAs. The short versions of gRNAs gave a stronger output reporter signal than the full-length crRNA/tracrRNA.
Figure 14:
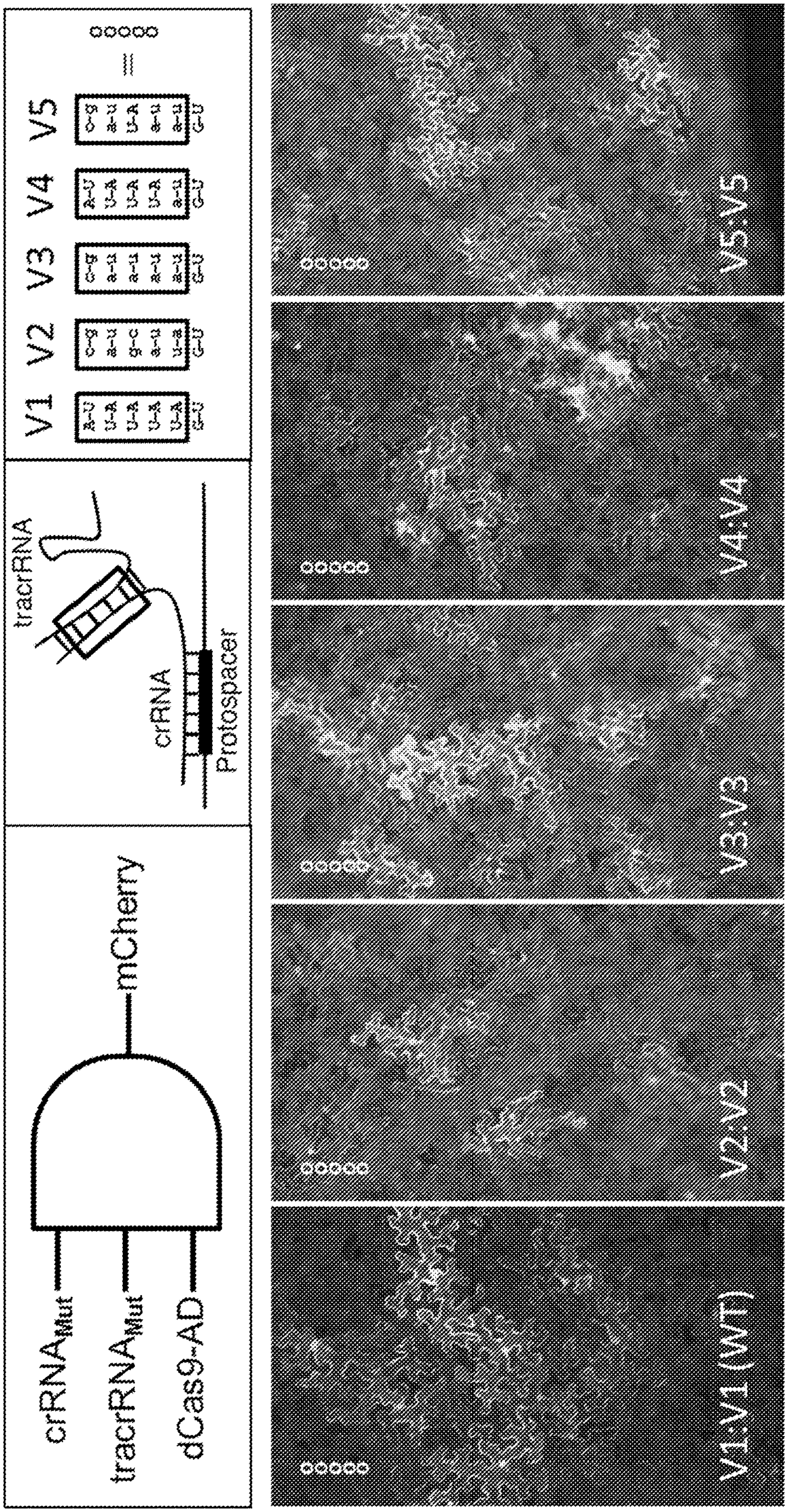
FIG. 14 demonstrates the use of the logic gate system of the invention using four mutant but complementary pairs of the crRNA and tracr RNAs that harbor 1 to 5 mutations in the lower stem and their ability to form functional complexes with dCas9 and turn "on" the output mCherry gene. All four were functional and comparable in their activity to V1, the wild type (WT) reference. Even the gRNA pairs with 5 complementary mutations in the 5 boxed nucleotides of the lower stem were functional.
Figure 15:
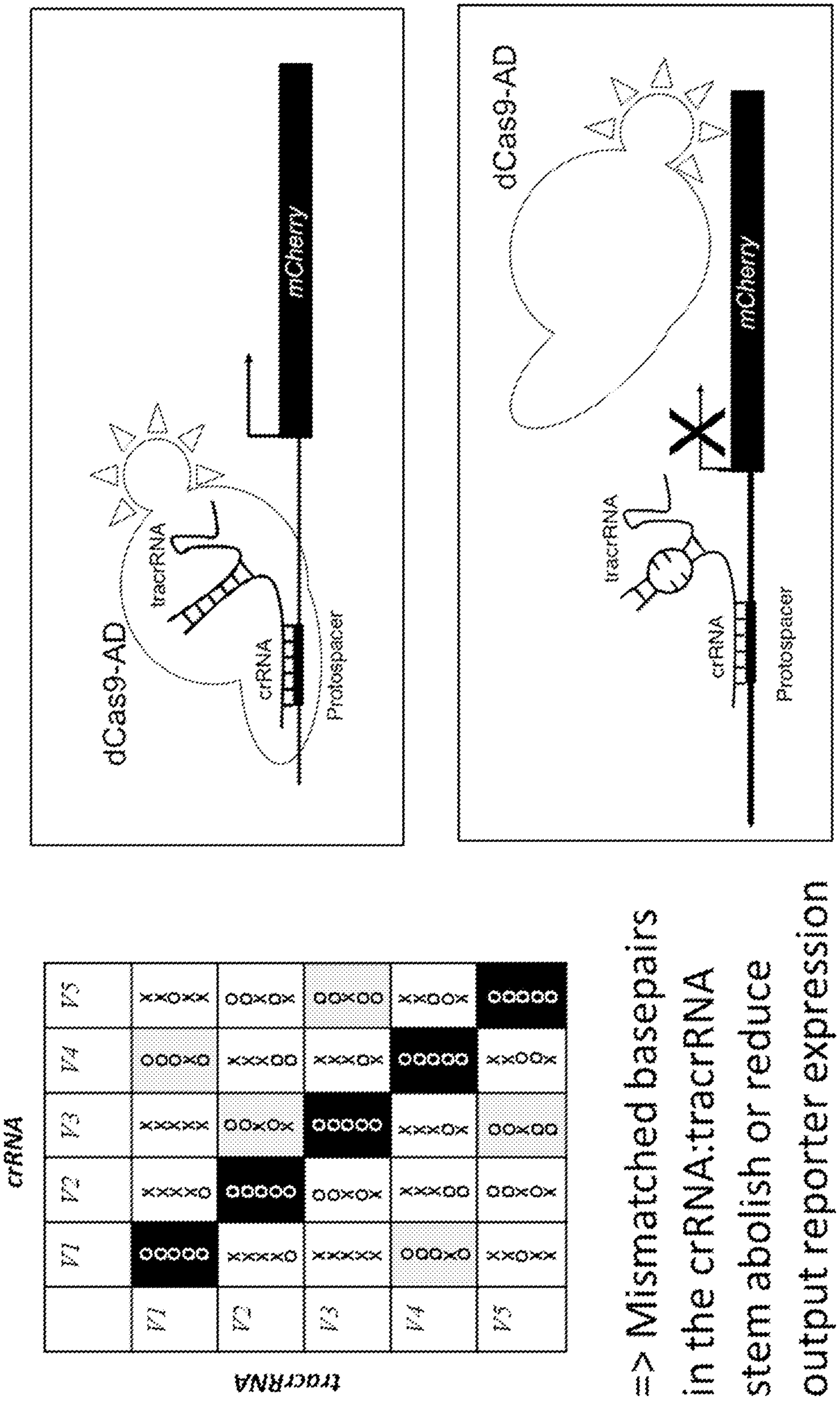
FIG. 15 tests the orthogonality of mutant pairs using five versions of crRNAs and tracrRNAs 25 (5×5) pairwise combinations and shows how many mismatches in the lower stem are required to disrupt the basepairing. These combinations contain 1, 2, 3, 4, or 5 mismatches (as indicated by the x's). Full output reporter activity is observed only in perfect-match combinations (highlighted in dark boxes), and that a single mismatch in the lower stem can reduce the reporter activity. Three or more mismatches in the crRNA/tracrRNA lower stem are enough to completely disrupt the dCas9-mediated activation of the mCherry reporter, whereas 1 or in one case 2 mismatches provide basal reporter activation.

[see, e.g., 89 nt tracrRNA, e.g., FIG. 13)]

5. Examples of A pyogenes crRNA/tracrRNA lower stem mutations (see, e.g., FIGS. 14, 16, 17, and 19) shown in the following nine sequences:

a. Mutated *S. pyogenes*-based short (processed) crRNA targeting SIDFR protospacer, version 2:

(SEQ ID NO: 13)

ATTGACTGGTTGGTGAGAGAAGAGTagacGAGCTATGCTGTTTTG*TTTTTTTT*GCAA (lowercase: mutation)

b. Mutated *S. pyogenes*-based short (processed) tracrRNA fused to 2xMS2, version 2:

(SEQ ID NO: 14)

ATTGAAACAGCATAGCAAGTgtctATAAGGCTAGTCCGTTATCAACTTGAAAAAGT

GGCACCGAGTCGGTGC*GGGAGCAC*ACATGAGGAATCACCCATGT*GCGACTC*CCACAGTCACTGGG*GA*

*GTCTTCCCTTTTTTTT*GCAA c. Mutated *S. pyogenes*-based short (processed) crRNA targeting SIDFR protospacer, version 3:

(SEQ ID NO: 15)

ATTGACTGGTTGGTGAGAGAAGAGaaaacGAGCTATGCTGTTTTG*TTTTTTTT*GCAA d. Mutated *S. pyogenes*-based short (processed) tracrRNA fused to 2xMS2, version 3:

(SEQ ID NO: 16)

ATTGATTGAAACAGCATAGCAAGTgttttTAAGGCTAGTCCGTTATCAACTTGAAAAAGTG

GCACCGAGTCGGTGC*GGGAGCAC*ACATGAGGAATCACCCATGT*GCGACTC*CCACAGTCACTGGG*GAG*

*TCTTCCCTTTTTTTT*GCAA e. Mutated *S. pyogenes*-based short (processed) crRNA targeting SIDFR protospacer, version 4:

(SEQ ID NO: 17)

ATTGACTGGTTGGTGAGAGAAGAGaTTTAGAGCTATGCTGTTTTG*TTTTTTTT*GCAA

-continued f. Mutated *S. pyogenes*-based short (processed) tracrRNA, version 4:

(SEQ ID NO: 18)

ATTGAAACAGCATAGCAAGTTAAAtTAAGGCTAGTCCGTTATCAACTTGAAAAAG

TGGCACCGAGTCGGTGC*GGGAGCAC*ACATGAGGAATCACCCATGT*GCGACTC*CCACAGTCACTGGG*G*

*AGTCTTCCCTTTTTTTT*GCAA g. Mutated *S. pyogenes*-based short (processed) crRNA targeting SIDFR protospacer, version 5:

(SEQ ID NO: 19)

ATTGACTGGTTGGTGAGAGAAGAGaaTacGAGCTATGCTGTTTTG*TTTTTTTT*GCAA h. Mutated *S. pyogenes*-based short (processed) tracrRNA, version 5:

(SEQ ID NO: 20)

ATTGAAACAGCATAGCAAGTgtAttTAAGGCTAGTCCGTTATCAACTTGAAAAAGT

GGCACCGAGTCGGTGC*GGGAGCAC*ACATGAGGAATCACCCATGT*GCGACTC*CCACAGTCACTGGG

*GAGTCTTCCCTTTTTTTT*GCAA i. Mutated *S. pyogenes*-based short (processed) crRNA targeting SIMTB protospacer, version 3 (see, e.g., FIG. 19)

(SEQ ID NO: 21)

ATTGATGAAATTAGGATCATGTAGaaaacGAGCTATGCTGTTTTG*TTTTTTTT*GCAA

6. *S. pyogenes*crRNA/tracrRNA upper stem switch (see, e.g., FIG. 20) mutations provided in the following two sequences:

a. Mutated *S. pyogenes*-based short (processed) crRNA targeting SIDFR protospacer, version USM (see, e.g. FIG. 20):

(SEQ ID NO: 22)

ATTGACTGGTTGGTGAGAGAAGAGTTTTAGAcgatacgacaaaTG*TTTTTTTT*GCAA b. Mutated *S. pyogenes*-based short (processed) tracrRNA fused to 2xMS2, version USM:

(SEQ ID NO: 23)

ATTGtttgtcgtatcgAAGTTAAAATAAGGCTAGTCCGTTATCAACTTGAAAAAGTGGCA

CCGAGTCGGTGC*GGGAGCAC*ACATGAGGAATCACCCATGT*GCGACTC*CCACAGTCACTGGG*G*

*AGTCTTCCCTTTTTTTT*GCAA

7. DNA parts for *S. pyogenes* crRNA flanking by ribozymes or by tRNA sequences for RNA Pol II-mediated expression (see, e.g., FIG. 21) provided in the following six sequences:

a. *S. pyogenes*-based short (processed) crRNA targeting SIDFR protospacer, version for HH-HDV fusion (see, e.g. FIG. 21):

(SEQ ID NO: 24)

CGTCGACTGGTTGGTGAGAGAAGAGTTTTAGAGCTATGCTGTTTTG*TTTT*GGCC b. Hammerhead (HH) ribozyme:

(SEQ ID NO: 25)

CCAT*ccagtc*CTGATGAGTCCGTGAGGACGAAACGAGTAAGCTCGTC
(*ccagtc* is to pair spacer's GACTGG)

c. Hepatitis delta virus (HDV) ribozyme:

(SEQ ID NO: 267)

GGCCGGCATGGTCCCAGCCTCCTCGCTGGCGCCGGCTGGGCAACATGCTTCGGCA

TGGCGAATGGGACGCTT
(GGCC is also a part of the HDV sequence)

d. *S. pyogenes*-based short (processed) crRNA targeting SIDFR protospacer, version for tRNA-tRNA fusion:

(SEQ ID NO: 27)

TGCAGACTGGTTGGTGAGAGAAGAGTTTTAGAGCTATGCTGTTTTG*TTTT*AACA e. *Arabidopsis* tRNA-Gly with B2 code:

(SEQ ID NO: 28)

CCAT*aacaaa*GCACCAGTGGTCTAGTGGTAGAATAGTACCCTGCCACGGTACAGAC

CCGGGTTCGATTCCCGGCTGGTGCA
(e.g., *aacaaa*: a 5' leader of pre-tRNA$^{Gly}$, with the following 71-bp long upper-case sequence corresponding to mature tRNA; TGCA is also part of tRNA)

-continued f. *Arabidopsis* tRNA-Gly with B5 code:

(SEQ ID NO: 29)

aacaaaGCACCAGTGGTCTAGTGGTAGAATAGTACCCTGCCACGGTACAGACCCGG

GTTCGATTCCCGGCTGGTGCAGCTT (aaca may also be used as barcode)

8. *S. thermophilus*-based single guide RNA targeting SIDFR protospacer fused to 2xMS2:

(SEQ ID NO: 30)

ATTGACTGGTTGGTGAGAGAAGAGTcTTTGTACTCTGGTACCAGAAGCTACAAAG

ATAAGGCTTCATGCCGAAATCAACACCCTGTCATTTTATGGCAGGGTGGGGAGCA

ACATGAGGAATCACCCATGT*GCGACTC*CCACAGTCACTGGG*GAGTCTTCCCTTTTT*

Figure 22:
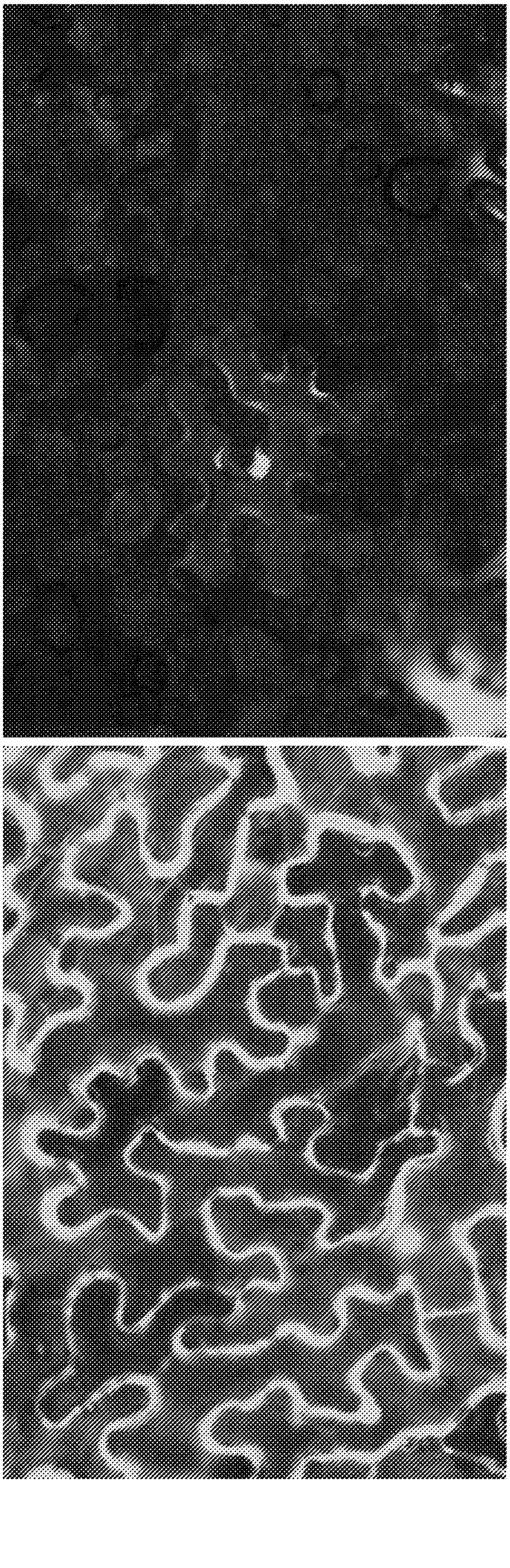
FIG. 22. The *S. thermophilus* single and dual gRNA CRISPR systems are active in tobacco epidermis. This experiment tested the ability of single gRNA (left panel) and crRNA/tracrRNA pair (right panel) to assemble with dCas9 converted to a transcriptional effector by being fused to an EDLL transcriptional activation domain and induce the mCherry reporter. The 35Sp-driven MS2 coat protein gene fused with a VPR transcriptional activation domain serves the purpose of increasing the transcriptional activation capacity of the ribonucleoprotein complex, with the transcriptional effector recruited to it via MS2 target RNA sequences fused to the 3' end of tracrRNA. The absolute strength and the pervasiveness of the mCherry reporter activation in the dual gRNA combination may not be maximized in this experiment relative to the single gRNA control due to the dual gRNA system components being split into three constructs (right panel) and the single gRNA components into two (left panel).
Figure 23:
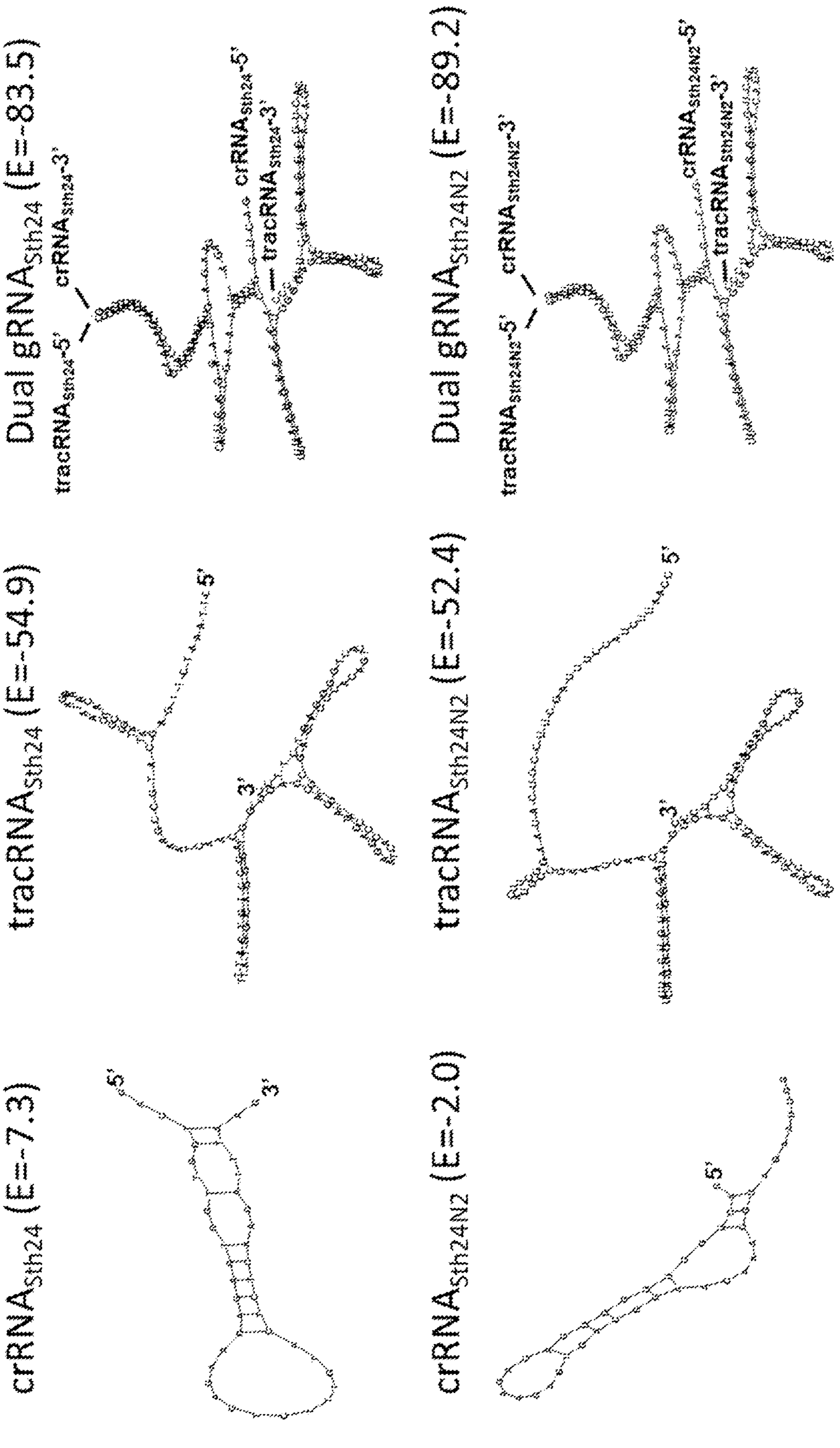
FIG. 23. The free energy (E) of *S. thermophilus* crRNA and tracrRNA intramolecular folding can be increased and that of crRNA:tracrRNA pair can be reduced via targeted mutations in the complementary stem region. The original (upper panel) and computationally optimized (lower panels) versions of crRNA and tracrRNA are displayed. Greater E values (e.g., −2.0 versus −7.3) correspond to less stable structures. crRNA24$_{Sth24}$ (SEQ ID NO:5); tracrRNA24$_{Sth}$ (SEQ ID NO:6); crRNA24$_{SthN2}$ (SEQ ID NO:7); tracrRNA24$_{SthN2}$ (SEQ ID NO:8); dual gRNA$_{Sth24}$ (SEQ ID NO:5 and SEQ ID NO:6); dual gRNA$_{Sth24N2}$ (SEQ ID NO:7 and SEQ ID NO:8).

*TTT*GCAA (see, e.g., FIG. 22)

The foregoing is illustrative of the present invention and is not to be construed as limiting thereof. The invention is defined by the following claims, with equivalents of the claims to be included therein.

TABLE 1

Examples of CRISPR-based constructs and modules (logic AND gates).

| Modules (Logic AND gates and combinations) | dCas9-VPR | crRNA Spacer/Lower Stem Version | tracrRNA Lower Stem Version | Reporter/State |
|---|---|---|---|---|
| WT Spy control* | Spy | Spacer1/StemV1 $_{Spy}$ | trStemV1 $_{Spy}$ | 5xPspacer1 $_{Spy}$:GFP/ON |
| WT Sth1 control** | Sth1 | Spacer1/StemV1 $_{Sth\ 1}$ | trStemV1 $_{Sth\ 1}$ | 5xPspacer1 $_{Sth\ 1}$:mCherry/ON |
| Example 1 (Complementary gRNA pair) | Spy | Spacer1/StemV2 $_{Spy}$ | trStemV2 $_{Spy}$ | 5xPspacer1 $_{Spy}$:GFP/ON |
| Example 2 (Non-complementary gRNA pair) | Spy | Spacer1/StemV1 $_{Spy}$ | trStemV2 $_{Spy}$ | 5xPspacer1 $_{Spy}$:GFP/OFF |
| Module combination AC (Interspecies) | Spy<br>Sth1 | Spacer1/StemV1 $_{Spy}$<br>Spacer2/StemV1 $_{Sth\ 1}$ | trStemV1 $_{Spy}$<br>trStemV1 $_{Sth\ 1}$ | 5xPspacer1 $_{Spy}$:GFP/ON<br>5xPspacer2 $_{Sth\ 1}$:mCherry/ON |
| Module combination AB (Intraspecies) | Spy | Spacer1/StemV1 $_{Spy}$<br>Spacer2/StemV2 $_{Spy}$ | trStemV1 $_{Spy}$<br>trStemV2 $_{Spy}$ | 5xPspacer1 $_{Spy}$:GFP/ON<br>5xPspacer2 $_{Spy}$:mCherry/ON |

*Detailed WT Spy module structure:

dCas9$_{Spy}$-VPR = 35Sp:dCas9$_{Spy}$-VPR-P2A-Csy4 crRNA$_{Spy(Spacer1/StemV1)}$ = UBQ10p:C4H-crRNA$_{Spy(Spacer1/stemV1)}$C4H tracrRNA$_{Spy(trStemV1)}$ = CmYLCVp:C4H-tracrRNA$_{Spy(trStemV1)}$-C4H 5xPspacer1 $_{Spy}$:GFP = 5xPspacer1 $_{Spy}$-MinProm:GFP-Term

**Detailed WT Sth 1 module structure:

dCas9$_{Sth\ 1}$-VPR = 35Sp:dCas9$_{Sth\ 1}$-VPR-P2A-Csy4 crRNA$_{Sth\ 1(Spacer1/StemV1)}$ = UBQ10p:C4H-crRNA$_{Sth\ 1(Spacer1/StemV1)}$-C4H tracrRNA$_{Sth\ 1(trStemV1)}$ = CmYLCVp:C4H-tracrRNA$_{Sth\ 1(trStemV1)}$-C4H 5xPspacer1 $_{Sth\ 1}$:mCherry = 5xPspacer1 $_{Sth\ 1}$-MinProm:mCherry-Term dCas9 is a nuclease-dead version of Cas9; VPR is a transcriptional activation domain; 35S, CmYLCV, and UBQ10 are constitutive promoters; P2A is a self-cleaving peptide; Csy4 is a nuclease that cuts RNA in a C4H hairpin; Spacer and Stem are two variable parts of crRNA; trStem is a variable part of tracrRNA; 5xPspacer is a tandem of five copies of the gRNA target site that is identical to Spacer but also carries a PAM (NGG for Spy and NNAGAAW for Sth1) in the 3'; MinProm and Term are synthetic minimal promoter and 3'UTR; GFP and mCherry are fluorescent protein genes.

That which is claimed is:

1. A logic-gate-based system for modifying gene expression or modifying a genome, the system comprising:

(A) at least one orthogonal pair of hybridizing synthetic nucleic acid constructs, each of the at least one orthogonal pair comprising:

(i) a CRISPR nucleic acid comprising a repeat sequence and at least one spacer sequence having substantial complementarity to a target nucleic acid, the CRISPR nucleic acid operably linked to a first promoter; and (ii) a trans-activating CRISPR (tracr) nucleic acid comprising a sequence that is complementary to the repeat sequence of the CRISPR nucleic acid of the same orthogonal pair of hybridizing synthetic nucleic acid constructs, the tracr nucleic acid operably linked to a second promoter, which when both (i) and (ii) are expressed in a cell, a synthetic CRISPR nucleic acid-tracr nucleic acid (crRNA-tracrRNA) hybrid is formed having a secondary structure comprising a lower stem, and optionally, an upper stem and which hybrid forms a complex with a Type II or Type V CRISPR-Cas effector protein, and (B) at least one nucleic acid operably linked to a third promoter and encoding a Type II or Type V CRISPR-Cas effector protein, that forms a complex with at least one synthetic CRISPR nucleic acid-tracr nucleic acid hybrid formed by the at least one orthogonal pair of hybridizing nucleic acid constructs;

wherein the first promoter, second promoter, and third promoter are different promoters, and wherein the CRISPR nucleic acid of each orthogonal pair of hybridizing synthetic nucleic acid constructs and a tracr nucleic acid of any other of the at least one orthogonal pairs of hybridizing synthetic nucleic acid constructs comprise at least one non-natural mismatch between the repeat sequence of the CRISPR nucleic acid of each orthogonal pair of hybridizing synthetic nucleic acid constructs and the sequence that is complementary to the repeat sequence of the CRISPR nucleic acid of a tracr nucleic acid of any other of the at least one orthogonal pair of hybridizing synthetic nucleic acid.

2. The system of claim 1, wherein the Type II or Type V CRISPR-Cas effector protein is a dCRISPR-Cas effector protein having an inactive HNH and inactive RuvC, or inactive RuvC for a Type V CRISPR Cas effector protein, and the target nucleic acid is located on a fourth promoter that is operably linked to an output nucleic acid.

3. The system of claim 2, wherein the fourth promoter is different from each of the first, second and third promoters.

4. The system of claim 2, wherein the promoter operably linked to the output nucleic acid is a synthetic promoter or a naturally occurring heterologous promoter.

5. The system of claim 2, wherein the promoter operably linked to the output nucleic acid is endogenous to the cell or the output nucleic acid.

6. The system of claim 1, wherein the Type II or Type V CRISPR-Cas effector protein is an active Type II CRISPR-Cas nuclease, a Type II or Type V CRISPR-Cas nickase, and/or a deactivated/dead Type II or Type V CRISPR-Cas effector protein, and the target nucleic acid is any nucleic acid in the cell.

7. The system of claim 1, wherein the lower stem and/or, when present, the upper stem of the synthetic CRISPR nucleic acid-tracr nucleic acid hybrid formed by at least one of the at least one orthogonal pairs of hybridizing nucleic acid constructs comprises at least one nucleotide modification as compared to the lower stem and/or upper stem of the wild type Type II or Type V CRISPR crRNA-tracrRNA hybrid having the same secondary structure as the synthetic hybrid.

8. The system of claim 7, wherein the wild type Type II CRISPR nucleic acid-tracr nucleic acid is a wild type Type II CRISPR nucleic acid and a wild type Type II tracr nucleic acid from a *Lactobacillus* spp. Type II system, a *Bifidobacterium* spp. Type II system, a *Staphylococcus* spp. Type II system, a *Neisseria* spp. Type II system, a *Campylobacter* spp. Type II system, a *Kandleria* spp. Type II system, a *Leuconostoc* spp. Type II system, an *Oenococcus* spp. Type II system, a *Pediococcus* spp. Type II system, a *Streptococcus* spp. Type II system, a *Weissella* spp. Type II system, and/or an *Olsenella* spp. Type II system.

9. The system of claim 8, wherein the wild type Type II CRISPR nucleic acid-tracr nucleic acid is a wild type Type II CRISPR nucleic acid and a wild type Type II tracr nucleic acid from *Streptococcus pyogenes* or *Streptococcus thermophilus.*

10. The system of claim 7, wherein the wild type Type V CRISPR nucleic acid-tracr nucleic acid is a wild type Type V CRISPR nucleic acid and a wild type Type V tracr nucleic acid from an *Alicyclobacillus* spp. Type V system, an *Oleophilus* spp. Type V system, and/or a *Deltaproteobacteria* spp. Type V system.

11. The system of claim 1, wherein the first, second, and third promoters are separately a synthetic promoter, an endogenous promoter, or a naturally occurring heterologous promoter and/or wherein the first, second, and third promoters are the same or different from each other or any combination thereof.

12. The system of claim 1, wherein the first and second promoters operably linked to the CRISPR nucleic acid and the tracr nucleic acid, respectively, of each orthogonal pair of constructs are different from the first and second promoters operably linked to a CRISPR nucleic acid and a tracr nucleic acid, respectively, of any other of the at least one orthogonal pair of hybridizing synthetic nucleic acid constructs.

13. The system of claim 1, wherein each pair of the at least one orthogonal pair of hybridizing synthetic nucleic acid constructs forms a different synthetic CRISPR nucleic acid-tracr nucleic acid hybrid.

14. The system of claim 1, wherein at least one of the synthetic CRISPR nucleic acid-tracr nucleic acid hybrids formed by the at least one orthogonal pair of hybridizing synthetic nucleic acid constructs forms a complex with a Type II or Type V CRISPR-Cas effector protein that is different from a Type II or Type V CRISPR-Cas effector protein that forms a complex with a synthetic CRISPR nucleic acid-tracr nucleic acid hybrid formed by at least one other of the at least one orthogonal pairs of hybridizing synthetic nucleic acid constructs.

15. The system of claim 1, wherein at least one of the synthetic CRISPR nucleic acid-tracr nucleic acid hybrids formed by the at least one orthogonal pair of hybridizing synthetic nucleic acid constructs forms a complex with a Type II or Type V CRISPR-Cas effector protein that is the same as a Type II or Type V CRISPR-Cas effector protein that forms a complex with a synthetic CRISPR nucleic acid-tracr nucleic acid hybrid formed by at least one other of the at least one orthogonal pairs of hybridizing synthetic nucleic acid constructs.

16. The system of claim 1, wherein the system comprises at least two Type II CRISPR-Cas effector proteins and/or Type V CRISPR-Cas effector proteins, each of which is operably linked to a different promoter.

17. The system of claim 1, wherein the system comprises at least two Type II CRISPR-Cas effector proteins and/or Type V CRISPR-Cas effector proteins, each of which is operably linked to the same promoter.

18. The system of claim 1, wherein the at least one orthogonal pair of hybridizing synthetic nucleic acid constructs and at least one Type II CRISPR-Cas effector protein and/or Type V CRISPR-Cas effector protein form a logic gate.

19. The system of claim 18, wherein the logic gate provides AND, OR, NAND, NOR, XOR, XNOR, NOT, or YES Boolean logic functions, or any combination thereof.

20. An isolated cell comprising the logic-gate-based system of claim 1.

21. A method for modifying gene expression or modifying a genome of a cell, comprising introducing into a cell the logic-gate-based system of claim 1, thereby modifying gene expression in the cell or modifying the genome of the cell.

* * * * *